United States Patent
Takahashi et al.

(10) Patent No.: US 8,258,131 B2
(45) Date of Patent: Sep. 4, 2012

(54) FUSED BICYCLIC COMPOUND

(75) Inventors: Yoichi Takahashi, Osaka (JP); Nobumasa Awai, Osaka (JP); Hidenori Akatsuka, Osaka (JP); Takayuki Kawaguchi, Osaka (JP); Toru Iijima, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 244 days.

(21) Appl. No.: 12/671,479

(22) PCT Filed: Jul. 21, 2008

(86) PCT No.: PCT/JP2008/063751
§ 371 (c)(1),
(2), (4) Date: Jan. 29, 2010

(87) PCT Pub. No.: WO2009/017190
PCT Pub. Date: Feb. 5, 2009

(65) Prior Publication Data
US 2010/0204218 A1  Aug. 12, 2010

(30) Foreign Application Priority Data
Aug. 1, 2007 (JP) .................. 2007-200264

(51) Int. Cl.
C07D 265/16 (2006.01)
A61K 31/352 (2006.01)
A61K 31/353 (2006.01)
(52) U.S. Cl. ............. 514/230.5; 544/90; 544/92
(58) Field of Classification Search ........... 544/90, 544/92; 514/230.5
See application file for complete search history.

(56) References Cited

U.S. PATENT DOCUMENTS
5,270,308 A   12/1993  Shiraishi et al.
2005/0107431 A1  5/2005  Greenblatt
2005/0176750 A1  8/2005  Cai et al.
2006/0270695 A1  11/2006  Dolle et al.

FOREIGN PATENT DOCUMENTS
EP    1 844 768 A1     10/2007
JP    2008-115149 A    5/2008
WO    WO-97/23209 A1   7/1997
WO    WO 01/60802 A1   8/2001
WO    WO-03/096982 A2  11/2003
WO    WO-2005/037830 A1  4/2005
WO    WO-2006/077821 A1  7/2006
WO    WO-2006/105442 A2  10/2006
WO    WO-2007/089034 A1  8/2007

OTHER PUBLICATIONS

Office Action issued Jul. 18, 2011, in Chinese Patent Application No. 200880110498.X (with English translation).
Altenbach et al., "Synthesis and Structure—Activity Studies on N-[5-(1H-Imidazol-4-yl)-5,6,7,8-tetrahydro-1-naphthalenyl]methanesulfonamide, an Imidazole-Containing alpha1A-Adrenoceptor Agonist," J. Med. Chem. (2004) vol. 47, pp. 3220-3235.
European Search Report issued Jul. 26, 2010, in connection with EP Application No. 08791966.8.
Meyers et al., "Non-steroidal mineralocorticoid receptor antagonists," Expert Opin. Ther. Patents (2007) vol. 17, No. 1, pp. 17-22.
Salamon et al., "6-Sulfonylchromenes as Highly Potent KAPT-Channel Openers," J. Med. Chem (2002) vol. 45, pp. 1086-1097.
English Translation of International Preliminary Report on Patentability of PCT Application PCT/JP2008/063751 issued Feb. 24, 2010.
Abd-El-Aziz et al., "Synthesis of Hydroquinoline derivatives, aminohydroxychromene, aminocoumarin and their anti-bacterial activities", Heterocycles, 2004, vol. 68, No. 8, pp. 1793-1812, Scheme 4, compound 8a, 8b.
Chemistry and Chemical Industry Dictionary, chemical industry press, p. 620, Jan. 1, 2003.
Office Action dated Jan. 11, 2012 for corresponding Chinese Application No. 200880110498.X.

*Primary Examiner* — Kahsay T Habte
(74) *Attorney, Agent, or Firm* — Birch, Stewart, Kolasch & Birch, LLP

(57) ABSTRACT

The present invention provides a novel fused bicyclic compound having an affinity to a receptor of mineral corticoid (MR), shown by the formula [I]:

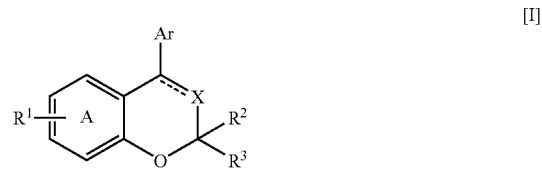

wherein the ring A is a benzene ring having a substituent $R^1$, fused to an adjacent 6-membered heterocyclic ring and further optionally having a substituent(s) other than $R^1$, $R^1$ is an alkylsulfonylamino group etc.,
$R^2$ and $R^3$ are (a) the same of different and a hydrogen atom, an alkyl group or a substituted or unsubstituted aryl group, (b) combined each other to form an oxo group or (c) combined each other at its terminal together with the adjacent carbon atom to form a cycloalkyl group,
X is a group of =N—, =C($R^4$)— or —CH($R^4$)—,
$R^4$ is (a) a hydrogen atom, (b) a cyano group, (c) a halogen atom, (d) an alkyl group, (e) an alkenyl group, (f) a cycloalkyl group (g) an alkanoyl group, (h) a carbamoyl group or (i) a cycloalkenyl group,
Ar is an optionally substituted aromatic cyclic group and a dotted line means presence or absence of a double bond, or a pharmaceutically acceptable salt thereof,
which is useful as an antihypertensive agent etc.

17 Claims, No Drawings

FUSED BICYCLIC COMPOUND

TECHNICAL FIELD

The present invention relates to a novel fused bicyclic compound having an affinity to mineral corticoid receptor (MR), which is useful for treating and/or preventing the diseases or clinical conditions associated with said receptor.

BACKGROUND ART

A physiologically active hydrophobic substance having a low molecular weight such as a steroid hormone demonstrates its effect through an each individual nuclear receptor as a ligand thereof A group of nuclear receptor of steroid hormones forms a genetic superfamily and may control, i.e., activate or inhibit an expression of a target gene at transcriptional level through the function as a ligand-dependent transcriptional factor.

The steroid hormone receptors include a mineralocorticoid receptor (MR), a glucocorticoid receptor (GR), an androgen receptor (AR), an estrogen receptor (ER) and a progesterone receptor (PR). A steroid hormone, which is a ligand of the receptor such as a mineralocorticoid (aldosterone) or a glucocorticoid (cortisol etc.), shows various physiological functions through each receptor (Journal of Endocrinology, 2001; 169:pp. 437-445).

MR-specific ligand, aldosterone, is one of mediators in renin-angiotensin-aldosterone system (RAAS). Formerly, aldosterone has been considered to be nothing but a hormone which is produced only in adrenal glands and acts on distal urinary tubule to regulate water and sodium metabolism. However, recent studies proved that aldosterone is produced in various tissues such as heart, blood vessels, brain and the like and its receptors are widely distributed in cardiovascular tissues and the like. Besides, aldosterone is recognized as not only a precipitating factor of hypertension but also a risk hormone showing various impeding effects on cardiovascular tissues (e.g., cardiac fibrosis/necrosis, potentiation of catecholamine activity, deterioration of baroreceptor response).

In the recent large scale clinical trials (RALES and EPHESUS), it was confirmed that the concomitant use of an aldosterone receptor antagonist (eplerenone or spironolactone) with a conventional medicament such as an ACE inhibitor and the like significantly reduced hospitalization and mortality rate in patients with severe heart failure and significantly ameliorate the prognosis of patients with acute cardiac infarction (New England Journal of Medicine, 2003; 341: p. 709-717, New England Journal of Medicine, 2003; 348: p. 1309-1321). In this regard, it is considered that effective blockade of such hormone is important to establish the therapy of the cardiovascular diseases associated with aldosterone and its receptors.

As mentioned above, any ligands having an affinity to MR and activity of modulating the receptor function, namely repressors, antagonists, agonists, partial antagonists or partial agonists, may be useful as medicaments for prevention or treatment of the diseases or clinical states associated with aldosterone. On the other hand, a steroidal MR-ligand such as spironolactone or eplerenone has been often associated with specific and serious side effects (e.g., gynecomastia, irregular menses, erectile dysfunction), and therefore it has been desired to develop a compound having safety as a medicament without such side effects.

Up to now, 6H-dibenz[b,e]oxepine derivatives (WO2005/066161), dihydropyridine derivatives (WO2005/097118), dibenzo[b, d]pyrane derivatives (Bioorganic and Medicinal Chemistry Letters, 2004; 14: p. 2079-2082), 1,4-dihydro-2H-3,1-benzoxazin-6-yl-sulfonamide derivative (WO2006/077821) and the like have been known as a non-steroidal ligand having an affinity to MR. However, no fused bicyclic compound such as the compound of the present invention (a 1,3-benzoxazine derivative or a chromen derivative) having MR-modulating activity (e.g., MR-antagonizing activity) has been reported.

On the other hand, a 1,3-benzoxazine derivative or a chromen derivative is disclosed in e.g., U.S. Pat. No. 5,270,308, WO 2005/037830 and Journal of Medicinal Chemistry, 2002; 45(5): p. 1086-1097. In addition, the applicant already filed a patent application relating to 3,4-dihydro-1,4-benzoxazine derivatives having MR-modulating activity such as MR-antagonistic activity etc. (WO2007/089034) separately.

DISCLOSURE OF INVENTION

The object of the present invention is to provide novel fused bicyclic compounds having a mineralocorticoid receptor (MR)-modulating activity.

The present invention relates to a novel fused bicyclic compounds compound of the following formula [I]:

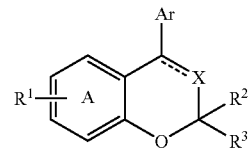

wherein the ring A is a benzene ring having a substituent $R^1$, fused to an adjacent 6-membered heterocyclic ring and further optionally having a substituent(s) other than $R^1$, $R^1$ is an alkylsulfonylamino group or an alkylaminosulfonyl group, $R^2$ and $R^3$ are (a) the same of different and a hydrogen atom, an alkyl group or a substituted or unsubstituted aryl group, (b) combined each other to form an oxo group or (c) combined each other at its terminal together with the adjacent carbon atom to form a cycloalkyl group, X is a group of =N—, =C($R^4$)— or —CH($R^4$)—, $R^4$ is (a) a hydrogen atom, (b) a cyano group, (c) a halogen atom, (d) an alkyl group, (e) an alkenyl group, (f) a cycloalkyl group (g) an alkanoyl group, (h) a carbamoyl group or (i) a cycloalkenyl group, Ar is an optionally substituted aromatic cyclic group and A dotted line means presence or absence of a double bond, or a pharmaceutically acceptable salt thereof.

Besides, the present invention relates to a pharmaceutical composition or a mineralocorticoid receptor-modulating agent, especially a MR-receptor antagonist or an aldosteron antagonist, comprising a compound of the formula [I] described above or a pharmaceutically acceptable salt thereof.

Effect of Invention

The compound of the present invention has a high affinity to a mineralocorticoid receptor (MR) of mammals For example, in a biding assay using a rat MR and $^3$H-aldosterone, which was conducted according to a method disclosed in The Journal of Pharmacology and Experimental Therapeutics, 1987; 240: p. 650-656 (details were described in Example later), typical compounds of the present invention such as N-[4-(4-chlorophenyl)-2,2-dimethyl-2H-1,3-benzoxazin-7-yl]methanesulfonamide, N-[4-(4-fluorophenyl)-2,2,3-trimethyl-2H-chromen-7-yl]methanesulfonamide and the like showed Ki values less than 10 µM in an aldosterone binding to MR derived from a rat kidney. Accordingly, the compound [I] is useful for treating and/or preventing the diseases associated with MR, e.g., circulatory system disease including hypertension and heart failure etc.

The compound [I] of the present invention above or a pharmaceutically acceptable salt thereof is characterized by having a small risk for causing side effects such as irregular menses and gynecomastia etc., which are often observed in an aldosterone antagonist (spironolactone, eplerenone etc.). Moreover, the compound [I] of the present invention includes a compound with a preferable profile as a medicine, e.g., having a small risk for causing side effects on the ground of CYP-enzyme induction and/or time-dependent CYP-inhibition (TDI) etc., or a half-life in blood suitable for once-daily administration.

BEST MODE TO CARRY OUT INVENTION

In the compound [I] of the present invention, examples of a substituent on the ring A include one or two group(s) selected from a halogen atom and an alkyl group.

Examples of an aromatic cyclic group of Ar include (a) a 6- to 10-membered monocyclic or bicyclic aryl group such as a phenyl group or a naphthyl group, or (b) a 5- to 10-membered monocyclic or bicyclic heteroaryl group containing one or more heteroatom(s) selected from a sulfur atom, an oxygen atom and a nitrogen atom such as a thienyl group, a furyl group, a pyridyl group, a benzofuranyl group and a benzothienyl group. Moreover, said aromatic cyclic group is optionally substituted with the same or different one or more substituent(s), and examples of the substituent include (a) a halogen atom (a fluorine, chlorine, bromine or iodine atom), (b) a cyano group, (c) an alkyl group (a methyl or ethyl group), (d) a trihalogenoalkyl group (a trifluoromethyl group etc.), (e) an alkoxy group (a methoxy, ethoxy or propoxy group etc.) and the like.

Preferred examples of the optionally substituted aromatic cyclic group include (1) a phenyl group optionally substituted with one or more substituent(s) selected from a halogen atom, a cyano group, an alkyl group and a trihalogenoalkyl group, (2) a pyridyl group optionally substituted with a halogen atom, (3) a benzofuranyl group, (4) a benzothienyl group and the like.

When $R^2$ or $R^3$ is an aryl group, examples of said aryl group include a 6- to 10-membered monocyclic or bicyclic aryl group such as a phenyl group or a naphthyl group. When $R^2$ or $R^3$ is an aryl group, said aryl group is optionally substituted with one or two halogen atom(s).

The compound [I] of the present invention includes a compound wherein the ring A is a benzene ring optionally substituted with one or more substituent(s) selected from a halogen atom and a $C_{1-8}$ alkyl group, $R^1$ is a $C_{1-8}$ alkylsulfonylamino group or a $C_{1-8}$ alkylaminosulfonyl group, $R^2$ and $R^3$ are (a) the same of different and a group selected from a hydrogen atom, a $C_{1-8}$ alkyl group, and a 6- to 10-membered monocyclic or bicyclic aryl group (said aryl group is optionally substituted with a halogen atom), (b) combined each other to form an oxo group or (c) combined each other at its terminal together with the adjacent carbon atom to form a $C_{3-10}$ cycloalkyl group, $R^4$ is a hydrogen atom, a cyano group, a halogen atom, a $C_{1-6}$ alkyl group, a $C_{2-6}$ alkenyl group, a $C_{3-10}$ cycloalkenyl group, a $C_{1-7}$ alkanoyl group, a carbamoyl group or a $C_{3-8}$ cycloalkenyl group, Ar is a 6- to 10-membered monocyclic or bicyclic aryl group optionally containing one or more heteroatom(s) selected from a sulfur atom, an oxygen atom and a nitrogen atom (said aryl group is optionally substituted with a halogen atom), and $R^1$ is bonded at the position 5, 6 or 7 on the following fused ring moiety of the general formula [I]:

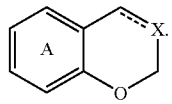

A preferred embodiment of the present invention includes a fused bicyclic compound of the formula [I-A]

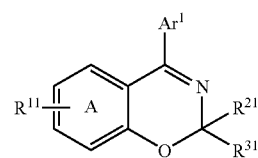

[I-A]

wherein the ring A is a benzene ring having a substituent $R^{11}$, fused to an adjacent 6-membered heterocyclic ring and further optionally having a substituent(s) other than $R^{11}$, $R^{11}$ is an alkylsulfonylamino group or an alkylaminosulfonyl group, $R^{21}$ and $R^{31}$ are the same of different and (a) a hydrogen atom, (b) an alkyl group or (c) a substituted or unsubstituted aryl group and Ar is an optionally substituted aromatic cyclic group, or a pharmaceutically acceptable salt thereof. Among the compounds [I-A], examples of the more preferred compounds include a compound wherein $R^{11}$ is bonded at the position of the following fused ring moiety in the general formula [I-A]:

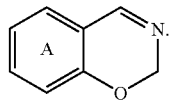

Other preferred embodiment of the present invention includes a fused bicyclic compound of the formula [I-B]

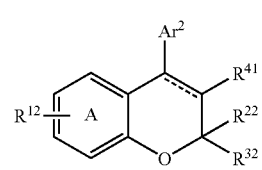

[I-B]

wherein the ring A is a benzene ring having a substituent $R^{12}$, fused to an adjacent 6-membered heterocyclic ring and further optionally having a substituent(s) other than $R^{12}$, $R^{12}$ is an alkylsulfonylamino group or an alkylaminosulfonyl group, $R^{22}$ and $R^{32}$ are (a) the same of different and a hydrogen atom or an alkyl group, (b) combined each other at its terminal together with the adjacent carbon atom to form a cycloalkyl group, or (c) combined each other to form an oxo group, $R^{41}$ is (a) a hydrogen atom, (b) a cyano group, (c) a halogen atom, (d) an alkyl group, (e) an alkenyl group, (f) a cycloalkyl group, (g) an alkanoyl group, (h) a carbamoyl group or (i) a cycloalkenyl group, $Ar^2$ is an optionally substituted aromatic cyclic group and the dotted line means presence or absence of a double bond or a pharmaceutically acceptable salt thereof. Among the above compounds [I-B], examples of the more preferred compounds include a compound in which $R^{12}$ is bonded at the position 7 of the following fused ring moiety in the general formula [I-B]:

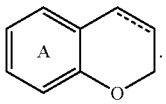

When $R^{21}$ and $R^{31}$ are a substituted or unsubstituted aryl group in the compound [I-A], examples of the aryl group include a phenyl group optionally substituted with a halogen atom.

In the above compounds [I-A] or compounds [I-B], examples of the aromatic cyclic group of $Ar^1$ or $Ar^2$ include (a) a 6- to 10-membered monocyclic or bicyclic aryl group such as a phenyl group or a naphthyl group, (b) a 5- to 10-membered monocyclic or bicyclic heteroaryl group containing one or more heteroatom(s) selected from a sulfur atom, an oxygen atom and a nitrogen atom such as a thienyl group, a furyl group, a pyridyl group, a benzofuranyl group and a benzothienyl group. Besides said aromatic cyclic group is optionally substituted with the same or different one or more substituent(s) and examples of such substituent includes (a) a halogen atom (a fluorine, chlorine, bromine or iodine atom), (b) a cyano group, (c) an alkyl group (a methyl or ethyl group), (d) a trihalogenoalkyl group (a trifluoromethyl group etc.), (e) an alkoxy group (a methoxy, ethoxy or propoxy group etc.) and the like.

Preferred examples of the optionally substituted aromatic cyclic group of $Ar^1$ or $Ar^2$ include (1) a phenyl group optionally substituted with one or two substituent(s) selected from a halogen atom, a cyano group, an alkyl group and a trihalogenoalkyl group, (2) a pyridyl group optionally substituted with a halogen atom, (3) a benzofuranyl group, (4) a benzothienyl group and the like.

A further preferred embodiment of the present invention includes a compound of the formula [I-A-a]:

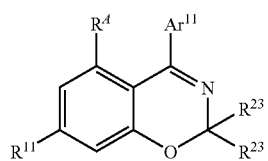

wherein $R^{11}$ is an alkylsulfonylamino group or an alkylaminosulfonyl group, $R^4$ is a hydrogen atom, a halogen atom or an alkyl group, either of $R^{23}$ and $R^{33}$ is a hydrogen atom or an alkyl group and the other is an alkyl group or a phenyl group, $Ar^{11}$ is a 5- to 10-membered monocyclic or bicyclic aryl group (said aryl group may contain a heteroatom selected from a sulfur atom, an oxygen atom and a nitrogen atom) optionally substituted with one or two substituent(s) selected from a halogen atom, a cyano group, an alkyl group, a trihalogenoalkyl group and an alkyloxy group, or a pharmaceutically acceptable salt thereof.

Another further preferred embodiment of the present invention includes a compound of the formula [I-B-a]:

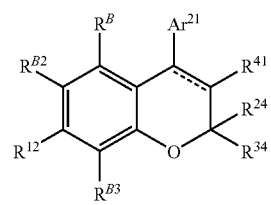

wherein $R^{12}$ is an alkylsulfonylamino group or an alkylaminosulfonyl group, $R^B$, $R^{B2}$ and $R^{B3}$ are the same or different and a group selected from a hydrogen atom, a halogen atom and an alkyl group, $R^{24}$ and $R^{34}$ are (a) the same of different and an alkyl group, (b) combined each other at its terminal together with the adjacent carbon atom to form a cycloalkyl group, or (c) combined each other to form an oxo group, $R^{41}$ is (a) a hydrogen atom, (b) a cyano group, (c) a halogen atom, (d) an alkyl group, (e) an alkenyl group, (f) a cycloalkyl group, (g) an alkanoyl group, (h) a carbamoyl group or (i) a cycloalkenyl group, $Ar^2$ is a 6-membered aromatic cyclic group (said aromatic cyclic group may contain one or two nitrogen atom(s) as a heteroatom) optionally substituted with one or two substituent(s) selected from a halogen atom, an alkyl group and a trihalogenoalkyl group, and the dotted line means presence or absence of a double bond, or a pharmaceutically acceptable salt thereof.

Examples of particularly preferred embodiment of the present invention include, a) a compound of the general formula [I-A-a], wherein $R^{11}$ is a $C_{1-6}$ alkylsulfonylamino group, $R^4$ is a hydrogen atom, a halogen atom or a $C_{1-6}$ alkyl group, either one of $R^{23}$ and $R^{33}$ is a hydrogen atom or a $C_{1-6}$ alkyl group and the other is a $C_{1-6}$ alkyl group, $Ar^{11}$ is a phenyl group optionally substituted with one or two substituent(s) selected from a halogen atom aryl $C_{1-6}$ alkyl group, or b) a compound of the general formula [I-B-a], wherein $R^{12}$ is a $C_{1-6}$ alkylsulfonylamino group, $R^B$ is a hydrogen atom or a $C_{1-6}$ alkyl group, $R^{B2}$ and $R^{B3}$ are hydrogen atoms, $R^{24}$ and $R^{34}$ are the same or different and a $C_{1-6}$ alkyl group, R41 is a hydrogen atom, a cyano group, a halogen atom or a $C_{1-6}$ alkyl group, $Ar^{21}$ is a phenyl group optionally substituted with one or two substituent(s) selected from a halogen atom, a $C_{1-6}$ alkyl group and a trihalogeno $C_{1-6}$ alkyl group.

Concrete examples of the above particularly preferred compound-include a compound selected from the group consisting of N-[4-(4-chlorophenyl)-2,2-dimethyl-2H-1,3-benzoxazin-7-yl]methanesulfonamide;
N-[4-(4-chloro-2-methylphenyl)-2,2-dimethyl-2H-1,3-benzoxazin-7-yl]methanesulfonamide;
N-[4-(4-fluorophenyl)-2,2-dimethyl2H-1,3-benzoxazin-7-yl]methanesulfonamide;
N-[4-(4-fluoro-2-methylphenyl)-2,2-dimethyl-2H-1,3-benzoxazin-7-yl]methanesulfonamide;
N-[4-(4-chloro-3-methylphenyl)-2,2-dimethyl-2H-1,3-benzoxazin-7-yl]methanesulfonamide
N-[4-(4-chloro-3-fluorophenyl)-2,2-dimethyl-2H-1,3-benzoxazin-7-yl]methanesulfonamide;
N-[4-(4-fluoro-3-methylphenyl)-2,2-dimethyl-2H-1,3-benzoxazin-7-yl]methanesulfonamide;
N-[4-(4-chloro-2-fluorophenyl)-2,2-dimethyl-2H-1,3-benzoxazin-7-yl]methanesulfonamide;
N-[5-chloro-4-(4-fluorophenyl)-2,2-dimethyl-2H-1,-benzoxazin-7-yl]methanesulfonamide;
N-[2,2-diethyl-4-(4-fluorophenyl)-2H-1,3-benzoxazin-7-yl]methanesulfonamide;
N-[2-ethyl-4-(4-fluorophenyl)-2-methyl-2H-1,3-benzoxazin-7-yl]methanesulfonamide; and
N-[4-(4-fluorophenyl)-2,2,5-trimethyl-2H-1,3-benzoxazin-7-yl]methanesulfonamide or a pharmaceutically acceptable salt thereof.

Another concrete examples of the particularly preferred compound include a compound selected from the group consisting of N-[4-(4-fluorophenyl)-2,2,3-trimethyl-2H-chromen-7-yl]methanesulfonamide;
N-[3-cyano-4-(4-fluorophenyl)-2,2-dimethyl-2H-chromen-7-yl]methanesulfonamide;
N-[3-fluoro-4-(4-fluorophenyl)-2,2-dimethyl-2H-chromen-7-yl]methanesulfonamide;
N-[4-(4-fluorophenyl)-2,2-dimethyl-3,4-dihydro-2H-chromen-7-yl]methanesulfonamide;
N-[4-(4-chloro-2-methylphenyl)-2,2-dimethyl-2H-chromen-7-yl]methanesulfonamide;
N-[3-cyano-4-(4-fluorophenyl)-2,2-diethyl-2H-chromen-7-yl]methanesulfonamide;
N-[3-cyano-2,2-dimethyl-4-phenyl-2H-chromen-7-yl]methanesulfonamide;
N-[4-(4-chlorophenyl)-3-cyano-2,2-dimethyl-2H-chromen-7-yl]methanesulfonamide;
N-[4-(4-chloro-3-methylphenyl)-3-cyano-2,2-dimethyl-2H-chromen-7-yl]methanesulfonamide;
N-[4-(4-chloro-3-fluorophenyl)-3-cyano-2,2-dimethyl-2H-chromen-7-yl]methanesulfonamide;
N-[4-(4-fluorophenyl)-2,2,5-trimethyl-2H-chromen-7-yl]methanesulfonamide; and
N-[3-cyano-4-(4-fluorophenyl)-2,2,5-trimethyl-2H-chromen-7-yl]methanesulfonamide or a pharmaceutically acceptable salt thereof.

When the compound [I] of the present invention has an asymmetric carbon atom(s) in its molecule, it may exist in the form of a stereoisomer thereof (diastereoisomers, optical isomers) owing to said asymmetric carbon atom(s) thereof, and the present invention also includes either one of the stereoisomers and a mixture thereof.

The compounds [I] of the present invention can be useful for prevention or treatment of various diseases/disease states caused by or associated with MR and/or aldosterone. Such diseases include the following diseases (1) to (6):

(1) Circulation disorders or blood-related disorders: essential hypertension; secondary hypertension (e.g., renovascular hypertension, hypertension due to excessive body fluid); pulmonary hypertension; hypotension; abnormal circadian rhythm in blood pressure; heart failure (e.g., acute heart failure, chronic heart failure, congestive heart failure); angina pectoris; cardiac infarction; cardiomyopathy; cardiac hypertrophy; cardiomyositis; myocardial/vascular fibrosis; myocardial ischemia; baroreceptor dysfunction; arrhythmias; tachycardia; cerebrovascular accidents (CVA) and sequelae thereof; transient ischemic attack (TIA); stroke; cerebrovascular dementia; hypertensive encephalopathy; cerebral infarction; cerebral edema; cerebral circulation disorders; peripheral circulation disorders including Raynoud's disease and Buerger's disease; intermittent claudication; venous function disorders; arteriosclerosis (e.g., coronary artery screlosis, cerebrovascular screlosis, peripheral vascular screlosis); vascular hyperplasia; vascular hyperplasia/occlusion after interventions including percutaneous transluminal coronary angioplasty (PTCA); vascular reocclusion/restenosis after bypass graft (e.g., CABG); rejection after organ transplantation; thrombosis; deep vein thrombosis; obstructive peripheral circulation disorders; obstructive arteriosclerosis; occlusive thromboangiitis; thrombocytopenia; erythrocytosis; multi organ insufficiency; vascular endothelium dysfunction; or kidney disorders (e.g., renal insufficiency, nephritis, glomerulonephritis, IgA nephropathy, progressive nephropathy, glomerulosclerosis, diabetic nephropathy, thrombotic microangiopathy, diseases complicated to dialysis, radionephropathy); vascular purpura; autoimmune hemolytic anemia; disseminated intravascular coagulation (DIC); multiple myelomatosis and the like;

(2) Metabolic diseases: hyperglycemia/diabetes mellitus and diseases complicated thereto (e.g., diabetic nephrosis, diabetic retinopathy, diabetic neuropathy); metabolic syndrome or metabolic disorders (e.g., hyperlipidemia, hypercholesterolemia, obesity, hyperuricemia, hypokalemia, hypernatremia, glucose intolerance); and the like;

(3) Central nervous system or neurodegenerative disorders: neural disorders caused by stroke, cerebral infarction, cranial trauma, spinal cord injury or brain edema; perception disorders/impairment; autonomic nervous dysfunction/impairment; multiple sclerosis; memory disorders; consciousness disorders; mood disorders including depression and bipolar disorder; anxiety disorder; personality disorder; amnesia; dementia; epilepsy; alcohol dependency; Alzheimer's disease; Parkinson's disease; amyotrophic lateral sclerosis; and the like;

(4) Inflammatory or allergic diseases: rheumatoid arthritis; gout; thylotropic gonitis; osteoarthritis; periosteal inflammation; bursitis; ankylosing myelitis; atopic dermatitis; contact dermatitis; psoriasis; allergic rhinitis; hay fever; asthma; urticaria; bronchitis; inflammatory pulmonary diseases (e.g., pneumonia, chronic obstructive pulmonary disease, interstitial pneumonia; *Pneumocystis carinii* pneumonia; pulmonary tuberculosis; pulmonary sarcoidosis); inflammatory bowel disease (e.g., Crohn's disease, ulcerative colitis); collagenosis (e.g., systemic lupus erythematosus, pachyderma, polyarteritis); meningitis; Wegener's granulomatosis; rheumatic fever; post operative/traumatic inflammation; pharyngitis; cystitis; anaphylaxis; tendinitis; conjunctivitis; inflammatory ophthalmic diseases; and the like;

(5) Endocrine diseases: primary or secondary aldosteronism; pseudo-aldosteronism; Bartter's syndrome and the like;

(6) Other diseases including topical diseases: hepatic diseases (e.g., hepatitis, cirrhosis); portal hypertension; digestive organ diseases (e.g., gastritis, gastric ulcer, gastric cancer, post-operative gastric disorder, esophageal ulcer, rupture of gastroesophageal varix, colon polyp, pancreatitis, biliary calculus, piles and the like); prostatic disorders (e.g., prostatic hyperplasia, prostate cancer); bone disorders (e.g., tissue damage caused by bone fracture, osteoporosis, osteomalacia, bone Behcet disease); cancer/tumor (malignant melanoma, leukemia, malignant lymphoma, gastric cancer, intestinal cancer); cachexia; metastasis of cancer; female diseases (e.g., climacteric suffering, gestosis, endometriosis, hysteromyoma, ovarian diseases, mammary gland diseases); infection; septic shock; endotoxin shock; glaucoma; increased occular tension; Meniere disease; dysphagia; sleep apnea; myasthenia gravis; dyalysis hypotension; chronic fatigue syndrome and the like.

The compounds [I] of the present invention include those having potent MR-antagonizing activity (aldosterone-antagonizing activity) and such a compound or a pharmaceutically acceptable salt thereof is particularly useful for prevention or treatment (including its use as diuretics) of various diseases/disease states caused by or associated with hyperactivity of MR and/or increase in aldosterone level, such as cardiovascular diseases including hypertension, heart failure, cardiac infarction, angina pectoris, cardiac hypertrophy, cardiomyositis, cardiac/vascular fibrosis, baroreceptor dysfunction, increased body fluid and arrhythmia, or endocrine diseases including primary/secondary aldosteronism, Addison's disease, Cushing's syndrome and Bartter's syndrome.

The compound [I] of the present invention can be clinically used either in the free form or in the form of a pharmaceutically acceptable salt thereof. The pharmaceutically acceptable salt of the compound includes a salt with an inorganic acid such as hydrochloride, sulfate, phosphate or hydrobromide; a salt with an organic acid such as acetate, fumarate, oxalate, citrate, methanesulfonate, benzenesulfonate, tosylate or maleate; a salt with an alkali metal such as sodium salt and potassium salt and a salt with an alkali earth metal such as a calcium salt.

The compound [I] or a pharmaceutically acceptable salt thereof includes either an intramolecular salt or an additive thereof, and solvates or hydrates thereof.

The present compound [I] or a pharmaceutically acceptable salt thereof can be administered either orally or parenterally in the form of such compound itself or in the form of a pharmaceutical composition comprising the same and a pharmaceutically acceptable carrier. The formulation of such pharmaceutical composition should not be limited and includes any conventional preparations such as tablets, granules, capsules, powders, injections, inhalants or suppositories.

The dose of the compound [I] of the present invention or a pharmaceutically acceptable salt thereof may vary in accordance with the administration routes, and the ages, weights and conditions of the patients. For example, when administered parenterally, it is usually in the range of about 0.001 to 10 mg/kg/day, preferably in the range of about 0.01 to 1 mg/kg/day. When administered orally, it is usually in the range of about 0.01 to 100 mg/kg/day, preferably in the range of 0.1 to 30 mg/kg/day.

A compound [I] of the present invention can be used solely or in combination with one or more other medicaments depending the diseases to be treated and the like.

Examples of such medicament include those as follows:

(a) antihypertensive agents: angiotensin-converting enzyme inhibitors (e.g., enalapril maleate, imidapril hydrochloride, captopril, cilazapril, lisinopril, delapril hydrochloride, temocapril hydrochloride, benazepril hydrochloride, perindopril erbumine, fosinopril sodium, quinapril hydrochloride, moexipril hydrochloride, ramipril, trandorapril, alacepril); angiotensin II receptor blockers (e.g., losartan potassium, candesartan cylexetil, varsartan, irbesartan, telmisartan, olmesartan medoxomil, eprosartan mesylate, forasartan); n-blockers (e.g., atenolol, betaxolol hydrochloride, bisoplolol fumarate, metoprolol tartrate, metprolol citrate, propranolol hydrochloride, nadolol, timolol maleate, acebutolol hydrochloride, penbutolol sulfate, pindolol, carteolol hydrochloride, nipradilol); $\alpha/\beta$-blockers (e.g., carvedilol, labetalol hydrochloride); calcium antagonists (e.g., amlodipine besylate, ferodipine, isradipine, nifedipine, nicardipine hydrochloride, nisoldipine, nitrendipine, benidipine, manidipine hydrochloride, efonidipine hydrochloride, diltiazem hydrochloride); $\alpha_1$-blockers (doxazosin mesylate, prazosin hydrochloride, terazosin hydrochloride); central $\alpha_2$-agonists or other centrally active agent (clonidine hydrochloride, reserpine, methyldopa); vasodilators (hydralazine hydrochloride, minoxidil) and the like, (b) diuretics: thiazide diuretics (e.g., chlorothiazide, hydrochlorothiazide, benzylhydrochlorothiazide, hydroflumethiazide, trichlormethiazide, polythiazide, chlorthalidone, indapamide, metolazone); loop diuretics (e.g., bumetanide, furosemide, tolusemide, mefruside, etacrynic acid); potassium-sparing diuretics (e.g., amiloride hydrochloride, triamterene) and the like, (c) agents for heart failure: nitrates (e.g., nitroglycerin); digitalis (e.g., digoxin, digitoxin); cathecolamines (e.g., dobutamine hydrochloride, denopamine); endotheline antagonists (e.g., bosentan); phosphodiesterase inhibitors (e.g., milrinone lactate, amrinone, olprinone); neutral endopeptidase inhibitors (e.g., fasidotril); atrial natriuretic peptides and the like, (d) anti-arrhythmic agents: sodium channel blockers (e.g., procainamide hydrochloride, flecainide acetate, quinidine sulfate); potassium channel blockers (e.g., amiodarone hydrochloride); calcium channel blockers (e.g., verapamil hydrochloride) and the like, (e) agents for hyperlipidemia: HMG-CoA reductase inhibitors (e.g., pravastatin sodium, atorvastatin calcium, simvastatin, cerivastatin, lovastatin, fluvastatin sodium, rosuvastatin calcium, pitavastatin calcium); fibrate derivatives (e.g., bezafibrate, fenofibrate, clynofibrate, clofibrate, gemfibrozil); squalene synthetase inhibitors and the like, (f) anti-thrombotic agents: anti-coagulation agents (e.g., warfarin sodium, heparin sodium, antithrombin III); thrombolytic agents (e.g., urokinase, t-PA); anti-platelet agents (e.g., aspirin, ticropidin hydrochloride, sulfinpyrazone, dipyridamol, cilostazole) and the like, (g) agents for diabetes mellitus/diabetes-complicated diseases: insulin, $\alpha$-glucosidase inhibitors (e.g., voglibose, acarbose, miglitol, emiglitate); biguanides (e.g., metformin hydrochloride, buformin hydrochloride, fenformin hydrochloride); insulin resistance-improving agents (e.g., pioglitazone, troglitazone, rosiglitazone); insulin secretion-promoting agents (e.g., sulfonylurea derivatives such as tolbutamide, glib enclamide, gliclazide, gliclopiramide, chlorpropamide, glimepiride, glybuzide, glibuzole, tolazamide and acetohexamide); amiline antagonists (e.g., pramlintide); aldose reductase inhibitors (e.g., epalrestat, tolrestat, zenarestat, fidarestat, minalrestat, zopolrestat); neurotrophic factors (e.g., nerve-growth factors/NGF); AGE inhibitors (e.g., pimagedin, piratoxatine); neurotrophic factor production-promoting agents and the like, (h) anti-obesity agents: centrally acting anti-obesity agents (e.g., magindol, fenfluramin, dexfenfluramin, sibutramin); pancreatic lipase inhibitors (e.g., orlistat); β-3 agonists (e.g., SB-226552, BMS-196085, SR-5611-A); anorexigenic peptides (e.g., reptin); cholecystokinin receptor agonists (e.g., lintitript) and the like, (i) non steroidal anti-inflammatory agents: acetaminofen, ibprofen, ketoprofen, ethenzamide, naproxen, dichlofenac, loxoprofen and the like, (j) chemotherapeutics: metabolism antagonists (5-fluorouracil, methotrexate); anti-cancer agents (e.g., vincristine, taxole, cysplatin) and the like, or (k) immuno-modulating agents: immunosuppressants (e.g., cyclosporin, tacrolimus, azathiopurin); immunostimulants: (e.g., crestin, rentinan, schizophyllan); cytokines (e.g., interleukin-1, inteferon); cyclooxygenase inhibitors (e.g., indomethacin, selecoxib, valdecoxib, meloxicam); anti-TNFα antibody (e.g., infliximab) and the like.

When the compound [I] is used in a combination with other medicaments, the form of administration include (1) administration of a single dosage form (a fixed dose combination) containing the compound [I] and such other medicaments, and (2) concomitant administration of a dosage form containing the compound [I] and a dosage form containing such other medicament(s). In case of (2) mentioned above, the route and time of the administration may varied among the dosage forms.

The compound [I] of the present invention in which le is an alkylsulfonylamino group (compound [I-I]) can be prepared by, for example, the following reaction scheme A1 or A2:

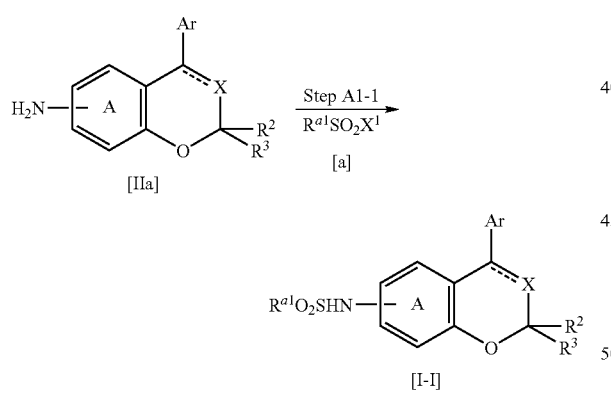

wherein $R^{a1}$ is an alkyl group, $X^1$ is a halogen atom and other symbols are the same as described above,

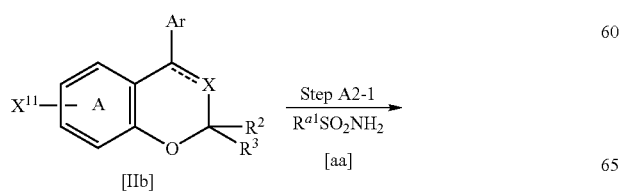

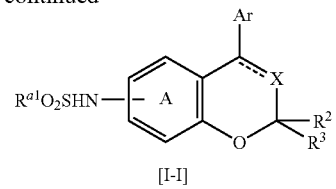

wherein $X^{11}$ is a reactive residue and the other symbols are the same as described above.

Also the compound of the present invention [I] in which $R^1$ is an alkylaminosulfonyl group (compound [I-II]) can be prepared by, for example, the following reaction scheme A3:

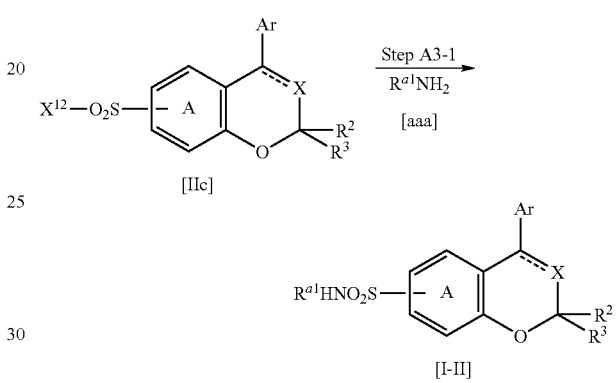

wherein $X^{12}$ is a halogen atom and the other symbols are the same as described above.

Further, the compound of the present invention of the following formula [I-B-2]:

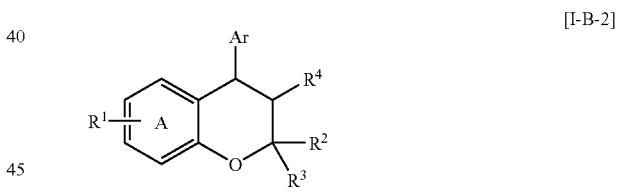

wherein the other symbols are the same as described above, can be prepared by, for example, the following reaction scheme B:

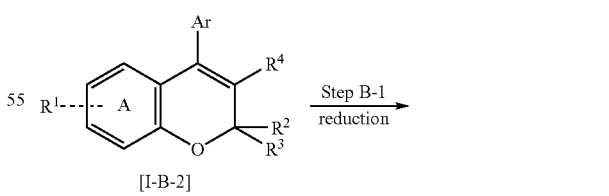

wherein the other symbols are the same as described above.

Step A1-1:

A reaction between the amine compound [IIa] and the compound [a] can be conducted, for example, in a suitable solvent or without a solvent in the presence or absence of a base. Examples of the halogen atom in the compound [a] include a chlorine atom or a bromine atom. Any inert solvent which does not disturb the reaction can be used and examples of the solvent include a halogenated aliphatic hydrocarbon such as chloroform, dichloromethane, dichloroethane or the like; an aromatic hydrocarbon such as benzene, toluene, xylene or the like; an ether such as diethyl ether, diisopropyl ether, tetrahydrofuran, dioxane, 1,2-dimethoxyethane or the like; an ester such as ethyl acetate or the like; an amide such as N,N-dimethylformamide, N,N-dimethylacetamide, 1,3-dimethyl-2-imidazolidinoe or the like, a nitrile such as acetonitrile or the like; pyridine; 2,6-lutidine, a mixture thereof and a mixture of water and these solvents. Among them, dichloromethane, chloroform, toluene, xylene, tetrahydrofuran, dioxane, N,N-dimethylformamide, N,N-dimethylacetamide, 1,3-dimethyl-2-imidazolidinoe and pyridine are preferred and dichloromethane, chloroform, toluene, tetrahydrofuran or pyridine are particularly preferred.

As a base, an organic base and an inorganic base can be used in the reaction. Examples of the organic base include a trialkylamine such as triehtylamine, tributylamine and diisopropylethylamine etc.; a tertially cyclic amine such as 1,4-diazabicyclo[2.2.2]octane, 1,5-diazabicyclo[4.3.0]nona-5-ene, 1,8-diazabicyclo[5.4.0]undeca-7-ene or the like; an aromatic amine such as N,N-dimethylaniline, N,N-diethylaniline, 4-dimethylaminopyridine or the like; pyridine; 2,6-lutidine, 2,3,5-colidine or the like. Examples of the inorganic base include an alkali metal carbonate such as sodium carbonate, potassium carbonate, cesium carbonate or the like; an alkali earth metal carbonate such as calcium carbonate or the like; an alkali metal bicarbonate such as sodium bicarbonate, potassium bicarbonate or the like; an alkali metal hydroxide such as sodium hydroxide, potassium hydroxide, lithium hydroxide or the like. Among them, pyridine, triethylamine, diisopropylethylamine or the alkali metal carbonate is preferable.

In the present reaction, the compound [a] can be used in an amount of 1 to 10 moles, preferably 1 to 2 moles of the compound [IIa]. The base can be used in an amount of 1 to 10 mole, preferably 1 to 2 moles of the compound [Ha]. The present reaction can be carried out under cooling to heating, preferably under ice-cooling to at room temperature.

Step A2-1

Examples of the reactive residue ($X^{11}$) include a halogen atom or a trifluoromethanesulfonyloxy group etc. The compound [IIb] can be reacted with the compound [aa] in a solvent in the presence of a base and a transition metal catalyst. Any solvent which does not disturb the reaction may be used and examples of the solvent include alcohols, aromatic hydrocarbons, dioxane and the like which were described above. Among them, tert-butanol, toluene, xylene and dioxane etc. are preferred. Examples of the base include alkali metal carbonates, alkali metal phosphates and an alkali metal phenoxide etc. Examples of the transition metal catalyst include a palladium catalyst described above, and among them palladium acetate, tris(dibenzylideneacetone)dipalladium and dichlorobis(triphenylphosphine)paladdium are preferable.

In addition, a phosphine compound as a ligand (e.g., triphenylphosphine, 2-dicyclohexylphosphino-2',4',6'-triisopropyl-1,1'-biphenyl, tri-tert-butylphosphine or the like), and an arylboronic acid compound as an activating agent (e.g., phenyl boronic acid or the like) can be used if necessary. In the present reaction, the compound [aa] can be used in an amount of 1 to 10 moles, preferably 1 to 3 moles of the compound [IIb]. The base can be used in an amount of 1 to 10 moles, preferably 1 to 3 moles of the compound [IIb]. The transition metal catalyst can be used in an amount of 0.01 to 0.5 mole, preferably 0.01 to 0.2 mole of the compound [IIb]. The activating agent can be used in amount of 0.005 to 0.3 mole, preferably 0.005 to 0.05 mole of the compound [IIb]. The present reaction can be carried out at 60 to 150° C., preferably at 80 to 120° C.

Step A3-1

This reaction can be conducted in the same manner as Step A1-1 described above.

Step B1

The reduction of the compound [I-B-1] can be conducted in a solvent in the presence of a transition metal catalyst (catalytic hydrogenation). Any solvent which does not disturb the reaction can be used, and examples of the solvent include alcohols such as ethanol. Examples of the transition metal catalyst include palladium-carbon, platinum-carbon, platinum oxide, Raney-nickel and the like. The transition metal catalyst can be used in an amount of 0.01 to 3 moles, preferably 0.1 to 1 mole of the compound [I-B-1]. The present reaction can be carried out under cooling to heating, preferably at room temperature to boiling point of the reaction mixture.

The objective compound [I] of the present invention can be also prepared by further converting the substituent(s) of the compound obtained by the method described above to the other desired substituent(s). The further conversion process can be selected according to the kinds of the objective substituent(s), and may be carried out, for example, in the following methods.

Method (a) A compound [I] having an alkoxy group as a substituent can be prepared by reacting a corresponding compound having a halogen atom as a substituent (or having a substituent including a halogen atom) with an alkanol in a suitable solvent in the presence of a catalyst such as a palladium catalyst, e.g., palladium acetate, and in the presence or absence of an additive such as a phosphine compound, e.g., triphenylphosphine, racemic-2-(di-tert-butylphosphino)-1,1'-binaphthyl, and a base such as an alkali metal carbonate, e.g., potassium carbonate, cesium carbonate etc.

Method (b) A compound having a methyl group as a substituent can be prepared by reacting a corresponding compound [I] having a halogen atom as a substituent with trimethylboroxin in a solvent in the presence of a palladium catalyst such as [1,1-bis(triphenylphosphino)ferrocene]dichloropalladium(II), tetrakis(triphenylphosphine)palladium(0) and the like and a base such as potassium carbonate etc.

Method (c) A compound having an ethyl group as a substituent can be prepared by conducting a catalytic hydrogenation of a corresponding compound [I] having a vinyl group in the presence of a palladium catalyst such as a palladium-carbon.

Method (d) A compound having a cyano group as a substituent can be prepared by reacting a corresponding compound [I] having a halogen atom as a substituent with zinc cyanide in the presence of a palladium catalyst such as tetrakis(triphenylphosphine)palladium(0).

Method (e) A compound having a carbamoyl group as a substituent can be prepared by treating a corresponding compound [I] having a cyano group as a substituent in a solvent such as dioxane with a strong acid such as 6N hydrochloric acid etc. under heating Method (f) A compound having a cycloalkyl group as a substituent can be prepared by reacting a corresponding compound [I] having a halogen atom as a substituent with cycloalkylboronic acid in the presence of a palladium catalyst such as tetrakis(triphenylphosphine)palladium(0) and a base such as potassium phosphate.

Method (g) A compound having a trifluoromethyl group as a substituent can be prepared by reacting a corresponding compound [I] having a iodine atom as a substituent with ethyl 2,2-difluoro-2-(fluorosulfonyl)acetate in the presence of a cuprous sat such as cuprous bromide(I). In addition, the compound having a iodine atom as a substituent, e.g., a compound substituted with an iodine atom at 5-position of 1,4-benzoxazine ring can be prepared by reacting a corresponding compound [I] having no substituent on the 5-position with an iodinating reagent such as bis(pyridine)iodonium tetrafluoroborate.

The compounds obtained by the method described above can be converted to a pharmaceutically acceptable salt if desired. The conversion to a pharmaceutically acceptable salt can be carried out according to a conventional manner.

A compound of the general formula [II-A],

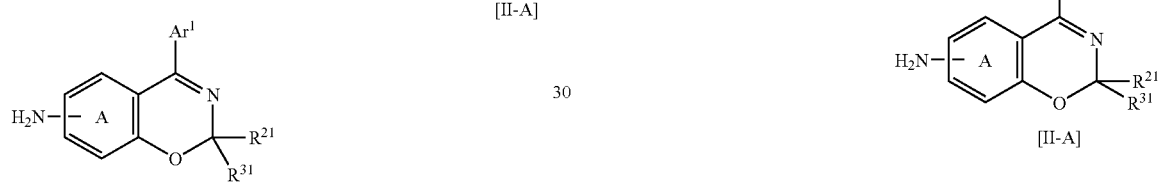

wherein the symbols are the same as defined above, is one of the synthetic intermediates [IIa] of the present invention and can be prepared through the reaction scheme M1 or M2 below.

The reaction scheme M1 is as follows;

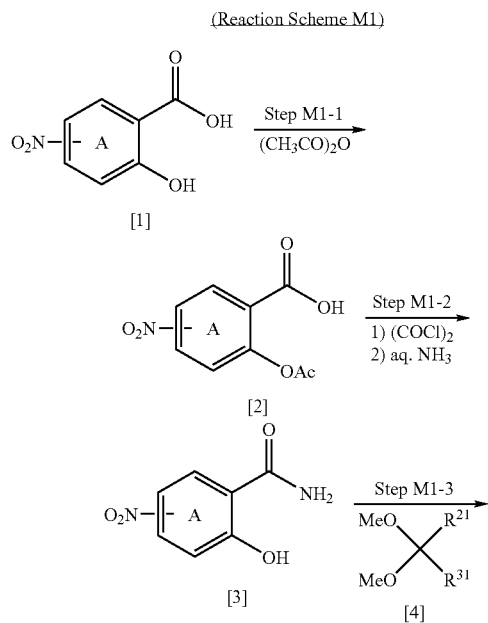

wherein Ac is an acetyl group, Me is a methyl group, Tf is a trifluoromethanesulfonyl group, R' and R" are hydrogen atoms or methyl groups, or both of R' and R" are combined each other at terminal thereof to form an alkylene group, and other symbols are the same as defined above.

Step M1-1

A reaction of the salicylic acid compound [1] and acetic anhydride can be carried out without a solvent at 80 to 140° C. and if necessary, an inert solvent which does not disturb the reaction may be used.

Step M1-2

The acid halide obtained by the reaction of the compound [2] with a halogenating agent such as oxalyl chloride and thionyl chloride etc. can be reacted with ammonia in a solvent under ice-cooling to at room temperature. Any inert solvent which does not disturb the reaction can be used, and examples of the solvent include ethers such as tetrahydrofuran, halogenated aliphatic hydrocarbons such as chloroform, dichloromethane, dichloroethane etc., esters such as ethyl acetate and a mixture of water and these solvents.

The objective compound [3] of the step can be prepared by reacting the compound [2] with an ammonium salt such as ammonium chloride or the like in the presence of a condensing agent (e.g., a water-soluble carbodiimide or the like) and an activator (e.g., 1-hydroxybenzotriazole or the like) at 0 to 30° C. Any inert solvent which does not disturb the reaction can be used, and examples of the solvent include amides such as N,N-dimethylformamide, ethers such as tetrahydrofuran and halogenated aliphatic hydrocarbons such as chloroform, dichloromethane, dichloroethane etc.

Step M1-3

The compound [3] can be reacted with the dimethylacetal compound [4], for example, in a solvent in the presence of an acid catalyst such as p-toluenesulfonic acid or a pyridinium salt thereof at 30 to 130° C. Any inert solvent which does not disturb the reaction can be used and examples of the solvent include ketones such as acetone, and aromatic hydrocarbons such as toluene.

Step M1-4

The compound [5] can be reacted with trifluoromethanesulfonic anhydride (the compound [6]) in a solvent in the presence of a base such as 2,6-lutidine at −30° C. to room temperature. Any inert solvent which does not disturb the reaction can be used and examples of the solvent include halogenated aliphatic hydrocarbons such as dichloromethane.

Step M1-5

The compound [7] can be reacted with the boronic acid compound [8] in a solvent in the presence of a catalyst such as bis(triphenylphosphine)palladium(II) dichloride and a base such as potassium carbonate and potassium phosphonate in the presence or absence of water at 50° C. to the boiling point of the reaction mixture. Any inert solvent which does not disturb the reaction can be used, and examples of the solvent include ethers such as dimethoxyethane and dioxane, and aromatic hydrocarbons such as toluene. Examples of the boronic acid include a compound wherein R' and R" are hydrogen atoms or alkyl groups (e.g., methyl group, ethyl group etc.) and a compound wherein R' and R" are combined each other to form an alkylene group (e.g., ethylene group, propylene group, 1,1,2,2-tetramethylethylene group etc.). Among them, the compound wherein R' and R" are hydrogen atoms and the boronic acid compound of the formula:

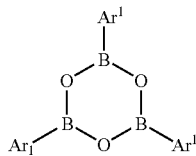

wherein the symbols are the same as defined above, can be preferably used.

Further, the boronic acid compound [8] can be used in a form of ester with N-phenyldiethanolamine shown in the formula:

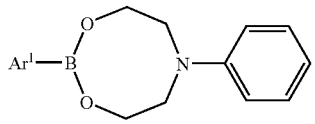

wherein the symbols are the same as defined above.

Step M1-6

The reduction of the nitro group on the compound [9] can be carried out in a solvent in the presence of a reducing agent. Examples of the reducing agent include metals such as tin, iron, zinc and the like or metal salts such as tin chloride etc. In addition, a mineral acid such as hydrochloric acid or ammonium chloride may be added in the reaction system depending on the type of reducing agent.

Any inert solvent which does not disturb the reaction can be used, and examples of the solvent include water, alcohols such as methanol ethanol and propanol, esters such as ethyl acetate, amides such as N,N-dimethylformamide, N,N-dimethylacetoamide and 1,3-dimethyl-2-imidazolidinone, nitriles such as acetonitrile, ethers such as tetrahydrofuran, dioxane, 1,2-dimethoxyethane and a mixture thereof, or a combination of water and these solvents. Among them, ethyl acetate, ethanol and a mixture of water and alcohol are preferable. The reducing agent can be used in an amount of 1 to 5 moles, preferably 1 to 2 moles of the compound [9] and the reaction can be carried out at room temperature to boiling point of the reaction mixture.

The intermediate compound can also be prepared according to the reaction scheme M2 below;

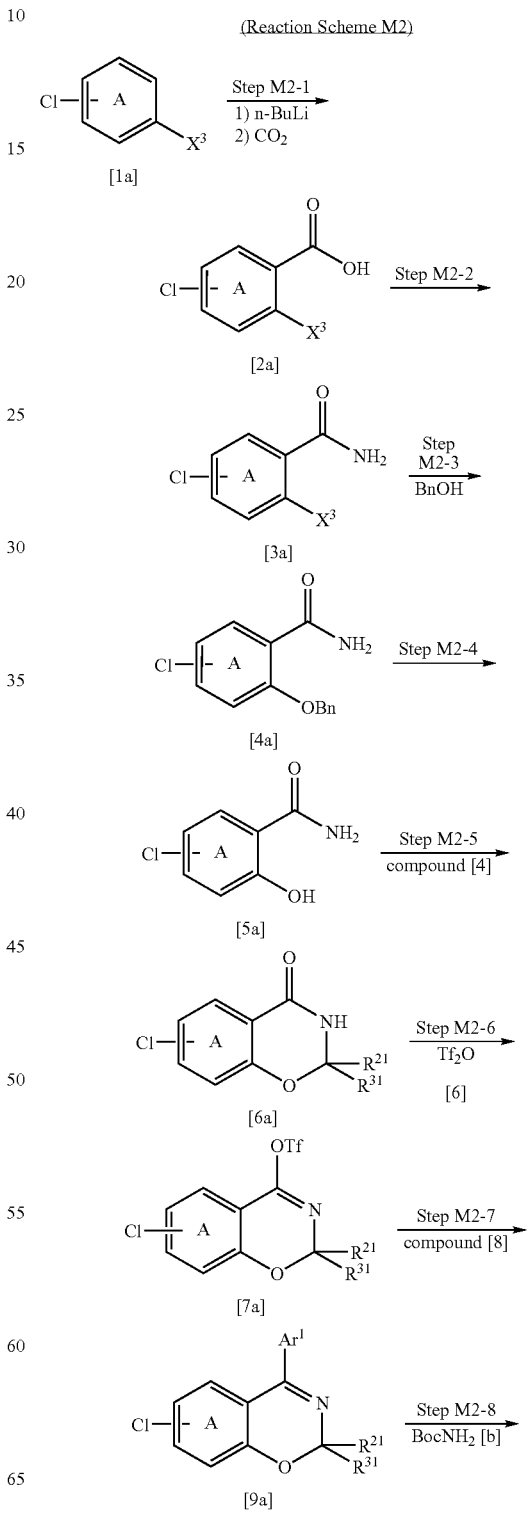

-continued

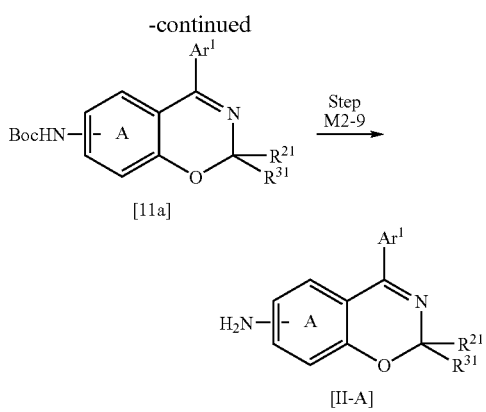

wherein $X^3$ is a halogen atom, Boc is a tert-butoxycarbonyl group, Bn is a benzyl group, Bu is a butyl group, Tf is a trifluoromethanesulfonyl group and the other symbols are the same as defined above.

Step M2-1

The compound [1a] can be reacted with n-butyl lithium and subsequently with carbon dioxide in a solvent at −78 to −20° C. Any inert solvent which does not disturb the reaction can be used and examples of the solvent include ethers such as tetrahydrofuran.

Step M2-2

The reaction can be carried out in the same manner as Step M1-2 described above.

Step M2-3

The reaction of the compound [3a] and benzyl alcohol can be carried out in a solvent in the presence of a base such as sodium hydride under ice-cooling to at 30° C. Any inert solvent which does not disturb the reaction can be used and examples of the solvent include amides such as dimethylformamide.

Step M2-4

The benzyl group of the compound [4a] can be removed by catalytic hydrogenation of said compound in a solvent in the presence of a catalyst such as palladium-carbon under ice-cooling to at room temperature. Any inert solvent which does not disturb the reaction can be used and examples of the solvent include esters such as ethyl acetate and alcohols such as methanol and ethanol.

Step M2-5 to M2-7

These steps can be carried out in the same manner as Steps M1-3, M1-4 and M1-5 respectively.

Step M2-8

The reaction can be carried out in a solvent in the presence of a base and a transition metal catalyst. Any inert solvent which does not disturb the reaction can be used and examples of the solvent include alcohols, aromatic hydrocarbons and ethers. Among them, tert-butanol, toluene, xylene, dioxane and the like are preferred. Examples of the base include alkali metal carbonate, alkali metal phosphate and alkali metal phenoxide. Among them, potassium carbonate, cesium carbonate, potassium phosphate, sodium phenoxide and the like are preferred. Examples of the transition metal catalyst include palladium catalysts and the like, and palladium acetate, tris(dibenzylideneacetone)dipalladium, dichlorobis(triphenylphosphine)palladium and the like are preferred. In addition, a ligand such as triphenylphosphine, 2-dicyclohexylphosphino-2',4',6'-triisopropyl-1,1'-biphenyl and tri-tert-butylphosphine, and an activating agent such as arylboronic acid (e.g., phenylboronic acid) may be added in the present reaction.

The compound [b] in the reaction can be used in amount of 1 to 10 moles, preferably 1 to 3 moles of the compound [9a]. The base can be used in amount of 1 to 10 moles, preferably 1 to 3 moles of the compound [9a]. The transition metal catalyst (and the ligand) in the reaction can be used in amount of 0.01 to 0.5 moles, preferably 0.01 to 0.2 mole of the compound [9a]. The activator in the reaction can be used in amount of 0.005 to 0.3 moles, preferably 0.005 to 0.05 mole of the compound [9a]. The reaction can be carried out at 60 to 150° C., preferably at 80 to 120° C.

Step M2-9

The Boc group of the compound [11a] can be removed in a solvent in the presence of an acid such as hydrochloric acid and trifluoroacetic acid etc. Any inert solvent which does not disturb the reaction can be used, and examples of the solvent include halogenated aliphatic hydrocarbons such as dichloromethane, chloroform and the like, esters such as ethyl acetate and the like, ethers such as dioxane and the like, organic acids and a mixture thereof. The reaction can be carried out under ice-cooling to under heating, preferably under ice-cooling to at room temperature In addition, the intermediate compound [9a] can be also prepared, by, for example, treating a chlorosalicylic acid compound [1b] of the formula:

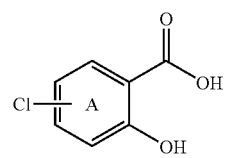

wherein the symbol is the same as defined above, with a halogenating agent such as thionyl chloride or oxalyl chloride to convert it to the corresponding acid halide, reacting said halide with an aromatic cyclic compound [2b] of the formula:

$$Ar^1—H \quad [2b]$$

wherein the symbol is the same as defined above, in a solvent (halogenated aliphatic hydrocarbons such as dichloromethane, chloroform, dichloroethane and the like) in the presence of Lewis acid (aluminium chloride etc.) under ice-cooling to under heating to prepare a ketone compound [3b] of the formula:

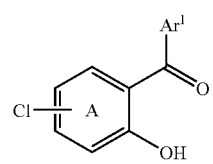

wherein the symbols are the same as defined above,
followed by reacting said compound [3b] and ammonium iodide in a solvent (nitriles such as acetonitrile) in the presence of a base such as triethylamine and a dehydrating agent such as calcium sulfate at room temperature to boiling point of the reaction mixture to give an imine compound [4b] of the formula:

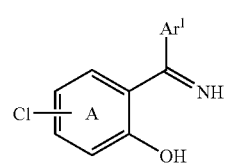

wherein the symbols are the same as defined above, and then, reacting said compound [4b] with a ketone compound [5b] of the formula:

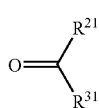
[5b]

wherein the symbols are the same as defined above, or the corresponding dimethylacetal compound thereof (compound [5bb]).

The reaction between the compound [4b] and the compound [5b] (or the compound [5bb]) can be carried out in the same manner as Step M1-3 described above.

Among the intermediate compounds [II-A], a compound of the following formula [II-A-1]:

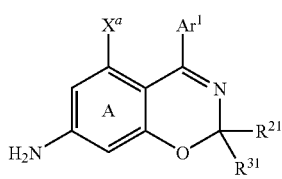
[II-A-1]

wherein $X^a$ is a halogen atom and the other symbols are the same as defined above, can be prepared by reacting a compound of the formula [1c]:

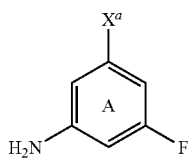
[1c]

wherein the symbols are the same as defined above, with 2,5-hexanedione in a solvent (ehters such as tetrahydrofuran, aromatic hydrocarbons such as toluene and the like) in the presence of an acid catalyst such as p-toluenesulfonic acid to prepare a compound of the following formula [2c]:

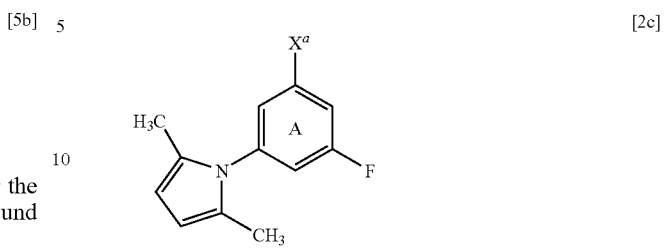
[2c]

wherein the symbols are the same as defined above, followed by treating said compound [2c] in the same manner as Steps M2-1 to M2-7 described above to prepare a compound of the following formula [3c]:

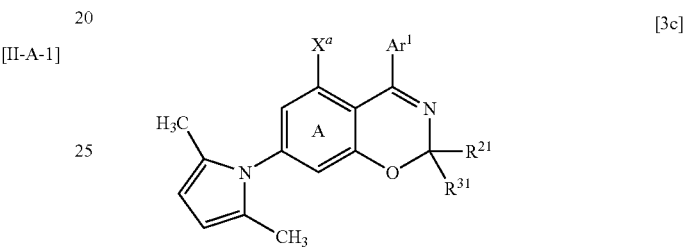
[3c]

wherein the symbols are the same as defined above, and then, treating said compound [3c], for example, in a solvent (a mixture of water and an ether such as 1,4-dioxane etc.) with an acid such as trifluoroacetic acid.

An intermediate compound of the formula [II-B]:

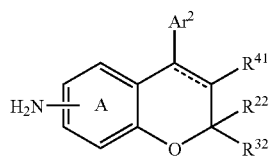
[II-B]

wherein the symbols are the same as defined above, can be prepared for example through the reaction scheme M3 below:

(Reaction Scheme M3)

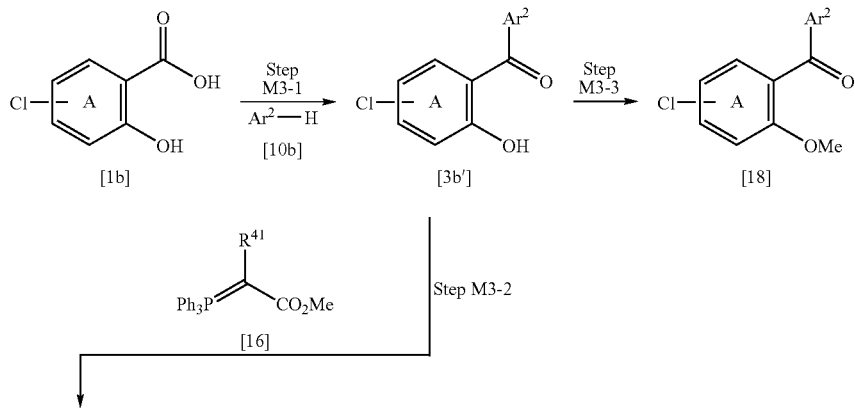

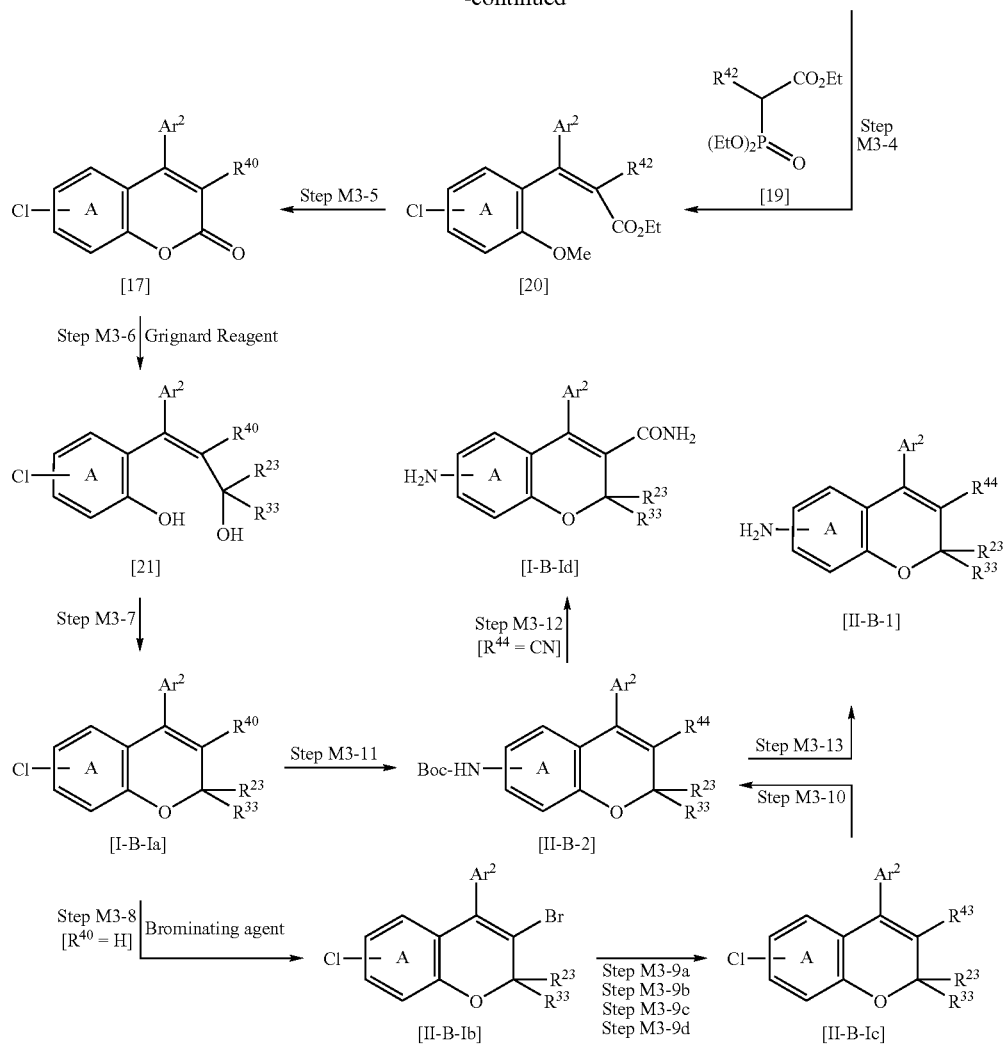

wherein $R^{40}$ is a hydrogen atom, a halogen atom or an alkyl group, $R^{41}$ is a hydrogen atom or an alkyl group, $R^{42}$ is a halogen atom, $R^{43}$ is a cyano group, an alkenyl group, an alkanoyl group or a cycloalkyl group, $R^{44}$ is a hydrogen atom, a halogen atom, a cyano group, an alkyl group, an alkenyl group, an alkanoyl group or a cycloalkyl group, $R^{23}$ and $R^{33}$ are alkyl groups, Me is a methyl group, Et is an ethyl group, Bu is a butyl group, Ph is a phenyl group and the other symbols are the same as defined above.

Step M3-1

The present reaction can be carried out in the same manner as the reaction obtaining the compound [3b] from the compound [1b] and [2b].

Step M3-2

The reaction of the compound [3b'] and the compound [16] can be carried out, for example, in a solvent or without a solvent under heating. Any inert solvent which does not disturb the reaction can be used and examples of the solvent include aromatic hydrocarbons such as toluene and the like.

Step M3-3

The compound [3b'] can be converted to the compound [18] in a solvent in the presence of a methyl halide such as methyl iodide and a base such as potassium carbonate under ice-cooling to at boiling temperature of the mixture. Any inert solvent which does not disturb the reaction can be used and examples of the solvent include amides such as dimethylformamide, ketones such as methyl ethyl ketone and acetone, and acetonitrile.

Step M3-4

The reaction of the compound [18] and the compound [19] can be carried out, for example, in a solvent in the presence of a base such as sodium hydride at room temperature to under heating. Any inert solvent which does not disturb the reaction can be used and examples of the solvent include ethers such as tetrahydrofuran.

Step M3-5

Demethylation reaction and the subsequent cyclization reaction can be carried out in a solvent in the presence of boron tribromide under ice-cooling to at room temperature. Any inert solvent which does not disturb the reaction can be used and examples of the solvent include halogenated aliphatic hydrocarbons such as dichloromethane, chloroform etc.

Step M3-6

The compound [17] can be converted to the compound [21], for example, in a solvent in the presence of Grignard reagent (alkylmagnesium halide such as methylmgnesium bromide) under ice-cooling to at boiling temperature of the mixture. Any inert solvent which does not disturb the reaction can be used and examples of the solvent include ethers such as tetrahydrofuran.

Step M3-7

The cyclization reaction of the compound [21] can be carried out in a solvent or without a solvent in the presence or absence of an acid such as hydrochloric acid at room temperature to under heating. Any inert solvent which does not disturb the reaction can be used and examples of the solvent include aromatic hydrocarbons such as toluene.

Step M3-8

The compound [II-B-Ia] can be converted to the compound [II-B-Ib], for example, in a solvent in the presence of a brominating agent such as pyridinium tribromide under ice-cooling to room temperature. Any inert solvent which does not disturb the reaction can be used and examples of the solvent include halogenated aliphatic hydrocarbons such as dichloromethane and the like.

Step M3-9a

The compound [II-B-Ic] wherein $R^{43}$ is a cycloalkyl group can be prepared by treating the compound [II-B-Ib] and a boronic acid compound [22] of the formula:

$$R^{43a}-B(OR')(OR'') \qquad [22]$$

wherein $R^{43a}$ is a cycloalkyl group and the other symbols are the same as defined above, in the same manner as Step M1-5 described above.

Step M3-9b

The compound [III-B-Ic] wherein $R^{43}$ is an acetyl group can be prepared by, for example, reacting the compound [II-B-Ib] with tributyl(1-ethoxyvinyl)tin in an inert solvent such as toluene in the presence of a palladium catalyst such as tetrakis(triphenylphosphine)palladium(0) and dichlorobis(triphenylphosphine)palladium(II) at boiling point of the mixture, then, treating said reaction product with an acid such as hydrochloric acid in a solvent under ice-cooling to at room temperature. Any inert solvent which does not disturb the reaction can be used and examples of the solvent include ethers such as dioxane.

Step M3-9c

The compound [II-B-Ic] wherein $R^{43}$ is an alkenyl group can be prepared by, for example, reacting the compound [II-B-Ib] with tributyl(vinyl)tin in a solvent in the presence of a palladium catalyst such as tetrakis(triphenylphosphine)palladium(0) at room temperature to boiling point of the mixture. Any inert solvent which does not disturb the reaction can be used and examples of the solvent include ethers such as dioxane.

Step M3-9d

The compound [II-B-Ic] wherein $R^{43}$ is a cyano group can be prepared by, for example, reacting the compound [II-B-Ib] with cyanide compound such as zinc cyanide and sodium cyanide etc. in a solvent in the presence of a palladium catalyst such as tetrakis(triphenylphosphine)palladium(0) at 60° C. to boiling point of the mixture. Any inert solvent which does not disturb the reaction can be used and examples of the solvent include amides such as N,N-dimethylformamide, N,N-dimethylacetamide and 1,3-dimethylimidazolidinone.

Step M3-10 and M3-11

These reactions can be carried out in the same manner as Step M2-8 described above.

Step M3-12

The compound [II-B-Id] can be prepared by, for example, treating the compound [II-B-2] wherein $R^{44}$ is a cyano group with a strong acid such as hydrochloric acid in a solvent under heating. Any inert solvent which does not disturb the reaction can be used and examples of the solvent include ethers such as dioxane.

Step M3-13

The present reaction can be carried out in the same manner as Step 2-9 described above.

Among the intermediate compounds [IIb], a compound of the general formula [IIb-1]:

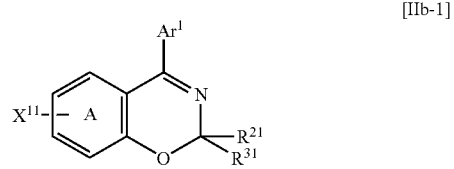

[IIb-1]

or the general formula [IIb-2]:

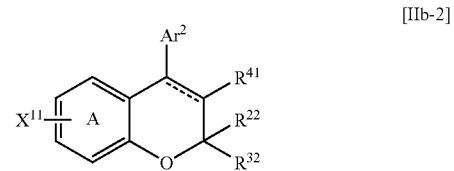

[IIb-2]

can be prepared through the reaction scheme M4 and M5 respectively.

The scheme M4 is as follows;

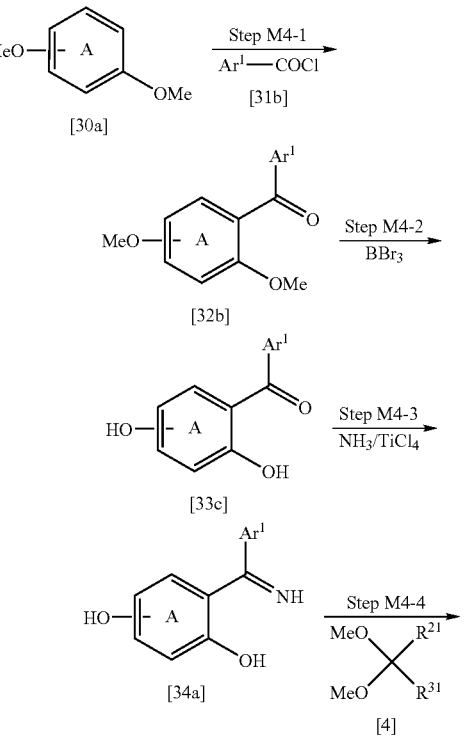

(Reaction Scheme M4)

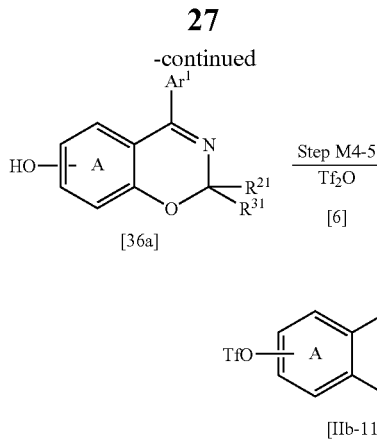

wherein Me is a methyl group, Tf is a trifluoromethanesulfonyl group and the other symbols are the same as defined above.

Step M4-1

The present reaction can be carried out in the same manner as the reaction of the compound [1b] with the compound [2b] described above.

Step M4-2

The present reaction can be carried out in the same manner as the demethylation reaction of the compound [20] in Step M3-5 described above.

Step M4-3

The present reaction can be carried out in a suitable solvent (aromatic hydrocarbons such as toluene etc.) in the presence of titanium tetrachloride.

Step M4-4

The present reaction can be carried out in the same manner as Step M1-3 described above.

Step M4-5

The present reaction can be carried out in the same manner as Step M1-4 described above.

The scheme M5 is as follows;

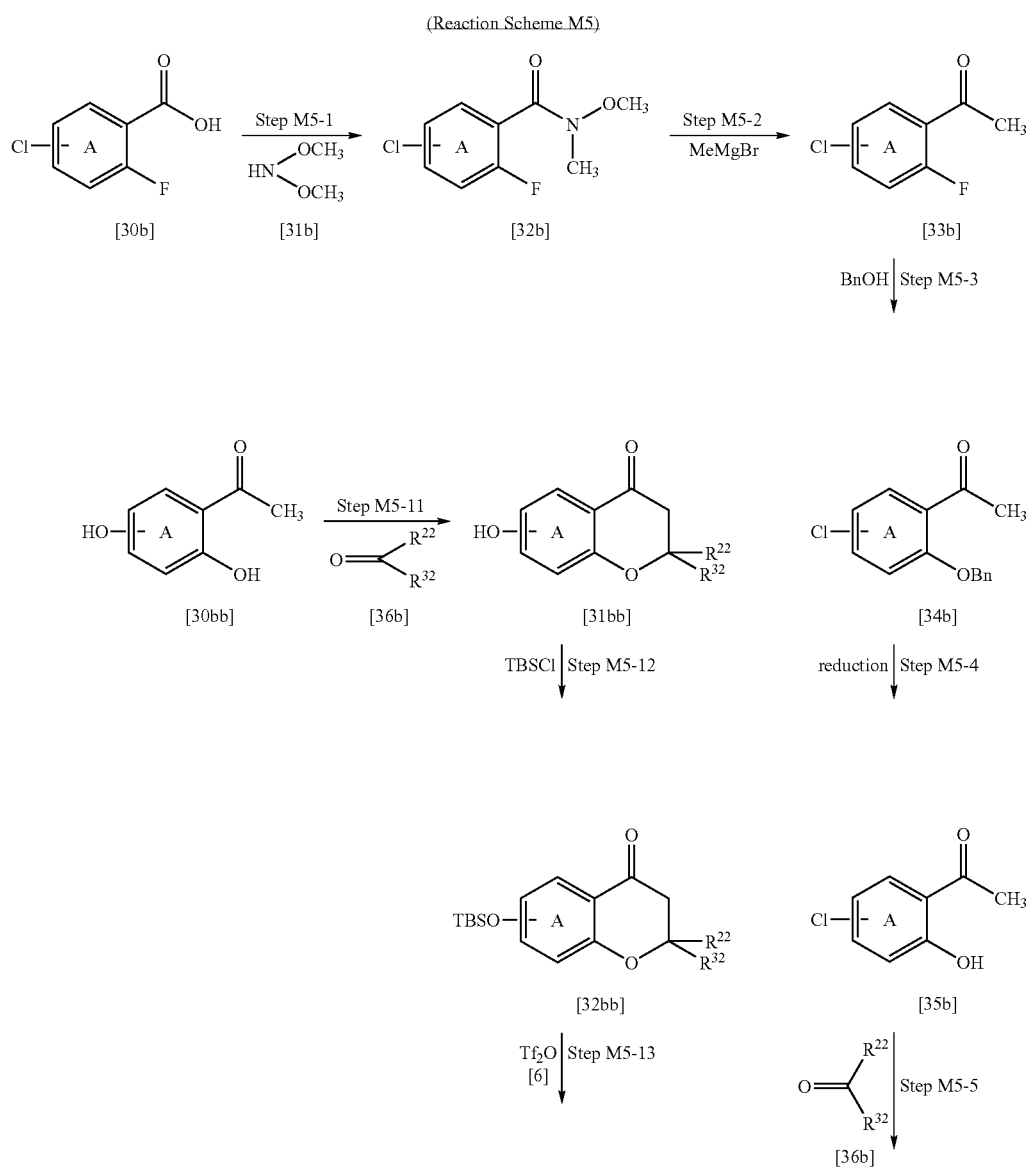

wherein the symbols are the same as defined above.

Step M5-1

The present reaction can be carried out in a suitable solvent (amides such as dimethylformamide) in the presence of a base (tertially amines such as diisopropylethylamine) and a condensing agent [O-(7-azabenzotriazol-1-yl)-N,N,N',N'-tetramethyluronium hexafluorophosphate etc.].

Step M5-2

The present reaction can be carried out in a suitable solvent (ethers such as tetrahydrofuran) in the presence of a Grignard reagent (alkylmagnesium halides such as methylmagnesium bromide etc.).

Step M5-3

The present reaction can be carried out in the same manner as Step M2-3 described above.

Step M5-4

The present reaction can be carried out in the same manner as Step M2-4 described above.

Step M5-5

The present reaction can be carried out in a suitable solvent (alcohols such as methanol etc.) in the presence of a base (pyrrolidine etc.).

Step M5-6

The present reaction can be carried out in the same manner as Step M1-4 described above.

Step M5-7

The present reaction can be carried out in the same manner as Step M1-5 described above.

Step M5-11

The present reaction can be carried out in the same manner as Step M5-5 described above. Besides, the compound [31bb] is the objective of the present step and can be also prepared through the reaction scheme below:

wherein the symbols are the same as defined above.

The reaction of the compound [41bb] with the compound [42bb], and the subsequent cyclization reaction can be carried out, for example, in a suitable solvent or without a solvent in the presence of Lewis acid (aluminum chloride etc.) and phosphoryl chloride.

Step M5-12

The present reaction can be carried out in a suitable solvent (ethers such as tetrahydrofuran etc.) in the presence of an additive (imidazole etc.).

Step M5-13

The present reaction can be carried out in the same manner as Step M1-4 described above.

Step M5-14

The present reaction can be carried out in the same manner as Step M1-5 described above.

Step M5-15

The present reaction can be carried out in the same manner as Step M1-4 described above.

The intermediate compound [IIc] can be prepared by, for example, reacting the compound [IIa] with sulfur dioxide in a suitable solvent (nitriles such as acetonitrile) in the presence of an acid (acetic acid or concentrated hydrochloric acid etc.) and nitrite (sodium nitrite), and subsequently treating the reaction product with a copper salt[cupper chloride(II) etc.].

Among the intermediate compounds (the compound [II-A] or [II-B] above) of the present invention, a compound of the general formula [ii]:

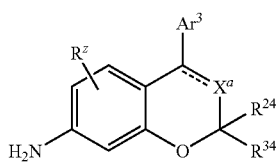

wherein $X^a$ is a group of the formula: =N— or =C(CN)—, $R^Z$ is a hydrogen atom or a halogen atom, $R^{24}$ and $R^{34}$ are alkyl groups, $Ar^3$ is a phenyl group optionally substituted with one or two substituents selected from a halogen atom and trihalogenoalkyl group, or a pharmaceutically acceptable salt thereof is useful as a synthetic intermediate of the objective compound of the present invention, and moreover has a high affinity to a mineralocorticoid receptor(MR).

For example in a binding assay using a mineralocorticoid receptor (MR) derive from rat kidney and $^3$H-aldosterone, Ki values of 5-fluoro-4-(4-fluorophenyl)-2,2-dimethyl-2H-1,3-benzoxazin-7-amine and [3-cyano-4-(4-fluorophenyl)-2,2-dimethyl-2H-chromen-7-yl]amine in $^3$H-aldosterone binding to MR are less than 10 μM.

The results of the assay described above demonstrate that said compound [ii] or a pharmaceutically acceptable salt thereof is useful as a modulator of MR activity. Further, said compound [ii] or a pharmaceutically acceptable salt thereof is useful for treating and/or preventing the diseases associated with said receptor.

In the present invention, "halogen atom" means a fluorine atom, a chlorine atom, an iodine atom or a bromine atom; "alkyl" means straight or branched alkyl having 1-8 carbon atom(s), preferably 1-6 carbon atom(s); "alkanoyl" means straight or branched alkanoyl having 1-7 carbon atom(s), preferably 2-5 carbon atom(s), "alkenyl" means straight or branched alkenyl having 2-6 carbon atoms, preferably 2-4 carbon atoms; "alkylene" means straight or branched alkylene having 1-6 carbon atom(s), preferably 1-4 carbon atom(s); "cycloalkyl" means cycloalkyl having 3-10 carbon atoms, preferably 3-8 carbon atoms; and "cycloalkenyl" means cycloalkenyl having 3-10 carbon atoms, preferably 3-8 carbon atoms.

The objective compound of the present invention obtained in each of the above-mentioned processes is exemplified in more detail by the concrete examples (Working Examples) but should not be construed to be limited thereto.

Example 1

Preparation of N-[4-(4-chlorophenyl)-2,2-dimethyl-2H-1,3-benzoxazin-7-yl]methanesulfonamide

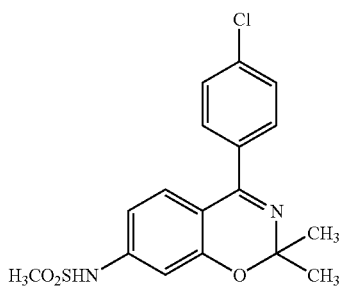

Methanesulfonyl chloride (55 μL) and pyridine (85 μL) were added dropwise to a solution of 4-(4-chlorophenyl)-2,2-dimethyl-2H-1,3-benzoxazin-7-ylamine (a compound of Reference Example 1, 101 mg) in chloroform (8 mL) and said mixture was stirred at room temperature for 2 days. The reaction solution was purified by column chromatography on silica gel (Chromatorex NH-silica gel, FUJI SILYSIA CHEMICAL LTD., Solvent: chloroform/methanol=100/0 to 90/10) and the obtained powder was suspended in diisopropyl ether. The resultant precipitates were collected by filtration and washed with diisopropyl ether to give the titled compound (112 mg) as a colorless powder.

ACPI-MS m/z: 365/367 [M+H]$^+$

Example 2

Preparation of N-[5-fluoro-4-(4-fluorophenyl)-2,2-dimethyl-2H-1,3-benzoxazin-7-yl]methanesulfonamide

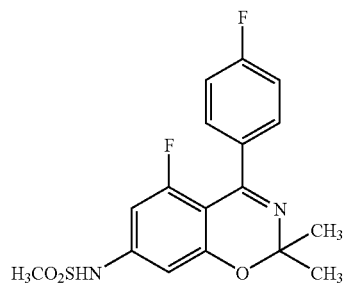

Methanesulfonylchloride (93 μL) was added dropwise to a solution of 5-fluoro-4-(4-fluorophenyl)-2,2-dimethyl-2H-1,3-benzoxazin-7-amine (a compound of Reference Example 2, 87 mg) in pyridine (2 mL), and said mixture was stirred at 40° C. overnight. The reaction mixture was concentrated in vacuo, and the residue was dissolved in chloroform. The solution was washed successively with water, 10% hydrochloric acid and brine, filtered through a column of porous diatomite [Chem Elut (trade name), Varian Inc.], and the filtrate was concentrated in vacuo. The resulted residue was purified by column chromatography on silica gel (Solvent: n-hexane/ethyl acetate=85/15 to 30/70) to give the titled compound (21 mg) as a colorless powder.

ACPI-MS m/z: 367 [M+H]$^+$

Example 3

Preparation of N-[5-fluoro-4-(4-fluorophenyl)-2,2-dimethyl-2H-1,3-benzoxazin-7-yl]methanesulfonamide

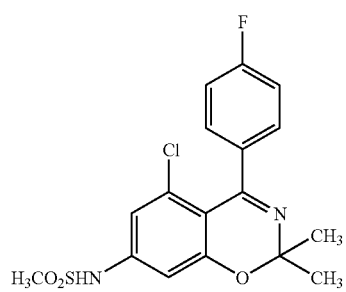

Methanesulfonyl chloride (8.5 μL) was added dropwise to a solution of 5-chloroo-4-(4-fluorophenyl)-2,2-dimethyl-2H-1,3-benzoxazin-7-amine (a compound of Reference Example 3, 7.5 mg) in pyridine (1 mL), and said mixture was stirred at 30° C. for 2 days. The reaction solution was diluted with chloroform and washed successively with water, a saturated aqueous solution of sodium bicarbonate and brine. The

Example 4

Preparation of N-[2,2-diethyl-4-(4-fluorophenyl)-2H-1,3-benzoxazin-7-yl]methanesulfonamide

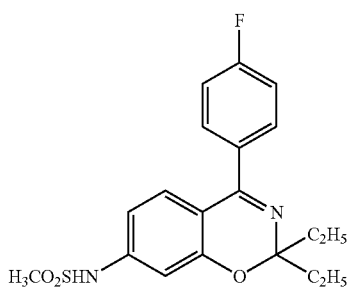

Methanesulfonyl chloride (63 μL) and pyridine (131 μL) were added dropwise to a solution of 2,2-diethyl-4-(4-fluorophenyl)-2H-1,3-benzoxazin-7-amine (a compound of Reference Example 4, 81 mg) in chloroform (5 mL), and the mixture was stirred at 40° C. overnight. The reaction mixture was purified by column chromatography on NH-silica gel (Chromatorex NH-silica gel, Solvent: chloroform/methanol=100/0 to 90/10), and the resultant powder was suspended in diisopropyl ether. The resultant precipitates were collected by filtration and washed with hexane-diisopropyl ether to give the titled compound (69 mg) as a colorless powder.

APCI-MS m/z: 377 $[M+H]^+$

Example 5

Preparation of N-[4-(4-fluorophenyl)-2,2-dimethyl-2H-chromen-7-yl]methanesulfonamide

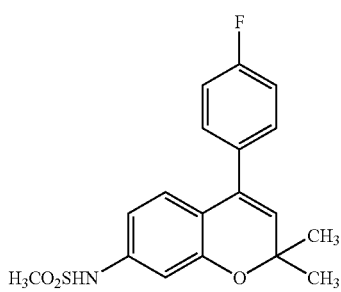

Under ice-cooling, pyridine (90 μL) and methanesulfonyl chloride (60 μL) were added dropwise to a solution of [4-(4-fluorophenyl)-2,2-dimethyl-2H-chromen-7-yl]amine (a compound of Reference Example 5(5), 100 mg) in chloroform (3 mL), and the mixture was stirred at room temperature for 2 hours. The reaction mixture was purified by column chromatography on NH-silica gel (Chromatorex NH-silica gel, Solvent: chloroform/methanol=100/0 to 90/10) to give the titled compound (123 mg) as a colorless powder.

ACPI-MS m/z: 348 $[M+H]^+$

Example 6

Preparation of N-[4-(4-fluorophenyl)-2,2,3-trimethyl-2H-chromen-7-yl]methanesulfonamide

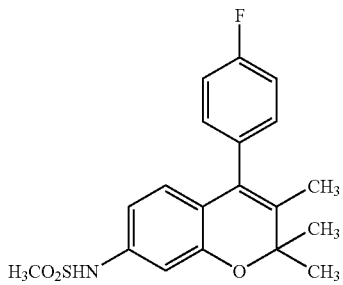

Under ice-cooling, pyridine (55 μL) and Methanesulfonyl chloride (35 μL) were added dropwise to a solution of [4-(4-fluorophenyl)-2,2,3-trimethyl-2H-chromen-7-yl]amine (a compound of Reference Example 6(5), 64 mg) in chloroform (3 mL), and the mixture was stirred at room temperature for 2 hours. The reaction mixture was purified by column chromatography on NH-silica gel (Chromatorex NH-silica gel, Solvent: chloroform/methanol=100/0 to 90/10) to give the titled compound (76 mg) as a colorless powder.

ACPI-MS m/z: 362 $[M+H]^+$

Example 7

Preparation of N-[3-fluoro-4-(4-fluorophenyl)-2,2-dimethyl-2H-chromen-7-yl]methanesulfonamide

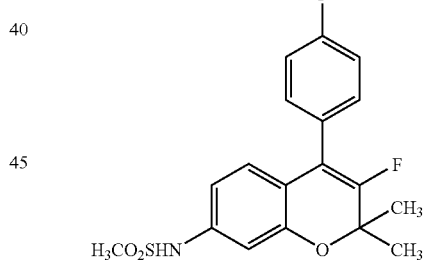

Under ice-cooling, pyridine (4 mL) and Methanesulfonyl chloride (60 μL) were added dropwise to a solution of [3-fluoro-4-(4-fluorophenyl)-2,2-dimethyl-2H-chromen-7-yl]amine (a compound of Reference Example 7(7), 105 mg) in pyridine (4 mL) and the mixture was stirred at room temperature for 2 hours. The reaction solution was concentrated in vacuo, the residue was diluted with ethyl acetate, and the solution was washed successively with a saturated aqueous solution of citric acid, water, a saturated aqueous solution of sodium bicarbonate and brine. The organic layer was filtered through a column of porous diatomite (Chem Elut), and the filtrate was concentrated in vacuo. The resultant residue was purified by column chromatography on NH-silica gel (Chromatorex NH-silica gel, Solvent: chloroform/methanol=100/0 to 90/10) to give the titled compound (105 mg) as a colorless powder.

ACPI-MS m/z: 366 $[M+H]^+$

Example 8

Preparation of N-[4-(4-fluorophenyl)-2,2-dimethyl-3,4-dihydro-2H-chromen-7-yl]methanesulfonamide

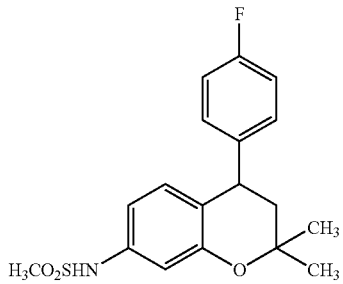

10% Palladium-carbon (water-content ca.50%, 20 mg) was added to a solution of N-[4-(4-fluorophenyl)-2,2-dimethyl-2H-chromen-7-yl]methanesulfonamide (a compound obtained in Example 5, 20 mg) in ethanol (4 mL), and the mixture was stirred under atmospheric pressure of hydrogen at room temperature for 20 hours. The reaction solution was filtered through Celite, and the filtrate was concentrated in vacuo. The resultant residue was purified by column chromatography on silica gel (Solvent: n-hexane/ethyl acetate=95/5 to 70/30) to give the titled compound (20 mg) as a colorless powder.

ESI-MS m/z: 348 [M−H]−

Example 9

Preparation of N-[(3,4-cis)-4-(4-fluorophenyl)-2,2,3-trimethyl-3,4-dihydro-2H-chromen-7-yl]methanesulfonamide

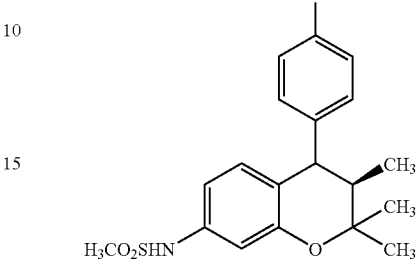

N-[4-(4-fluorophenyl)-2,2,3-trimethyl-2H-chromen-7-yl]methanesulfonamide (a compound obtained in Example 6, 20 mg) was treated in the same manner as Example 8 to give the titled compound (20 mg) as a colorless viscous oil.

ESI-MS m/z: 362 [M−H]−

Examples 10-27

Corresponding starting compounds were treated in the same manner as Example 1 or 2 to give the compounds in Tables 1-4 below.

TABLE 1

| Example | Structure | Physicochemical properties |
|---|---|---|
| 10 | 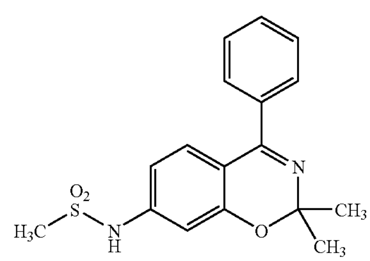 | colorless powder<br>MS(APCI)m/z: 331 [M + H]+ |
| 11 | 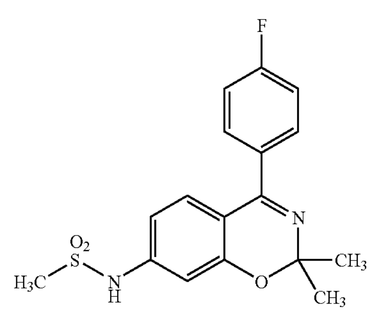 | colorless powder<br>MS(APCI)m/z: 349 [M + H]+ |

TABLE 1-continued

| Example | Structure | Physicochemical properties |
|---|---|---|
| 12 | 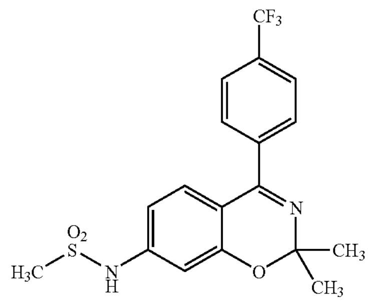 | colorless powder<br>MS(APCI)m/z: 399 [M + H]+ |
| 13 | 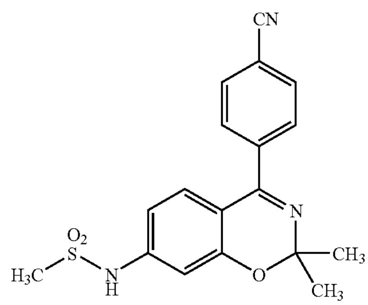 | pale yellow powder<br>MS(APCI)m/z: 356 [M + H]+ |
| 14 | 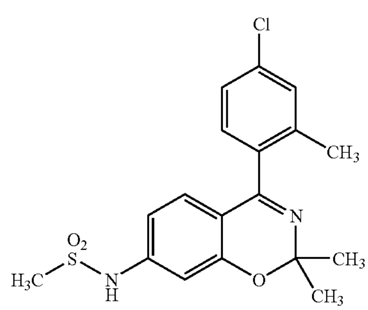 | colorless powder<br>MS(APCI)m/z: 379/381 [M + H]+ |

TABLE 2

| Example | Structure | Physicochemical properties |
|---|---|---|
| 15 | 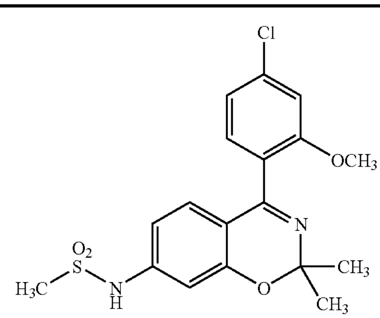 | pale yellow viscous oil<br>MS(APCI)m/z: 395/397 [M + H]+ |

TABLE 2-continued

| Example | Structure | Physicochemical properties |
|---|---|---|
| 16 | 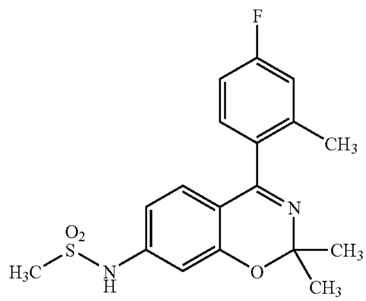 | colorless powder<br>MS(APCI)m/z: 363 [M + H]+ |
| 17 | 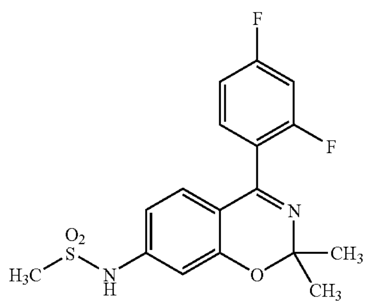 | colorless powder<br>MS(APCI)m/z: 367 [M + H]+ |
| 18 | 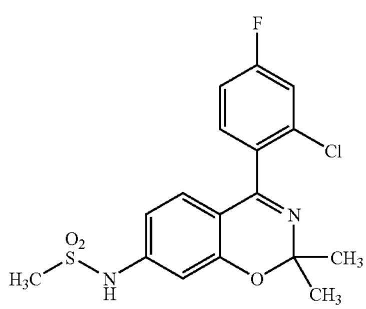 | pale yellow powder<br>MS(APCI)m/z: 383/385 [M + H]+ |
| 19 | 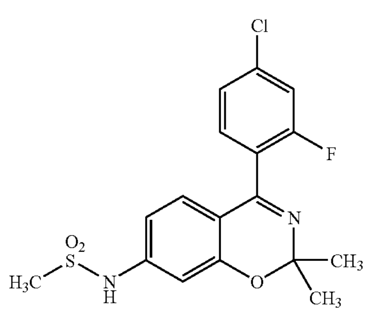 | colorless powder<br>MS(APCI)m/z: 383/385 [M + H]+ |

TABLE 3
| Example | Structure | Physicochemical properties |
|---------|-----------|----------------------------|
| 20 | 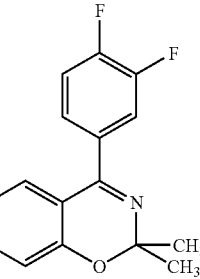 | colorless powder<br>MS(APCI)m/z: 367 [M + H]$^+$ |
| 21 | 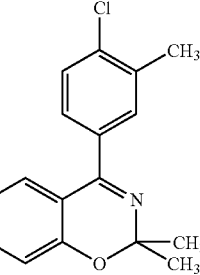 | colorless powder<br>MS(APCI)m/z: 379/381<br>[M + H]$^+$ |
| 22 | 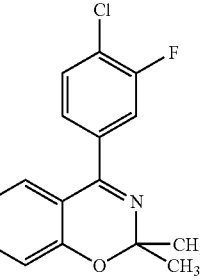 | pale yellow powder<br>MS(APCI)m/z: 383/385<br>[M + H]$^+$ |
| 23 | 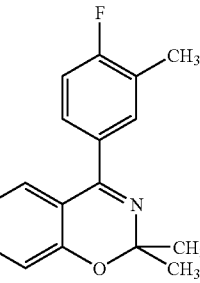 | pale yellow powder<br>MS(APCI)m/z: 363 [M + H]$^+$ |
| 24 | 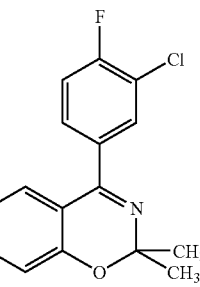 | colorless powder<br>MS(APCI)m/z: 383/385<br>[M + H]$^+$ |

TABLE 4

| Example | Structure | Physicochemical properties |
| --- | --- | --- |
| 25 | 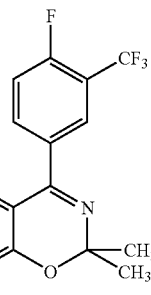 | colorless powder<br>MS(APCI)m/z: 417 [M + H]⁺ |
| 26 | 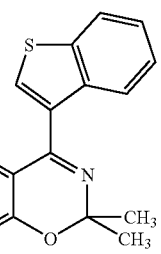 | yellow powder<br>MS(APCI)m/z: 387 [M + H]⁺ |
| 27 | 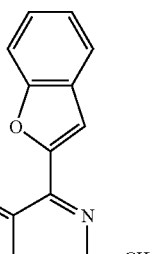 | colorless powder<br>MS(APCI)m/z: 371 [M + H]⁺ |

Examples 28-29

Corresponding starting compounds were treated in the same manner as Example 2 to give the compounds in Tables 5 below.

TABLE 5

| Example | Structure | Physicochemical properties |
| --- | --- | --- |
| 28 | 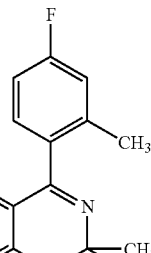 | colorless powder<br>MS(APCI)m/z: 381 [M + H]⁺ |

TABLE 5-continued

| Example | Structure | Physicochemical properties |
|---|---|---|
| 29 | 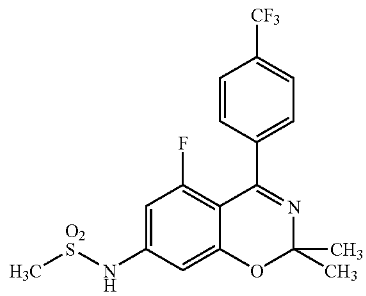 | pale yellow powder<br>MS(APCI)m/z: 417 [M + H]⁺ |

Examples 30-33

Corresponding starting compounds were treated in the same manner as Example 4 to give the compounds in Tables 6 below.

TABLE 6

| Example | Structure | Physicochemical properties |
|---|---|---|
| 30 | 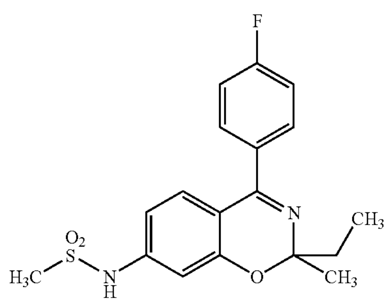 | colorless powder<br>MS(APCI)m/z: 363 [M + H]⁺ |
| 31 | 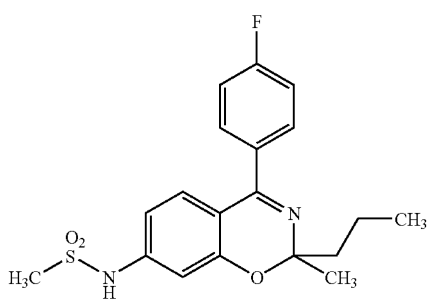 | colorless powder<br>MS(APCI)m/z: 377 [M + H]⁺ |
| 32 | 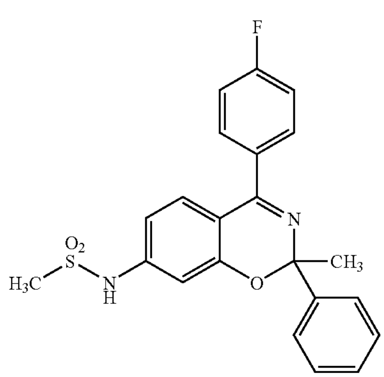 | pale yellow powder<br>MS(APCI)m/z: 411 [M + H]⁺ |

TABLE 6-continued

| Example | Structure | Physicochemical properties |
|---|---|---|
| 33 | 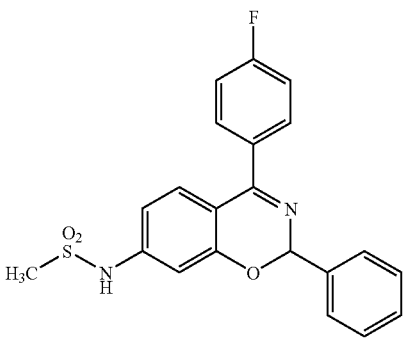 | pale yellow viscous oil<br>MS(APCI)m/z: 397 [M + H]⁺ |

Examples 34-38

Corresponding starting compounds were treated in the same manner as Example 5 or 7 to give the compounds in Tables 7 below.

TABLE 7

| Example | Structure | Physicochemical properties |
|---|---|---|
| 34 | 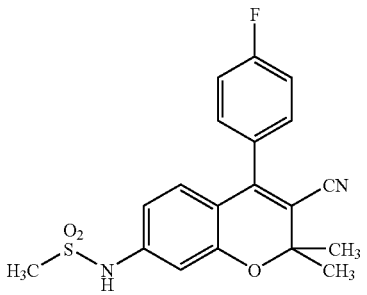 | colorless powder<br>MS(ESI)m/z: 371 [M − H]⁻ |
| 35 | 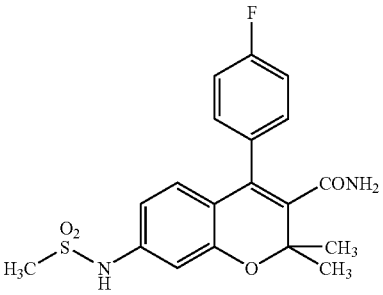 | pale brown powder<br>MS(APCI)m/z: 391 [M + H]⁺ |
| 36 | 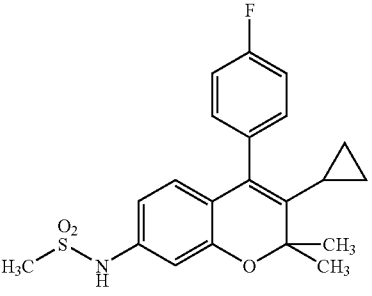 | pale brown powder<br>MS(APCI)m/z: 388 [M + H]⁺ |

TABLE 7-continued

| Example | Structure | Physicochemical properties |
|---|---|---|
| 37 | 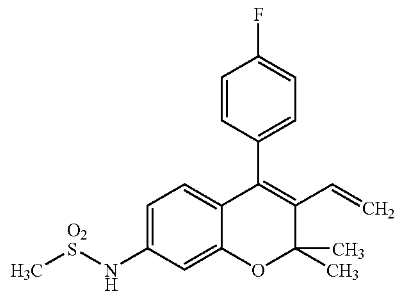 | pale yellow powder<br>MS(APCI)m/z: 374 [M + H]+ |
| 38 | 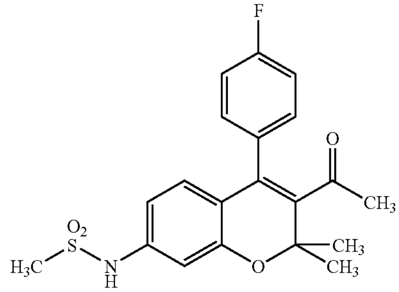 | pale brown powder<br>MS(APCI)m/z: 390 [M + H]+ |

Example 39

Preparation of N-[4-(4-chlorophenyl)-2,2-dimethyl-2H-chromen-7-yl]methanesulfonamide

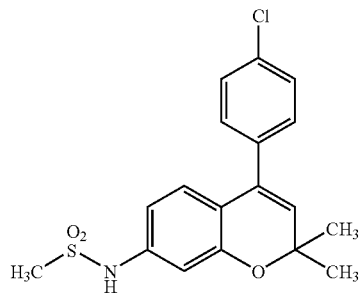

A mixture of [4-(4-chlorophenyl)-2,2-dimethyl-2H-chromen-7-yl]trifluoromethanesulfonate (100 mg), mesylamine (27 mg), cesium carbonate (117 mg), tris(dibenzylideneacetone)dipalladium(10 mg, 10% wt), 9,9-dimethyl-4,5-bis(diphenylphosphino)-9H-xanthen (Xantphos, 20 mg, 20% wt) and dioxane (2 mL) was heated under reflux for 10 hours. The reaction mixture was filtered, the filtrate was concentrated in vacuo, and the residue was purified by column chromatography on silica gel (petroleum ether/ethyl acetate=100/1) to give the titled compound (50 mg) as a colorless powder.

ACPI-MS m/z: 364/366 [M+H]+

Example 40-48

Corresponding starting compounds were treated in the same manner as Example 39 to give the compounds in Tables 8 and 9 below.

TABLE 8

| Example | Structure | Physicochemical properties |
|---|---|---|
| 40 | 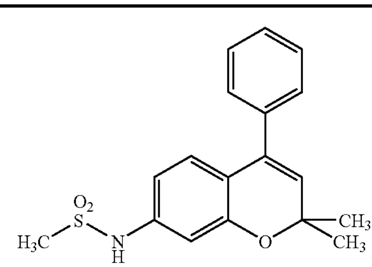 | colorless powder<br>MS(APCI)m/z: 300 [M + H]+ |

TABLE 8-continued
| Example | Structure | Physicochemical properties |
|---|---|---|
| 41 | 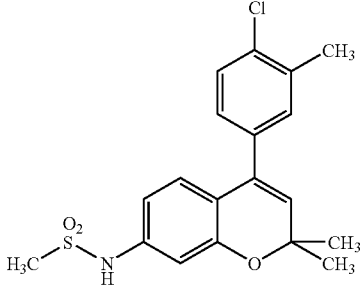 | colorless powder<br>MS(APCI)m/z: 378/380<br>[M + H]+ |
| 42 | 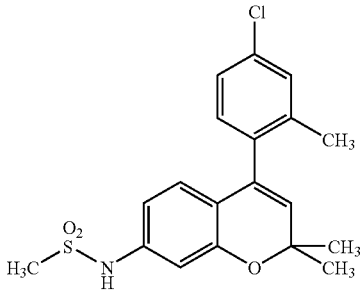 | yellow powder<br>MS(APCI)m/z: 378/380<br>[M + H]+ |
| 43 | 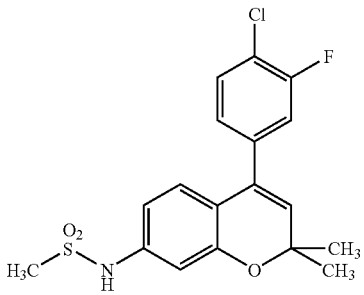 | colorless powder<br>MS(APCI)m/z: 382/384<br>[M + H]+ |
| 44 | 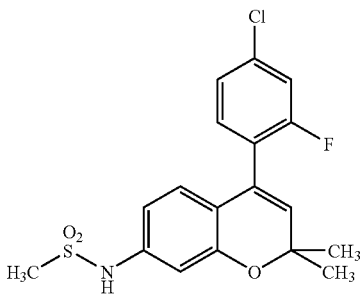 | pale yellow powder<br>MS(APCI)m/z: 382/384<br>[M + H]+ |

TABLE 9
| Example | Structure | Physicochemical properties |
|---------|-----------|----------------------------|
| 45 | 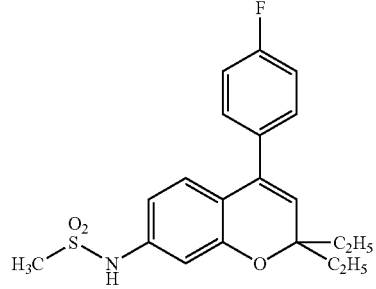 | colorless powder<br>MS(APCI)m/z: 376 [M + H]$^+$ |
| 46 | 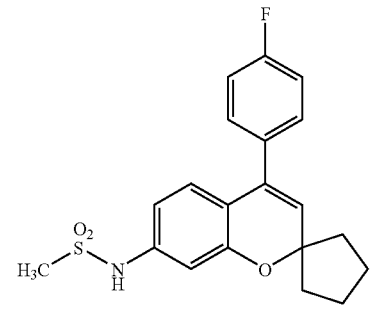 | colorless powder<br>MS(APCI)m/z: 374 [M + H]$^+$ |
| 47 | 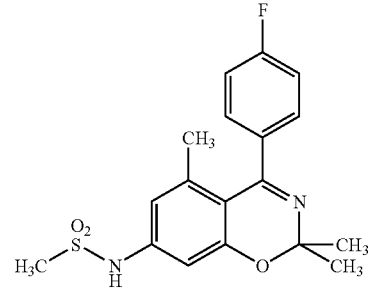 | colorless powder<br>MS(APCI)m/z: 363 [M + H]$^+$ |
| 48 | 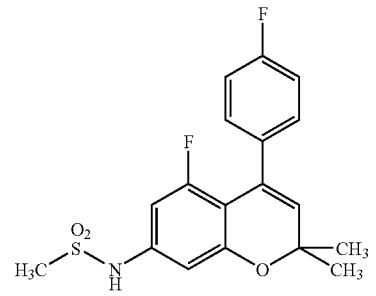 | colorless powder<br>MS(APCI)m/z: 366 [M + H]$^+$ |

Example 49

Preparation of N-[2,2-diethyl-4-(4-fluorophenyl)-2H-1,3-benzoxazin-7-yl]methanesulfonamide (the same as the objective compound in Example 11)

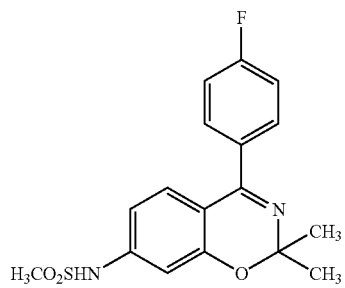

Methanesulfonylchloride (2.5 g) were added dropwise to a solution of 2,2-diethyl-4-(4-fluorophenyl)-2H-1,3-benzoxazin-7-yl]amine (a compound of Reference Example 38(3), 2.0 g) and dimethylaminopyridine (a catalytic amount) in pyridine (30 ml) at room temperature under stirring, and the mixture was stirred at the same temperature overnight. The reaction mixture was poured into water (100 mL), the mixture was extracted with dichloromethane (50 mL×3) and the combined organic layer was concentrated in vacuo. The residue was dissolved with ethyl acetate (50 mL), and the solution was washed with saturated brine, dried over sodium sulfate and concentrated in vacuo. The resulted crude product was recrystallized from ethyl acetate/hexane (1/1) to give the titled compound (2.1 g) as a colorless powder.

Example 50

(1) Preparation of N-[3-bromo-2,2-dimethyl-4-phenyl-2H-chromen-7-yl]methane sulfonamide

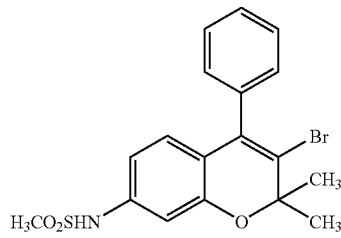

Pyridinium bromide perbromide (419 mg) was added to a solution of the objective compound of Example 40 (430 mg) in dichloromethane (50 mL), and the mixture was stirred at room temperature for 30 minutes. After the addition of water to the reaction solution, the organic layer was separated, dried over sodium sulfate and concentrated in vacuo. The residue was purified by column chromatography on silica gel (Solvent: petroleum ether/ethyl acetate) to give the titled compound (280 mg) as a yellow powder.

(2) Preparation of N-[3-cyano-2,2-dimethyl-4-phenyl-2H-chromen-7-yl]methane sulfonamide

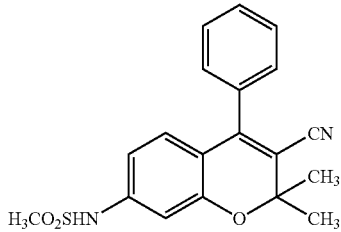

Copper cyanide (138 mg) was added to a solution of the compound obtained in (1) above (520 mg) in 1-methyl-2-pyrrolidone (6 mL), and the mixture was stirred at 200° C. in a microwave reaction apparatus for 30 minutes. Brine was added to the reaction mixture and the mixture was extracted with dichloromethane (20 mL×3). The combined organic layer was washed successively with water (20 mL×3) and brine, dried and concentrated in vacuo. The residue was purified by column chromatography on silica gel (Solvent: petroleum ether/ethyl acetate) to give the titled compound (158 mg) as a pale yellow powder.

ACPI-MS m/z: 355 [M+H]$^+$

Examples 51-53

Corresponding starting compounds were treated in the same manner as Example 50 to give the compounds in Tables 10 below.

TABLE 10

| Example | Structure | Physicochemical properties |
|---|---|---|
| 51 | (4-chlorophenyl derivative) | Colorless powder<br>MS(ESI)m/z: 387/389 [M − H]$^-$ |

TABLE 10-continued

| Example | Structure | Physicochemical properties |
|---|---|---|
| 52 | 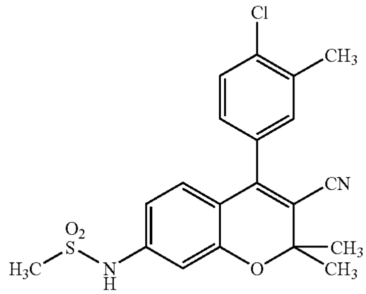 | Colorless powder<br>MS(ESI)m/z: 401/403 [M − H]⁻ |
| 53 | 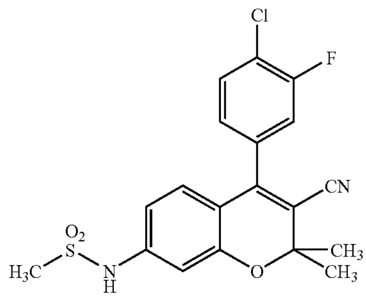 | Pale yellow powder<br>MS(ESI)m/z: 405/407 [M − H]⁻ |

Example 54

(1) Preparation of N-[3-bromo-2,2-diethyl-4-(4-fluorophenyl)-2H-chromen-7-yl]methanesulfonamide

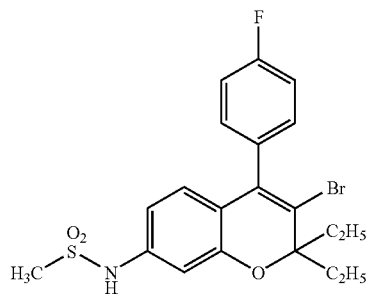

Pyridinium bromide perbromide (379 mg) was added to a solution of the objective compound of Example 45 (450 mg) in dichloromethane (50 mL) under cooling at −15° C., the mixture was gradually warmed to room temperature and stirred at the same temperature for 15 minutes. After addition of an aqueous solution of sodium bicarbonate (30 mL) to the reaction solution, the mixture was extracted with dichloromethane (40 mL×3). The combined organic layer was dried over sodium sulfate and filtered. The filtrate was concentrated in vacuo, and the residue was purified by column chromatography on silica gel (petroleum ether/ethyl acetate=17/1) to give the titled compound (300 mg) as a colorless powder.

(2) Preparation of N-[3-cyano-2,2-diethyl-4-(4-fluorophenyl)-2H-chromen-7-yl]methanesulfonamide

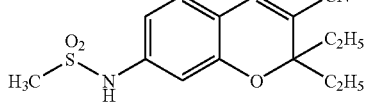

The compound obtained in (1) described above (220 mg) was treated in the same manner as Example 50(2) to give the titled compound (56 mg) as a colorless powder.
ACPI-MS m/z: 402 [M+H]⁺

Example 55

(1) Preparation of N-[3-bromo-4-(4-fluorophenyl)spiro[chromen-2',1'-cyclopentan]-7-yl]methanesulfonamide

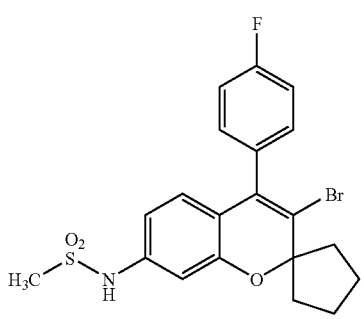

The objective compound of Example 46 (450 mg) was treated in the same manner as Example 56(1) to give the titled compound (300 mg) as a colorless powder.

(2) Preparation of N-[3-cyano-4-(4-fluorophenyl) spiro[chromen-2',1'-cyclopentan]-7-yl]methanesulfonamide [compound (a)] and N-[3-(1-cyclopenten-1-yl)-4-(4-fluorophenyl)-2-oxochromen-7-yl] methanesulfonamide [compound (b)]

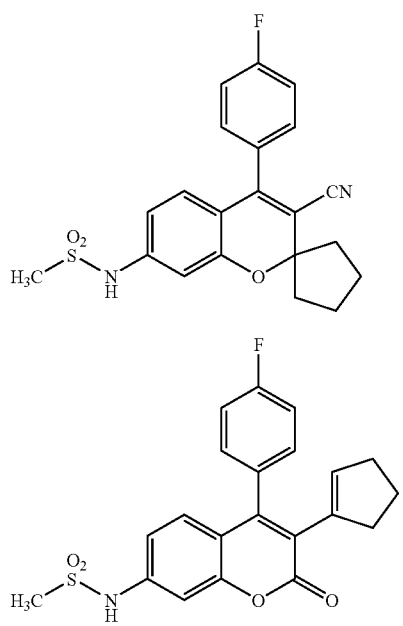

The compound obtained in (1) described above (220 mg) was treated in the same manner as Example 50(2) to give the titled compound (a) (88 mg) as a pale yellow powder, and the titled compound (b) (75 mg) as a colorless powder.
the compound (a): ESI-MS m/z: 397 [M−H]⁻
the compound (b): APCI-MS m/z: 400 [M+H]⁺

Example 56

(1) Preparation of N-[4-(5-chloropyridin-2-yl)-2,2-dimethyl-2H-chromen-7-yl]methanesulfonamide

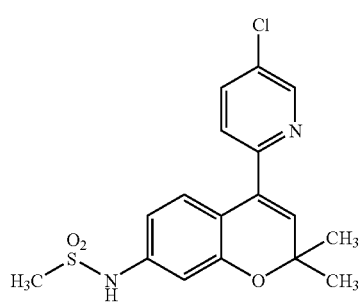

A mixture of the objective compound of Reference Example 42(4) (800 mg), mesylamine (272 mg), cesium carbonate (1.3 g), tris(dibenzylideneacetone)dipalladium(0) (56 mg), biphenyl-2-yl-di(tert-butyl)phosphane (112 mg) and dioxane (4 mL) was heated under reflux under nitrogen atmosphere overnight. The reaction mixture was filtered, and the filtrate was concentrated in vacuo. The residue was purified by column chromatography on silica gel (petroleum ether/ethyl acetate=17/1) to give the titled compound (520 mg) as a yellow powder.

(2) Preparation of N-[3-bromo-4-(5-chloropyridin-2-yl)-2,2-dimethyl-2H-chromen-7-yl]methanesulfonamide

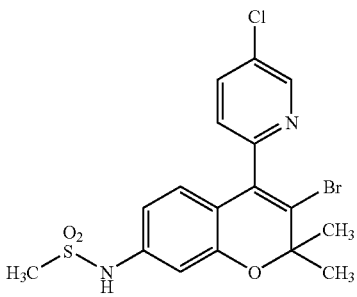

The compound obtained in (1) described above (520 mg) was treated in the same manner as Example 50(1) to give the titled compound (500 mg) as a yellow powder.

(3) Preparation of N-[4-(5-chloropyridin-2-yl)-3-cyano-2,2-dimethyl-2H-chromen-7-yl]methanesulfonamide

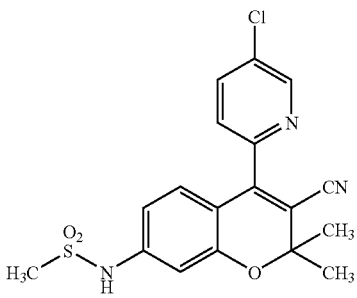

The compound obtained in (2) described above (400 mg) was treated in the same manner as Example 50(2) to give the titled compound (76 mg) as a pale yellow powder.
ACPI-MS m/z: 390/392 [M+H]⁺

Example 57

(1) Preparation of N-[2,2-dimethyl-4-(5-fluoropyridin-2-yl)-2H-chromen-7-yl]methanesulfonamide

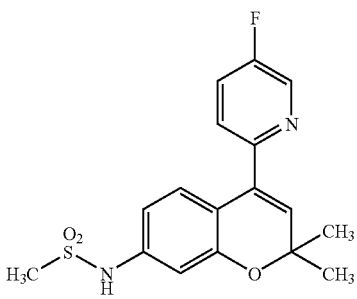

The objective compound of Reference Example 43(4) (800 mg) was treated in the same manner as Example 56(1) to give the titled compound (480 mg) as a pale yellow powder.

(2) Preparation of N-[3-bromo-4-(5-fluoropyridin-2-yl)-2,2-dimethyl-2H-chromen-7-yl]methanesulfonamide

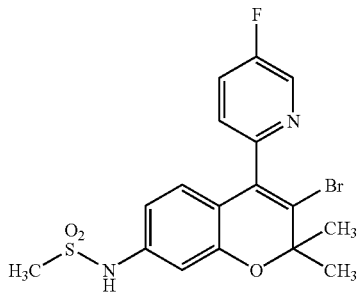

The compound obtained in (1) described above (480 mg) was treated in the same manner as Example 50(1) to give the titled compound (500 mg) as a brown powder.

(3) Preparation of N-[4-(5-fluoropyridin-2-yl)-3-cyano-2,2-dimethyl-2H-chromen-7-yl]methanesulfonamide

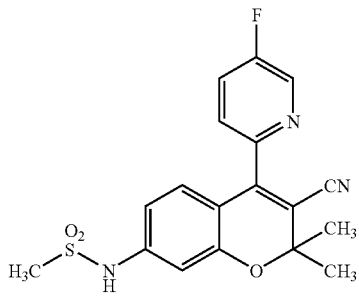

The compound obtained in (2) described above (200 mg) was treated in the same manner as Example 50(2) to give the titled compound (54 mg) as a pale yellow powder.
ACPI-MS m/z: 374 [M+H]$^+$ Example 58

(1) Preparation of N-[4-(4-fluorophenyl)-2,2,5-trimethyl-2H-chromen-7-yl]methanesulfonamide

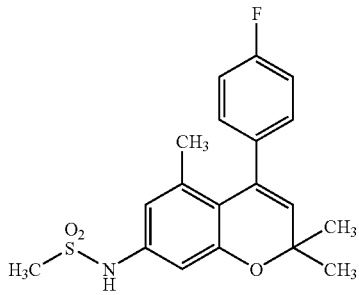

The objective compound of Reference Example 44(5) (2.5 g) was treated in the same manner as Example 56(1) to give the titled compound (1.5 g) as a colorless powder.
APCI-MS m/z: 362 [M+H]$^+$ (2) Preparation of N-[3-bromo-4-(4-fluorophenyl)-2,2,5-trimethyl-2H-chromen-7-yl]methanesulfonamide

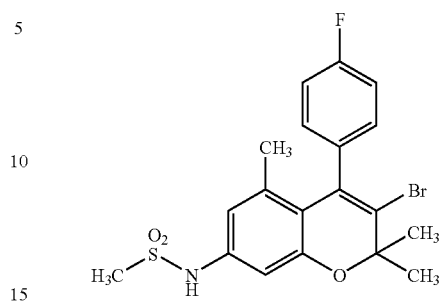

The compound obtained in (1) described above (580 mg) was treated in the same manner as Example 50(1) to give the titled compound (480 mg) as a crude product, which was used in the next step without further purification.

(3) Preparation of N-[3-cyano-4-(4-fluorophenyl)-2,2,5-trimethyl-2H-chromen-7-yl]methanesulfonamide

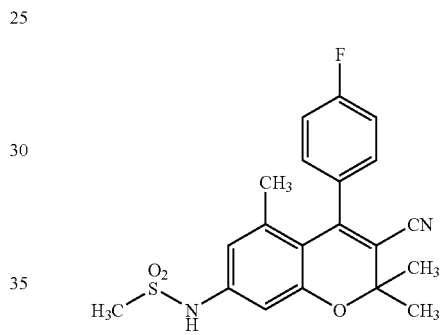

The compound obtained in (2) described above (480 mg) was treated in the same manner as Example 50(2) to give the titled compound (128 mg) as a colorless powder.
ESI-MS m/z: 385 [M−H]$^−$ Example 59

Preparation of N-[3-fluoro-4-(4-fluorophenyl)-2,2,5-trimethyl-2H-chromen-7-yl]methanesulfonamide (compound a) and N-[6-fluoro-4-(4-fluorophenyl)-2,2,5-trimethyl-2H-chromen-7-yl]methanesulfonamide (compound b)

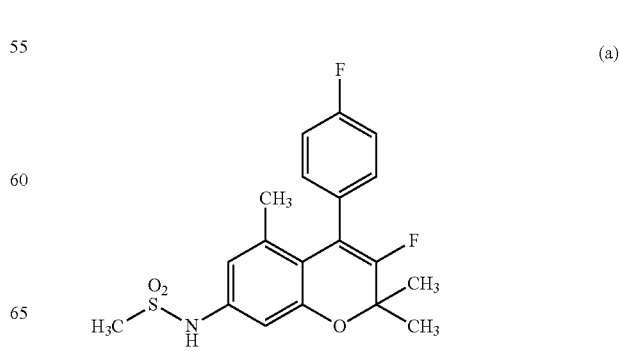

-continued (b)

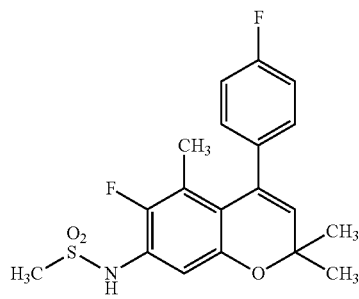

1-Fluoropyridinium trifluoromethanesulfonate (205 mg) was added to a solution of the objective compound of Example 58(1) (300 mg) in dichloroethane (30 mL), and the mixture was heated under reflux overnight. After addition of water (15 ml) to the reaction solution, the organic layer was separated, dried over sodium sulfate and concentrated in vacuo. The residue was purified with a supercritical fluid chromatography (SFC) to give the titled compound a (38 mg, a colorless powder) and the titled compound b (4 mg, a colorless powder).

the compound a: ESI-MS m/z: 378 [M−H]⁻
the compound b: APCI-MS m/z: 380 [M+H]⁺

Example 60

(1) Preparation of N,2,2-trimethyl-4-(4-fluorophenyl)-2H-chromen-7-sulfonamide

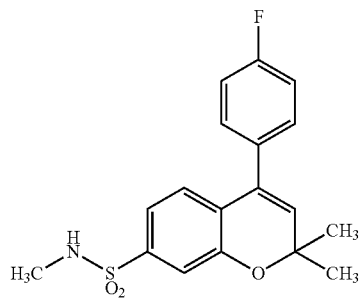

Under ice-cooling, triethylamine (3.94 mL), dimethylaminopyridine (138 mg) and methylamine hydrochloride (571 mg) were added to a solution of the objective compound of Reference Example 38(6) (2.0 g) in dichloromethane (20 mL), and the mixture was stirred at room temperature overnight. The reaction solution was poured into water (40 mL), and the mixture was extracted with dichloromethane (30 mL×3). The combined organic layer was dried over sodium sulfate, concentrated in vacuo, and the residue was purified by column chromatography on silica gel (petroleum ether/ethyl acetate=10/1) to give the titled compound (990 mg) as a colorless powder.

APCI-MS m/z: 348 [M+H]⁺

(2) Preparation of 3-bromo-N,2,2-trimethyl-4-(4-fluorophenyl)-2H-chromen-7-sulfonamide

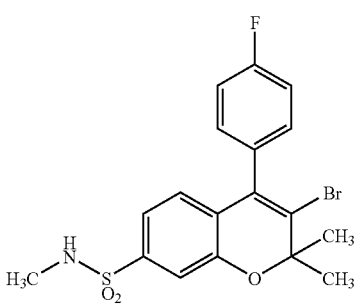

The compound obtained in (1) described above (300 mg) was treated in the same manner as Example 50(1) to give the titled compound (350 mg), which was used in the next step without further purification.

(3) Preparation of 3-cyano-N,2,2-trimethyl-4-(4-fluorophenyl)-2H-chromen-7-sulfonamide

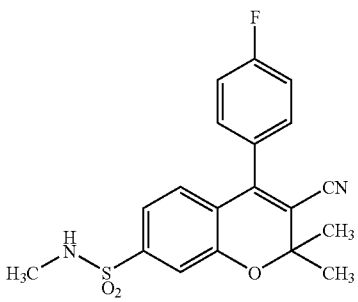

The compound obtained in (1) described above (350 mg) was treated in the same manner as Example 50(2) to give the titled compound (260 mg) as a yellow powder.
ESI-MS m/z: 371 [M−H]⁻

Example 61

Preparation of N,2,2-trimethyl-4-(4-fluorophenyl)-2H-1,3-benzoxazin-7-sulfonamide

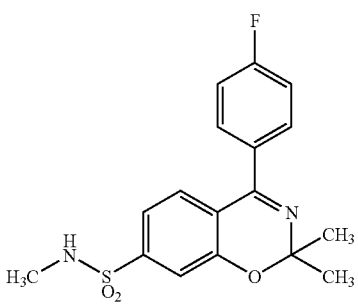

A solution of the objective compound of Reference Example 45 (400 mg) in dichloromethane (10 mL) was added dropwise to a solution of methylamine hydrochloride (227 mg) and triethylamine (465 mg) in dichloromethane (10 mL) at 0° C. under stirring, and the mixture was stirred at room temperature overnight. The reaction mixture was washed

Example 62

Preparation of N-[4-(4-trifluoromethylphenyl)-2,2-dimethyl-2H-chromen-7-yl]methanesulfonamide

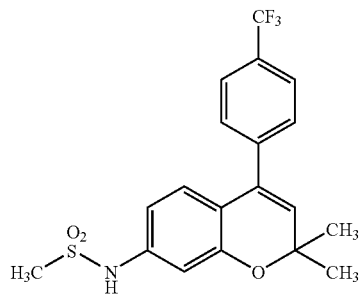

The objective compound of Reference Example 53 (400 mg) was treated in the same manner as Example 56(1) to give the titled compound (136 mg) as a pale yellow powder.
ACPI-MS m/z: 398 [M+H]$^+$

Example 63

Preparation of N-[5-chloro-4-(4-fluorophenyl)-2,2-dimethyl-2H-chromen-7-yl]methanesulfonamide

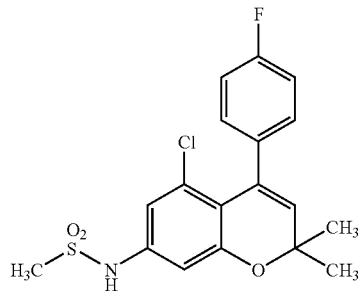

The objective compound of Reference Example 54 (1.6 g) was treated in the same manner as Example 56(1) to give the titled compound (1.0 g) as a yellow powder.
ACPI-MS m/z: 382/384 [M+H]$^+$

Example 64

Preparation of N-[5-chloro-4-(4-fluorophenyl)-2,2-dimethyl-2H-chromen-7-yl]methanesulfonamide

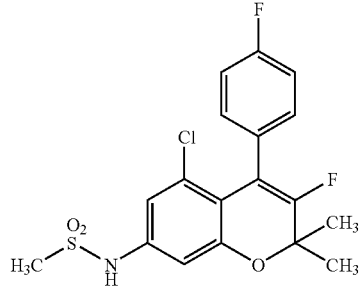

The objective compound of Example 63 (400 mg) was treated in the same manner as Example 59(1) to give the titled compound (106 mg) as a colorless powder.
ESI-MS m/z: 398/400 [M−H]$^-$

Example 65

Preparation of N-[5-chloro-4-(2,4-difluorophenyl)-2,2-dimethyl-2H-1,3-benzoxazin-7-yl]-methanesulfonamide

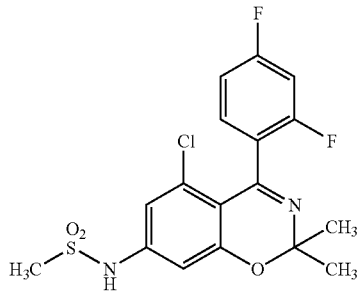

The objective compound of Reference Example 56 (380 mg) and mesylamine (102 mg) were treated in the same manner as Example 39 to give the titled compound (60 mg) as a colorless powder.
ACPI-MS m/z: 401/403 [M+H]$^+$

Example 66

Preparation of N-[2,2-diethyl-4-(2,4-difluorophenyl)-2H-1,3-benzoxazin-7-yl]-methanesulfonamide

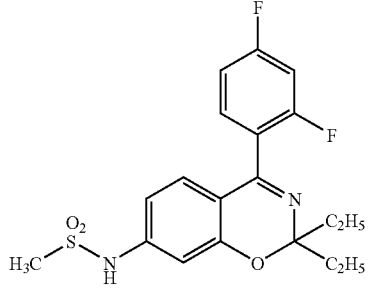

The objective compound of Reference Example 57 (400 mg) and methanesulfonyl chloride (360 mg) were treated in the same manner as Example 49 to give the titled compound (170 mg) as a yellow powder.
ACPI-MS m/z: 395 [M+H]$^+$

Example 67

Preparation of N-[5-chloro-2,2-diethyl-4-(4-fluorophenyl)-2H-1,3-benzoxazin-7-yl]methanesulfonamide

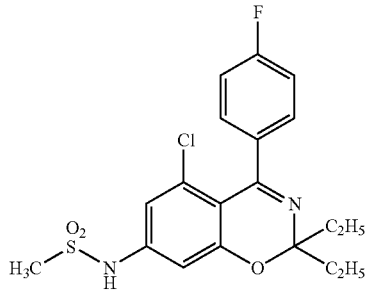

The objective compound of Reference Example 58 (124 mg) and mesylamine (67.9 mg) were treated in the same manner as Example 56(1) to give the titled compound (2.6 mg) as a yellow powder.

ESI-MS m/z: 409 [M–H]⁻

Example 68

Preparation of N-[2-ethyl-4-(2,4-difluorophenyl)-2-methyl-2H-1,3-benzoxazin-7-yl]-methanesulfonamide

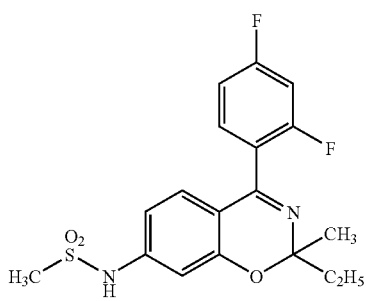

The objective compound of Reference Example 59 (400 mg) and methanesulfonyl chloride (301 mg) were treated in the same manner as Example 49 to give the titled compound (172 mg) as a yellow powder.

ACPI-MS m/z: 381[M+H]⁺

Example 69

Preparation of 2,2-diethyl-N-methyl-4-(4-fluorophenyl)-2H-1,3-benzoxazin-7-sulfonamide

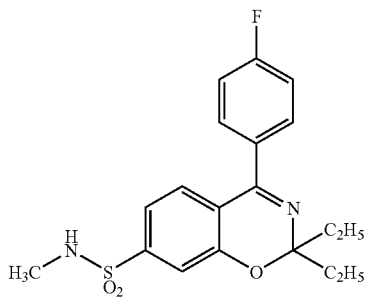

The objective compound of Reference Example 60 (600 mg) and methylamine hydrochloride (316 mg) were treated in the same manner as Example 61 to give the titled compound (60 mg) as a colorless powder.

APCI-MS m/z: 377 [M+H]⁺

Example 70

Preparation of N-[3-cyano-5-fluoro-4-(4-fluorophenyl)-2,2-dimethyl-2H-chromen-7-yl]-methanesulfonamide

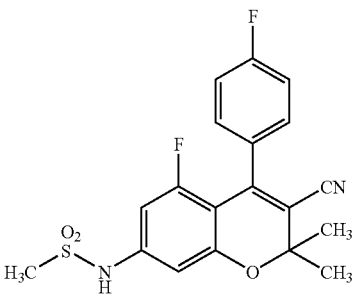

The objective compound of Example 48 (385 mg) was treated in the same manner as Example 50(1), and the obtained product (447 mg) was treated in the same manner as Example 50(2) to give the titled compound (93 mg) as a yellow powder.

ESI-MS m/z: 389 [M–H]⁻

Example 71

Preparation of N-[5-chloro-3-cyano-4-(4-fluorophenyl)-2,2-dimethyl-2H-chromen-7-yl]-methanesulfonamide

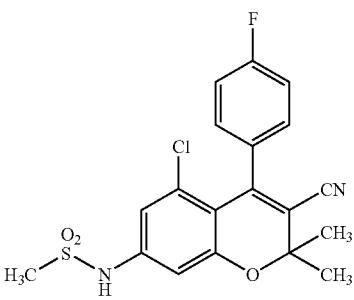

The objective compound of Example 63 (200 mg) was treated in the same manner as Example 50(1), and the obtained product (230 mg) was treated in the same manner as Example 50(2) to give the titled compound (94 mg) as a yellow powder.

ESI-MS m/z: 405/407 [M–H]⁻

Reference Example 1

(1) Preparation of 2-acetoxy-4-nitrobenzoic acid

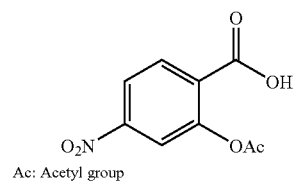

Ac: Acetyl group

A solution of 2-hydroxy-4-nitrobenzoic acid (16.84 g) in acetic anhydride (60 mL) was heated under reflux overnight. After cooling, the reaction solution was concentrated in vacuo, water and tetrahydrofuran were added to the residue, and the mixture was stirred at room temperature for 4 hours. The aqueous solution was extracted with ethyl acetate, the organic layer was washed successively with water and brine, dried over anhydrous magnesium sulfate and concentrated in vacuo. The resultant residue was suspended in diisopropyl ether, the resultant precipitates were collected by filtration and washed with diisopropyl ether to give the titled compound (13.75 g) as a colorless powder.

ESI-MS m/z: 224 [M−H]⁻

(2) Preparation of N-acetyl-2-hydroxy-4-nitrobenzamide

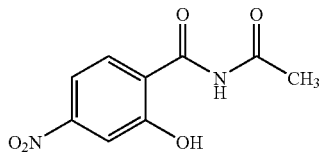

After addition of anhydrous dimethylformamide (52 μL) to a solution of the compound obtained in (1) described above (5.45 g) in tetrahydrofuran (25 mL), oxalyl chloride (5.28 mL) was added dropwise thereto, and the mixture was stirred at room temperature for 2 hours. The reaction solution was concentrated in vacuo, and the resultant residue was dissolved in tetrahydrofuran (15 mL). The solution was added to a mixture of an aqueous saturated ammonia (25 mL) and tetrahydrofuran (25 mL), and the mixture was stirred at room temperature for 1.5 hours after the addition of an aqueous saturated ammonia (15 mL). The reaction solution was concentrated in vacuo, water was added to the residue, and pH was adjusted to 1-2 by adding 10% hydrochloric acid. The mixture was extracted with ethyl acetate, and the organic layer was concentrated in vacuo. The resultant residue was suspended in water, and the precipitates were filtered and washed with diisopropylethyl ether and dried in vacuo at 60° C. to give the titled compound (4.13 g) as a yellow powder.

ESI-MS m/z: 223 [M−H]⁻

(3) Preparation of 2,2-dimethyl-7-nitro-2,3-dihydro-4H-1,3-benzoxazin-4-one

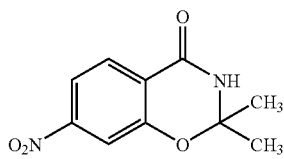

p-Toluenesulfonic acid hydrate (430 mg) was added to a suspension of the compound obtained in (2) described above (4.13 g) in acetone (27 mL)-dimethoxyethane (9.1 mL), and the mixture was heated under reflux overnight. The reaction solution was cooled and concentrated in vacuo, and the resultant residue was suspended in ethyl acetate. The precipitates were collected by filtration and washed with ethyl acetate to give the titled compound (3.00 g) as a pale yellow powder.

ACPI-MS m/z: 223 [M+H]⁺

(4) Preparation of 2,2-dimethyl-7-nitro-2H-1,3-benzoxazin-4-yl trifluoromethanesulfonate

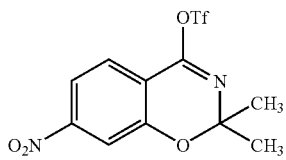

Tf: trifluoromethanesulfonyl group

Trifluoromethanesulfonic anhydride (3.26 mL) and 2,6-lutidine (2.30 mL) were added dropwise successively to a suspension of the compound obtained in (3) described above (2.87 g) in dichloromethane (40 mL) under cooling at −10° C., and the mixture was stirred at the same temperature for 1.5 hours. The reaction mixture was poured into ice water, and the solution was extracted with ethyl acetate. The organic layer was washed successively with a 10% aqueous solution of potassium hydrogensulfate, a saturated aqueous solution of sodium bicarbonate and brine, dried over anhydrous magnesium sulfate and concentrated in vacuo to give the titled compound (5.13 g) as a crude product (a brown oil).

(5) Preparation of 4-(4-chlorophenyl)-2,2-dimethyl-7-nitro-2H-1,3-benzoxazine

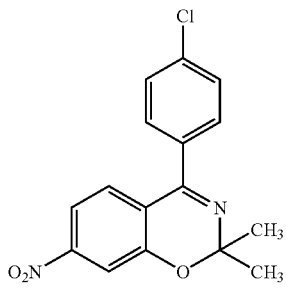

4-Chlorophenylboronic acid (199 mg), potassium carbonate (468 mg), water (224 μL) and dichlorobis(triphenylphosphine)palladium(II) (119 mg) were added to a solution of the compound obtained in (4) described above (300 mg) in dimethoxyethane (18.5 mL), and the mixture was stirred under argon atmosphere at 80° C. for 2.5 hours. After cooling, the reaction solution was diluted with ethyl acetate. The solution was washed successively with water and brine, dried over anhydrous magnesium sulfate and concentrated in vacuo. The resultant residue was purified by column chromatography on silica gel (Solvent: n-hexane/ethyl acetate=98/2 to 85/15) to give the titled compound (150 mg) as a yellow oil.

APCI-MS m/z: 317/319[M+H]⁺

(6) Preparation of 4-(4-chlorophenyl)-2,2-dimethyl-2H-1,3-benzoxazin-7-amine

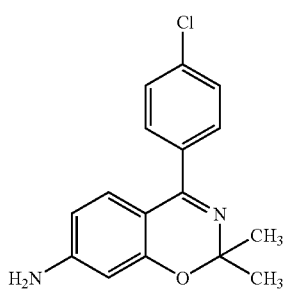

Reduced iron (124 mg) and ammonium chloride (36 mg) were added to a solution of the compound obtained in (5) described above (141 mg) in ethanol/water ((3 mL/3 mL), and the mixture was stirred at 80° C. for 2 hours. After cooling, the reaction solution was diluted with water and the mixture was extracted with ethyl acetate. The organic layer was washed with brine, dried over anhydrous magnesium sulfate and concentrated in vacuo. The resultant residue was purified by column chromatography on silica gel (Solvent: n-hexane/ethyl acetate=85/15 to 50/50) to give the titled compound (117 mg) as a yellow oil.

ACPI-MS m/z: 287/289[M+H]+

Reference Example 2

(1) Preparation of 4-chloro-2,6-difluorobanzoic acid

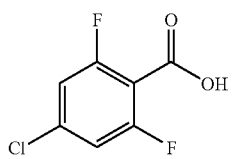

1.6M n-Butyl lithium/hexane solution (15.38 mL) was added to a solution of 1-chloro-3,5-difluorobenzene (2.24 mL) in anhydrous tetrahydrofuran (50 mL) under argon atmosphere and cooling in dry ice-acetone bath (−78° C.). After stirring at −50° C. for one hour, powdered dry ice (50 mL) was added to the reaction solution, and the mixture was stirred at the same temperature for 3 hours. The reaction solution was further stirred at room temperature for one hour and concentrated in vacuo. An aqueous 2N sodium hydroxide solution (3 mL) and water was added to the resultant residue, and the mixture was washed with diethyl ether. The aqueous layer was adjusted to pH 1-2 with 10% hydrochloric acid and extracted with diethyl ether. The combined organic layer was washed with brine, dried over anhydrous magnesium sulfate and concentrated in vacuo. The resultant residue was suspended in hexane, and the precipitates were collected by filtration. The precipitates were washed with hexane and dried at room temperature to give the titled compound (3.23 g) as a colorless powder.

ESI-MS m/z: 191/193[M−H]−

(2) Preparation of 4-chloro-2,6-difluorobenzamide

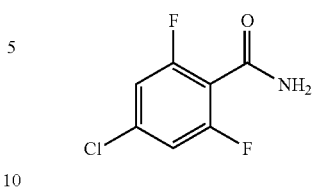

To a solution of the compound obtained in (1) described above (3.23 a) in dichloromethane (30 mL) was added anhydrous dimethylformamide (20 μL), and thereto was added dropwise oxalyl chloride (1.76 mL), and the mixture was stirred at room temperature for 1.5 hours. The reaction solution was concentrated in vacuo, and the resultant residue was dissolved in tetrahydrofuran (20 mL), and the solution was added gradually dropwise to a mixture of an aqueous saturated ammonia (25 mL) and tetrahydrofuran (25 mL) under stirring. The mixture was stirred at room temperature for 1.5 hours, and the reaction solution was concentrated in vacuo. Water was added to the resultant residue. After adjusting pH to 1-2 with 10% hydrochloric acid, the mixture was extracted with ethyl acetate. The organic layer was washed with brine, dried over anhydrous magnesium sulfate and concentrated in vacuo. The resultant residue was suspended in diisopropyl ether, the precipitates were collected by filtration, washed with diisopropyl ether and dried in vacuo at room temperature to give the titled compound (2.71 g) as a colorless powder.

ACPI-MS m/z: 192/194 [M+H]+

(3) Preparation of 2-(benzyloxy)-4-chloro-6-fluorobenzamide

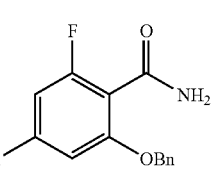

Bn: benzyl group

Sodium hydride (60%, 791 mg) was added portionwise to a solution of benzyl alcohol (1.83 g) in anhydrous dimethylformamide (16 mL) under ice-cooling and the mixture was stirred at room temperature for one hour. To the reaction solution was added a solution of the compound obtained in (2) described above (2.71 g) in anhydrous dimethylformamide (12 mL), and the mixture was stirred at room temperature overnight. The reaction solution was poured gradually into 10% hydrochloric acid, and the mixture was extracted with chloroform. The organic layer was washed successively with water and brine, dried over anhydrous magnesium sulfate and concentrated in vacuo. The resultant residue was purified by column chromatography on silica gel (Solvent: n-hexane/ethyl acetate=90/10 to 50/50) to give the titled compound (2.99 g) as a colorless powder.

ACPI-MS m/z: 280/282 [M+H]+

(4) Preparation of 4-chloro-2-fluoro-6-hydroxybenzamide

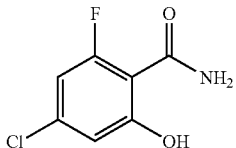

5% Palladium-carbon (PH type; 400 mg) was added to a solution of the compound obtained in (3) described above (2.99 g) in ethyl acetate (200 mL), and the mixture was stirred under hydrogen atmosphere at room temperature for 40 minutes. The reaction solution was filtered and the filtrate was concentrated in vacuo. The residue was suspended in diisopropyl ether and the precipitates were collected by filtration, washed with diisopropyl ether and dried in vacuo at room temperature to give the titled compound (1.32 g) as a colorless powder.

ACPI-MS m/z: 190/192 [M+H]$^+$

(5) Preparation of 7-chloro-5-fluoro-2,2-dimethyl-2,3-dihydro-4H-1,3-benzoxazin-4-one

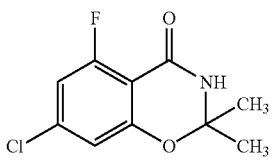

p-Toluenesulfonic acid monohydrate (73 mg) was added to a solution of the compound obtained in (4) described above (729 mg) in acetone (3 mL) and 2,2-dimethoxypropane (9 mL), and the mixture was heated under reflux overnight. The reaction solution was concentrated in vacuo, and the resultant residue was purified by column chromatography on silica gel (Solvent: n-hexane/ethyl acetate=90/10 to 40/60) to give the titled compound (641 mg) as a pale yellow powder.

ACPI-MS m/z: 230/232 [M+H]+

(6) Preparation of 7-chloro-5-fluoro-2,2-dimethyl-2H-1,3-benzoxazin-4-yl trifluoromethanesulfonate

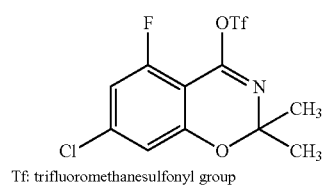

Tf: trifluoromethanesulfonyl group

Trifluoromethanesulfonic anhydride (1.67 mL) and 2,6-lutidine (1.54 mL) were added successively to a suspension of the compound obtained in (5) described above (1.52 g) in dichloromethane (40 mL) under cooling at −5° C. After stirring at the same temperature for 30 minutes, the reaction mixture was poured into ice-water, and the mixture was extracted with ethyl acetate. The organic layer was washed successively with ice-cooled 5% hydrochloric acid, a saturated aqueous solution of sodium bicarbonate and brine, dried over anhydrous magnesium sulfate and concentrated in vacuo. The resultant residue was purified by column chromatography on silica gel (Solvent: n-hexane/ethyl acetate=98/2 to 95/5) to give the titled compound (2.16 g) as a dark yellow oil.

(7) Preparation of 7-chloro-5-fluoro-4-(4-fluorophenyl)-2,2-dimethyl-2H-1,3-benzoxazine

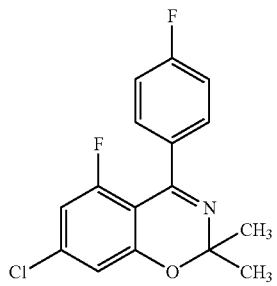

4-Fluorophenylboronic acid (154 mg), potassium carbonate (536 mg), water (225 µL) and dichlorobis(triphenylphosphine)palladium(II) (35 mg) were added to a solution of the compound obtained in (6) described above (262 mg) in dimethoxyethane (19 mL), and the mixture was stirred under argon atmosphere at 80° C. for 3 hours. The reaction solution was cooled and diluted with ethyl acetate. The solution was washed with water and brine, dried over anhydrous magnesium sulfate and concentrated in vacuo. The resultant residue was purified by column chromatography on silica gel (Solvent: n-hexane/ethyl acetate=99/1 to 90/10) to give the titled compound (136 mg) as a yellow oil.

ACPI-MS m/z: 308/310 [M+H]$^+$

(8) Preparation of tert-butyl [5-fluoro-4-(4-fluorophenyl)-2,2-dimethyl-2H-1,3-benzoxazin-7-yl]carbamate

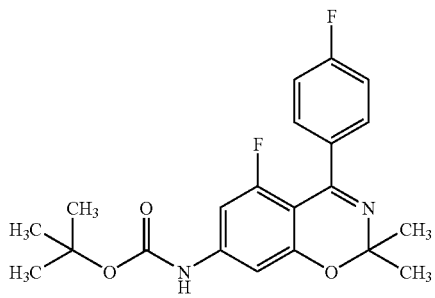

2-Dicyclohexylphosphiono-2',4',6'-triisopropyl-1,1'-biphenyl (20.6 mg) and phenylboronic acid (2.6 mg) were added to a solution of palladium acetate(II) (3.9 mg) in tert-butyl alcohol (2.9 mL), and the mixture was stirred under argon atmosphere at 30° C. for 30 minutes. To the reaction solution was added a solution of the compound obtained in (6) described above (133 mg) in tert-butyl alcohol (7.2 mL), tert-butyl carbamate and potassium carbonate (179 mg), and the mixture was stirred under argon atmosphere at 90° C. overnight.

After cooling, the reaction solution was diluted with ethyl acetate. The solution was washed successively with water and brine, dried over anhydrous magnesium sulfate and concentrated in vacuo. The resultant residue was purified by column chromatography on silica gel (Solvent: n-hexane/ethyl acetate=95/5 to 70/30) to give the titled compound (153 mg) as a pale yellow powder.

APCI-MS m/z: 389 [M+H]$^+$

(9) Preparation of 5-fluoro-4-(4-fluorophenyl)-2,2-dimethyl-2H-1,3-benzoxazin-7-amine

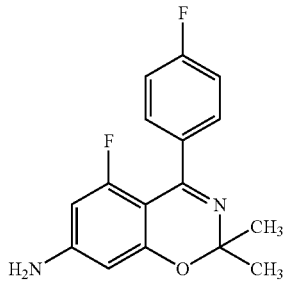

A solution of the compound obtained in (8) described above (148 mg) in trifluoroacetic acid (2 mL) was stirred at room temperature for an hour. The reaction solution was added dropwise to a saturated aqueous solution of sodium bicarbonate, and the mixture was extracted with chloroform. The organic layer was washed successively with a saturated aqueous solution of sodium bicarbonate and brine, dried over anhydrous magnesium sulfate and concentrated in vacuo. The resultant residue was purified by column chromatography on silica gel (Solvent: n-hexane/ethyl acetate=80/20 to 40/60) to give the titled compound (94 mg) as a pale yellow powder.

ACPI-MS m/z: 289 [M+H]$^+$

Reference Example 3

(1) Preparation of 1-(3-chloro-5-fluorophenyl)-2,5-dimethyl-1H-pyrrole

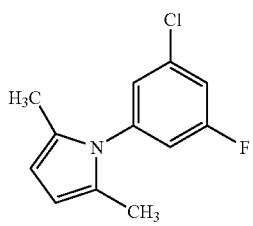

2,5-Hexanedione (4.51 mL) and p-toluenesulfonic acid monohydrate (73 mg) were added to a solution of 3-chloro-5-fluoroaniline (5.12 g) in toluene (40 mL)-tetrahydrofuran (40 mL), and the mixture was heated under reflux for 3.5 hours. After being cooled down, the reaction solution was concentrated in vacuo, and the resultant residue was dissolved in chloroform. The solution was washed successively with water and brine, dried over anhydrous sodium sulfate and concentrated in vacuo. The resulted residue was purified by column chromatography on silica gel (Solvent: n-hexane/ethyl acetate=97/3) to give the titled compound (7.63 g) as a yellow oil.

ACPI-MS m/z: 224/226 [M+H]$^+$

(2) Preparation of 2-chloro-4-(2,5-dimethyl-1H-pyrrol-1-yl)-6-fluorobenzoic acid

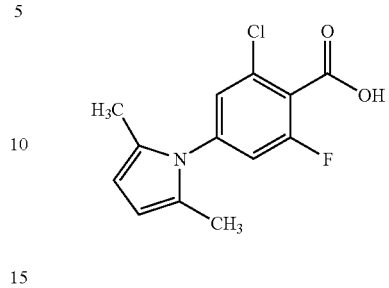

1.6M n-Butyl lithium/hexane solution (25.57 mL) was added dropwise to a solution of the compound obtained in (1) described above (7.63 g) in anhydrous tetrahydrofuran (85 mL) under cooling in dry ice-acetone bath (−78° C.) and under argon atmosphere, and the solution was stirred at −60° C. for an hour. Powdered dry ice (100 mL) was added to the reaction solution and the solution was stirred for 80 minutes, and then at room temperature for 30 minutes. The reaction solution was concentrated in vacuo, and to the resultant residue was added an aqueous 2N sodium hydroxide solution (12 mL) and water. The mixture was washed with diethyl ether and the aqueous layer was extracted with diethyl ether after adjusting pH to 2 with a 10% aqueous solution of potassium hydrogensulfate. The organic layer was dried over anhydrous sodium sulfate and concentrated in vacuo to give the titled compound (10.13 g) as a dark red oil.

ESI-MS m/z: 266/268 [M−H]$^-$

(3) Preparation of 2-chloro-4-(2,5-dimethyl-1H-pyrrol-1-yl)-6-fluorobenzamide

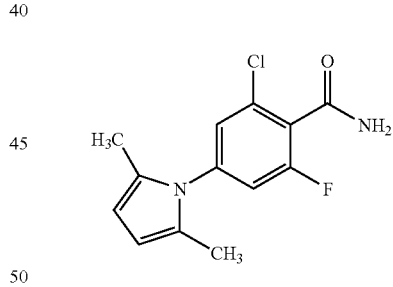

1-Ethyl-3-(3-dimethylaminopropyl)carbodiimide hydrochloride (8.70 g), 1-hydroxy-benzotriazole (6.13 g) and an aqueous saturated ammonia (44 mL) were added to a solution of the compound obtained in (2) described above (10.13 g) in anhydrous dimethylformamide (125 mL), and the mixture was stirred at room temperature overnight. The reaction solution was diluted with ethyl acetate, and the solution was washed successively with water and brine, dried over anhydrous magnesium sulfate and concentrated in vacuo. The resultant residue was suspended in diisopropyl ether, and the precipitates were collected by filtration and washed with diisopropyl ether to give the titled compound (5.43 g) as a colorless powder.

ACPI-MS m/z: 267/269 [M+H]$^+$

(4) Preparation of 2-(benzyloxy)-6-chloro-4-(2,5-dimethyl-1H-pyrrol-1-yl)benzamide

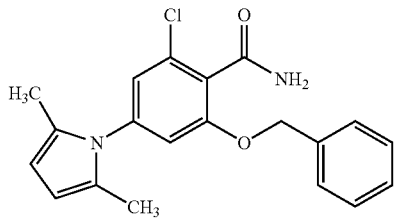

Sodium hydride (60%, 1.36 g) was added portionwise to a solution of benzyl alcohol (3.16 g) in anhydrous dimethylformamide (37 mL) under ice-cooling, and the mixture was stirred at room temperature for one hour. To the reaction solution was added dropwise a solution of the compound obtained in (3) described above (6.50 g) in anhydrous dimethylformamide (37 mL), and the mixture was stirred at room temperature for 6 hours. The reaction solution was gradually added to an ice-cooled 5% hydrochloric acid, and the solution was extracted with ethyl acetate-tetrahydrofuran. The organic layer was washed successively with water and brine, dried over anhydrous magnesium sulfate and concentrated in vacuo. The resultant residue was suspended in hot ethyl acetate, and the suspension was cooled to room temperature. The precipitates were collected by filtration, washed successively with ethyl acetate and diisopropyl ether to give the titled compound (6.90 g) as a pale yellow powder.

ACPI-MS m/z: 355/357 [M+H]$^+$

(5) Preparation of 2-chloro-4-(2,5-dimethyl-1H-pyrrol-1-yl)-6-hydroxybenzamide

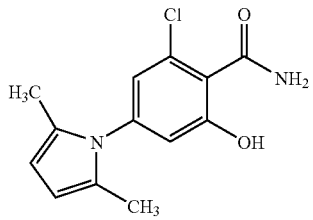

5% Palladium-carbon (PH type; 1.5 g) was added to a solution of the compound obtained in (4) described above (4.08 g) in ethyl acetate (500 mL), and the mixture was stirred under hydrogen atmosphere at room temperature for one hour. The reaction mixture was filtered and the filtrate was concentrated in vacuo. The resultant residue was purified by column chromatography on silica gel (Solvent: n-hexane/ethyl acetate=85/15 to 30/70) and the resultant precipitates were suspended in hexane/diisopropylether and collected by filtration. The precipitates were washed with hexane-diisopropyl ether and dried in vacuo at room temperature to give the titled compound (2.37 g) as a colorless powder.

ACPI-MS m/z: 265/267 [M+H]$^+$

(6) Preparation of 5-chloro-7-(2,5-dimethyl-1H-pyrrol-1-yl)-2,2-dimethyl-2,3-dihydro-4H-1,3-benzoxazin-4-one

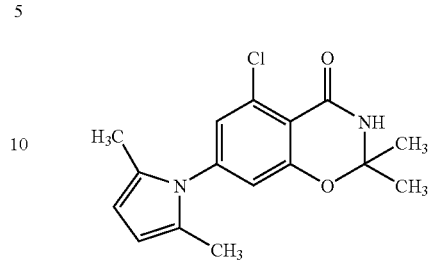

2,2-Dimethoxypropane (2 mL) and pyridinium p-toluenesulfonate (25 mg) were added to a solution of the compound obtained in (5) described above (264 mg) in toluene (10 mL), and the mixture was heated under reflux for 2 hours. After cooling, the reaction solution was diluted with ethyl acetate. The solution was washed successively with water, a saturated aqueous solution of sodium bicarbonate and brine, dried over anhydrous magnesium sulfate and concentrated in vacuo. The resultant residue was purified by column chromatography on silica gel (Solvent: n-hexane/ethyl acetate=85/15 to 20/80) to give the titled compound (272 mg) as a colorless powder.

ACPI-MS m/z: 305/307 [M+H]$^+$

(7) Preparation of 5-chloro-7-(2,5-dimethyl-1H-pyrrol-1-yl)-4-(4-fluorophenyl)-2,2-dimethyl-2H-1,3-benzoxazine

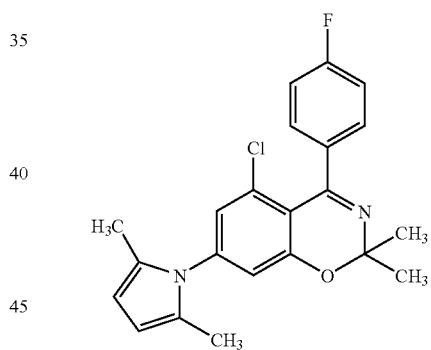

Trifluoromethanesulfonic acid anhydride (505 μL) and 2,6-lutidine (466 μL) were added successively to a solution of the compound obtained in (6) described above (610 mg) in dichloromethane (12 mL) under cooling at −10° C., and the mixture was stirred at the same temperature for 30 minutes. The reaction solution was poured into ice water, and the mixture was extracted with chloroform. The organic layer was washed successively with an ice-cooled 5% hydrochloric acid, a saturated aqueous solution of sodium bicarbonate and brine, dried over anhydrous magnesium sulfate and concentrated in vacuo to give 5-chloro-7-(2,5-dimethyl-1H-pyrrol-1-yl)-2,2-dimethyl-2H-1,3-benzoxazin-4-yl trifluoromethanesulfonate as a crude product (a brown oil). To a solution of the compound in dimethoxyethane (37 mL) were added 4-fluorophenylboronic acid (420 mg), potassium carbonate (1.1 g), dichlorobis(triphenylphosphine)palladium(1) (140 mg) and water (450 μL), and the mixture was stirred under argon atmosphere at 80° C. for one hour. After cooling, the reaction solution was diluted with ethyl acetate. The solution was washed successively with water and brine, dried over anhydrous magnesium sulfate and concentrated in vacuo. The resultant residue was purified by column chromatography on silica gel (Solvent: n-hexane/ethyl acetate=99/1 to 90/10) to give the titled compound (178 mg) as a yellow powder.

ACPI-MS m/z: 383/385 [M+H]+

(8) Preparation of 5-chloro-4-(4-fluorophenyl)-2,2-dimethyl-2H-1,3-benzoxazin-7-amine

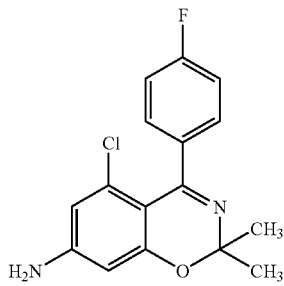

Trifluoroacetic acid (1 ml) was added to a solution of the compound obtained in (7) described above (50 mg) in 1,4-dioxane (1 mL)-water (1 mL), and the mixture was stirred at room temperature for 1.5 hours. The reaction solution was poured into a saturated aqueous solution of sodium bicarbonate, and the mixture was extracted with chloroform. The organic layer was washed with water, a saturated aqueous solution of sodium bicarbonate and saturated brine successively, dried over anhydrous magnesium sulfate and concentrated in vacuo. The resultant residue was purified by column chromatography on silica gel (Solvent: n-hexane/ethyl acetate=90/10 to 50/50) to give the titled compound (2.3 mg) as a yellow powder.

ACPI-MS m/z: 305/307 [M+H]+

Reference Example 4

(1) Preparation of 7-chloro-2,2-diethyl-4-(4-fluorophenyl)-2H-1,3-benzoxazine

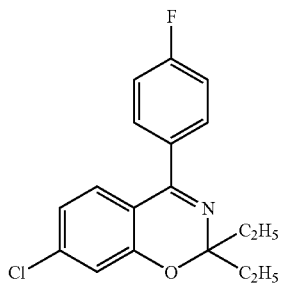

Ammonium iodide (724 mg), calcium sulfate (trade name: Drierite, 626 mg) and triethylamine (697 µL) were added to a solution of (4-chloro-2-hydroxyphenyl)(4-fluorophenyO-methanone (251 mg) in acetonitrile (3 mL) and the mixture was stirred under argon atmosphere at room temperature for 2 hours. A solution of 3-pentanone (318 µL) in acetonitrile (1 mL) was added to the reaction mixture. The mixture was stirred at 85° C. overnight and further heated under reflux overnight after the addition of toluene (10 mL). The reaction solution was filtered and the filtrate was concentrated in vacuo. A solution of the resultant residue in isopropyl ether was washed successively with an aqueous 0.1N sodium hydroxide solution, water and brine, filtered through a column of porous diatomite (Chem Elut) and a column of solid phase extraction (Bond Elut jr NH2 (trade name); Varian Inc.). The filtrate was concentrated in vacuo and the resultant residue was purified by column chromatography on NH-silica gel (Chromatorex NH silica gel, Solvent: n-hexane/ethyl acetate=100/0 to 95/5) to give the titled compound (113 mg) as a yellow oil.

ACPI-MS m/z: 318/320 [M+H]+

(2) Preparation of tert-butyl [2,2-diethyl-4-(4-fluorophenyl)-2H-1,3-benzoxazin-7-yl]carbamate

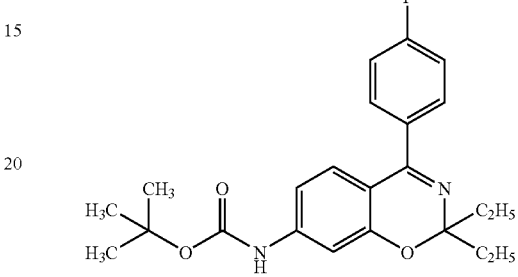

2-Dicyclohexylphosphiono-2',4',6'-triisopropyl-1,1'-biphenyl (46 mg) and phenylboronic acid (5.3 mg) were added to a solution of palladium acetate(II) (8.7 mg) in tert-butyl alcohol (2.3 mL), and the mixture was stirred under argon atmosphere at 30° C. for 30 minutes. To the reaction solution were added a solution of the compound obtained in (1) described above (112 mg) in tert-butyl alcohol (8.1 mL), tert-butyl carbamate (113 mg) and potassium carbonate (201 mg), and the mixture was stirred under argon atmosphere at 90° C. overnight. After cooling, the reaction solution was diluted with ethyl acetate. The solution was washed successively with water and brine, filtered through a column of porous diatomite (Chem Elut) and a column of solid phase extraction (trade name; Bond Elut jr NH2). The filtrate was concentrated in vacuo and the resultant residue was purified by column chromatography on silica gel (Solvent: n-hexane/ethyl acetate=95/5 to 75/25) to give the titled compound (119 mg) as a colorless powder.

ACPI-MS m/z: 399 [M+H]+

(3) Preparation of 2,2-diethyl-4-(4-fluorophenyl)-2H-1,3-benzoxazine-7-amine

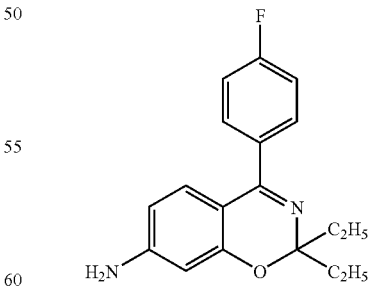

Trifluoroacetic acid (2 mL) was added to a solution of the compound obtained in (2) described above (117 mg) in chloroform (3 mL) and the mixture was stirred at room temperature for 45 minutes. The reaction solution was added dropwise to a saturated aqueous solution of sodium bicarbonate and the mixture was extracted with chloroform. The organic layer was washed successively with water, a saturated aqueous solution of sodium bicarbonate and brine, dried over anhydrous magnesium sulfate and concentrated in vacuo. The resultant residue was purified by column chromatography on silica gel (Solvent: n-hexane/ethyl acetate=80/20 to 30/70) to give the titled compound (85 mg) as a pale yellow powder.
ACPI-MS m/z: 299 [M+H]$^+$ Reference Example 5

(1) Preparation of 7-chloro-4-(4-fluorophenyl)-2H-chromen-2-one

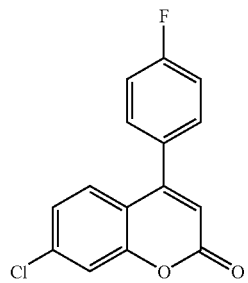

Under argon atmosphere, a mixture of (4-chloro-2-hydroxyphenyl)(4-fluorophenyl)methanone (1.00 g) and methyl(triphenylphosphoranylidene)acetate (3.00 g) in toluene (15 mL) was heated under reflux for 15 hours. After cooling, the reaction solution was poured into a saturated aqueous solution of ammonium chloride and the mixture was extracted with ethyl acetate. The organic layer was washed successively with a saturated aqueous solution of sodium bicarbonate and brine, dried over sodium sulfate and concentrated in vacuo. The resultant residue was purified by column chromatography on silica gel (Solvent: n-hexane/ethyl acetate=95/5 to 85/15) and the product was triturated in n-hexane-diisopropyl ether to give the titled compound (0.54 g) as a pale yellow powder.
APCI-MS m/z: 275/277 [M+H]$^+$ (2) Preparation of 5-chloro-2-[(1Z)-1-(4-fluorophenyl)-3-hydroxy-3-methylbut-1-ene-1-yl]phenol

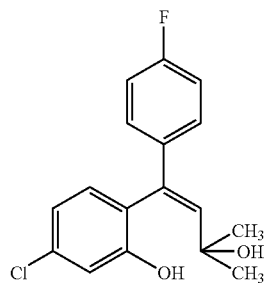

Under argon atmosphere, 3M methylmagnesium bromide-diethyl ether solution (9.90 mL) was added dropwise to a solution of the compound obtained in (1) described above (2.70 g) in tetrahydrofuran (50 mL) at room temperature, and the mixture was heated under reflux for one hour. To the reaction solution was added a saturated aqueous solution of ammonium chloride under ice-cooling, and the mixture was extracted with ethyl acetate. The organic layer was washed successively with water and brine, dried over sodium sulfate and concentrated in vacuo to give the titled compound (3.27 g) as a crude product (a pale brown viscous oil).
ESI-MS m/z: 305/307 [M–H]$^-$ (3) Preparation of 7-chloro-4-(4-fluorophenyl)-2,2-dimethyl-2H-chromen

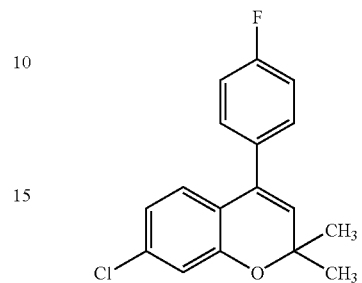

Under cooling in Ice/salt bath, concentrated hydrochloric acid (35 mL) was added to a solution of the compound obtained in (2) described above (3.26 g) in tetrahydrofuran (35 mL), and the mixture was stirred at room temperature for 0.5 hours. The reaction solution was poured into ice water and the mixture was extracted with ethyl acetate. The organic layer was washed with water, a saturated aqueous solution of sodium bicarbonate and brine, dried over sodium sulfate and concentrated in vacuo. The resultant residue was purified by column chromatography on silica gel (Solvent: n-hexane/ethyl acetate=40/1) and the product was recrystallized from n-hexane to give the titled compound (2.20 g) as pale yellow crystals.
APCI-MS m/z: 289/291 [M+H]$^+$ (4) Preparation of tert-butyl [4-(4-fluorophenyl)-2,2-dimethyl-2H-chromen-7-yl]carbamate

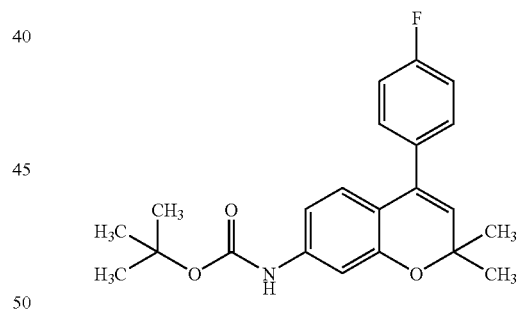

A mixture of palladium acetate (20 mg), 2-dicyclohexylphosphiono-2',4',6'-triisopropyl-1,1'-biphenyl (75 mg), phenylboronic acid (11 mg) and tert-butanol (2 ml) was stirred under argon atmosphere at 35° C. for 30 minutes. To the reaction solution was added a solution of the compound obtained in (3) described above (150 mg) in tert-butyl alcohol (1 ml), tert-butyl carbamate (185 mg) and potassium carbonate (360 mg), and the mixture was heated under reflux for 19 hours. After cooling, the reaction mixture was diluted with ethyl acetate and washed successively with water and brine. The organic layer was filtered through a column of porous diatomite (Chem Elut) and the filtrate was concentrated in vacuo. The resultant residue was purified by column chromatography on silica gel (Solvent: n-hexane/ethyl acetate=90/5 to 90/10) to give the titled compound (188 mg) as a pale brown viscous oil.
APCI-MS m/z: 387 [M+NH$_4$]$^+$

(5) Preparation of [4-(4-fluorophenyl)-2,2-dimethyl-2H-chromen-7-yl]amine

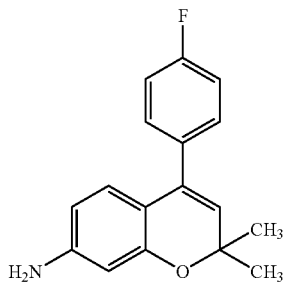

A solution of the compound obtained in (4) described above (170 mg) in 4N hydrogen chloride/dioxane solution (3 mL) was stirred at room temperature for one hour. A saturated aqueous solution of sodium bicarbonate was added to the reaction solution and the mixture was extracted with ethyl acetate. The organic layer was washed successively with water and brine, filtered through a column of porous diatomite (Chem Elut) and the filtrate was concentrated in vacuo to give the titled compound (115 mg) as a crude product (pale brown powder).

APCI-MS m/z: 270 [M+M]$^+$

Reference Example 6

(1) Preparation of 7-chloro-4-(4-fluorophenyl)-3-methyl-2H-chromen-2-one

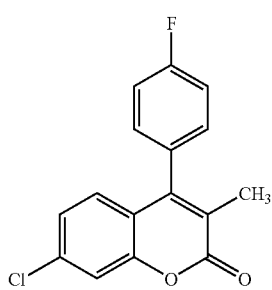

A mixture of (4-chloro-2-hydroxyphenyl)(4-fluorophenyl)methanone (200 mg) and (carboethoxyethylidene)triphenylphosphorane (435 mg) was heated with stirring at 200° C. for 15 hours. After cooling, the reaction mixture was diluted with ethyl acetate and the solution was poured into an aqueous saturated ammonium chloride solution. The mixture was extracted with ethyl acetate, and the organic layer was washed with water and brine, and filtered through a column of porous diatomite (Chem Elut). The filtrate was concentrated and the resulted residue was purified by column chromatography on silica gel (Solvent: n-hexane/ethyl acetate=97/3 to 90/10) to give the titled compound (119 mg) as a yellow powder.

ACPI-MS m/z: 289/291 [M+H]$^+$

(2) Preparation of 5-chloro-2-[(1Z)-1-(4-fluorophenyl)-3-hydroxy-2,3-dimethylbut-1-ene-1-yl]phenol

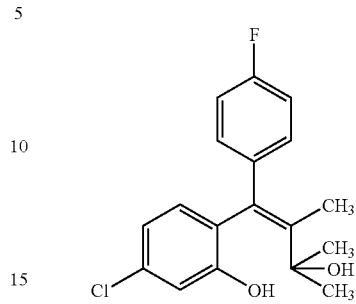

The compound obtained in (1) described above (250 mg) and a 3M methylmagnesium bromide in ethanol (0.87 mL) were treated in the same manner as Reference Example 5(2) to give the titled compound (312 mg) as a crude product (pale yellow powder).

ESI-MS m/z: 319/321 [M–H]$^-$

(3) Preparation of 7-chloro-4-(4-fluorophenyl)-2,2,3-trimethyl-2H-chromen

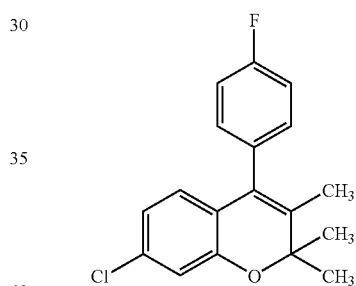

The compound obtained in (2) described above (310 mg) was heated with stirring at 150° C. for 6 hours. The resulted residue was purified by column chromatography on silica gel (Solvent: n-hexane/ethyl acetate=100/0 to 95/5) to give the titled compound (106 mg) as a colorless powder.

ACPI-MS m/z: 303/305 [M+H]$^+$

(4) Preparation of tert-butyl [4-(4-fluorophenyl)-2,2,3-trimethyl-2H-chromen-7-yl]carbamate

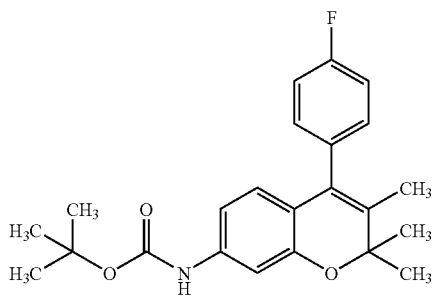

The compound obtained in (3) described above (100 mg) and tert-butyl carbamate (125 mg) were treated in the same manner as Reference Example 5(4) to give the titled compound (126 mg) as a pale brown powder.

ACPI-MS m/z: 401 [M+NH$_4$]$^+$ (5) Preparation of [4-(4-fluorophenyl)-2,2,3-trimethyl-2H-chromen-7-yl]amine

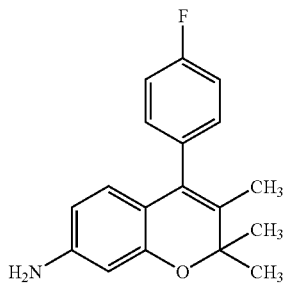

The compound obtained in (4) described above (126 mg) and 4N hydrochloric acid-dioxane solution (3 mL) were treated in the same manner as Reference Example 5(5) to give the titled compound (66 mg) as a pale brown viscous oil.

ACPI-MS m/z: 284 [M+H]$^+$

Reference Example 7

(1) Preparation of (4-chloro-2-methoxyphenyl)(4-fluorophenyl)methanone

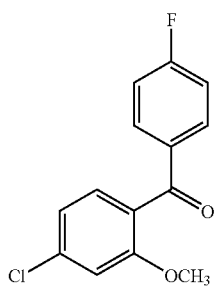

Methyl iodide (1.10 mL) was added to a suspension of (4-chloro-2-hydroxyphenyl)(4-fluorophenyl)methanone (3.00 g) and potassium carbonate (3.30 g) in N,N-dimethylformamide (50 mL) and the mixture was stirred at room temperature for 2.5 hours. The reaction solution was filtered through Celite and the filtrate was poured into an aqueous saturated ammonium chloride solution. The mixture was extracted with ethyl acetate and the organic layer was washed successively with water and brine, dried over sodium sulfate and concentrated in vacuo. The resultant residue was purified by column chromatography on silica gel (Solvent: n-hexane/ethyl acetate=30/1) to give the titled compound (2.95 g) as a pale yellow powder.

APCI-MS m/z: 265/267 [M+H]$^+$ (2) Preparation of ethyl 3-(4-chloro-2-methoxyphenyl)-2-fluoro-3-(4-fluorophenyl)acrylate

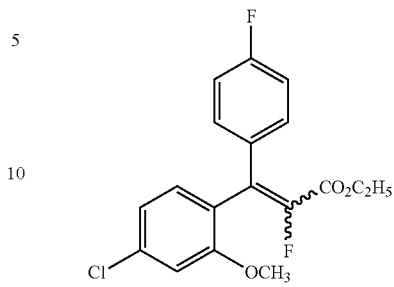

Triethyl 2-fluoro-2-phosphonoacetate (0.345 mL) was added to a suspension of 60% oily dispersion of sodium hydride (65 mg) in tetrahydrofuran (4 mL) and the mixture was stirred at room temperature for 1.5 hours. A solution of the compound obtained in (1) described above (300 mg) in tetrahydrofuran (1 mL) was added to the reaction solution and the mixture was stirred for 21 hours. The tetrahydrofuran solution was prepared from 60% sodium hydride in oil (65 mg) and triethyl 2-fluoro-2-phosphonoacetate (0.345 mL) in the same manner described above. The tetrahydrofuran solution was added to the reaction solution above. The mixture was stirred at room temperature for 3 hours. The reaction solution was poured into an aqueous saturated ammonium chloride solution and the mixture was extracted with ethyl acetate. The organic layer was washed successively with a saturated aqueous solution of sodium bicarbonate and brine, dried over sodium sulfate and concentrated in vacuo. The resultant residue was purified by column chromatography on silica gel (Solvent: n-hexane/ethyl acetate=98/2 to 85/15) to give the titled compound (a mixture of E-isomer and Z-isomer; 380 mg) as a colorless oil.

ACPI-MS m/z: 353/355 [M+H]$^+$ (3) Preparation of 7-chloro-3-fluoro-4-(4-fluorophenyl)-2H-chromen-2-one

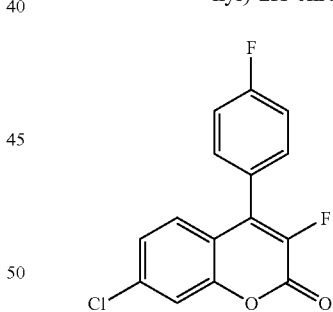

A solution of 1.0M boron tribromide-dichloromethane (3.2 mL) was added dropwise to a solution of the compound obtained in (2) described above (375 mg) in dichloromethane (20 mL) under ice-cooling and the mixture was stirred at room temperature for 2 hours. To the reaction solution was added water, and the mixture was evaporated to remove dichloromethane. Water was added to the residue and extracted with ethyl acetate.

The organic layer was washed with water and brine, filtered through a column of porous diatomite (Chem Elut) and the filtrate was concentrated in vacuo. The resultant residue was purified by column chromatography on silica gel (Solvent: n-hexane/ethyl acetate=95/5 to 80/20) to give the titled compound (286 mg) as a colorless powder.

ACPI-MS m/z: 293/295 [M+H]$^+$ (4) Preparation of 5-chloro-2[(1E)-2-fluoro-1-(4-fluorophenyl)-3-hydroxy-3-methylbut-1-ene-1-yl]phenol

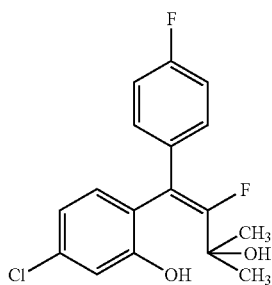

The compound obtained in (3) described above (283 mg) and a solution of 3M methylmagnesium bromide in ethanol (1 mL) were treated in the same manner as Reference Example 5(2) to give the titled compound (314 mg) as a crude product (a colorless viscous oil).
ESI-MS m/z: 323/325[M−H]⁻.

(5) Preparation of 7-chloro-3-fluoro-4-(4-fluorophenyl)-2,2-dimethyl-2H-chromen

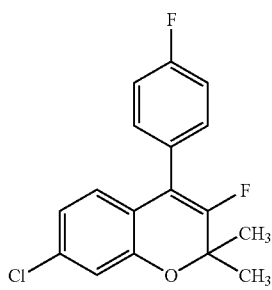

The compound obtained in (4) described above (314 mg) and concentrated hydrochloric acid (4 mL) were treated in the same manner as Reference Example 5(3) to give the titled compound (132 mg) as a colorless powder.
ACPI-MS m/z: 307/309[M+H]⁺

(6) Preparation of tert-butyl [3-fluoro-4-(4-fluorophenyl)-2,2-dimethyl-2H-chromen-7-yl]carbamate

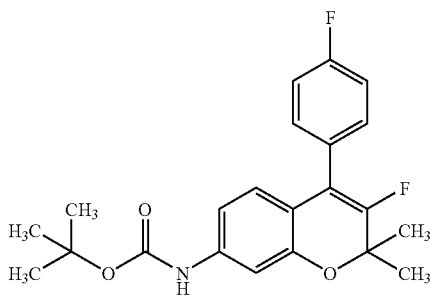

The compound obtained in (5) described above (125 mg) and tert-butyl carbamate (145 mg) were treated in the same manner as Reference Example 5(4) to give the titled compound (157 mg) as a brown viscous oil.
ACPI-MS m/z: 405[M+NH₄]⁺

(7) Preparation of [3-fluoro-4-(4-fluorophenyl)-2,2-dimethyl-2H-chromen-7-yl]amine

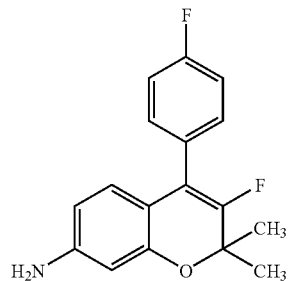

The compound obtained in (6) described above (157 mg) and 4N hydrochloric acid-dioxane solution (4 mL) were treated in the same manner as Reference Example 5(5) to give the titled compound (108 mg) as a pale yellow viscous oil.
ACPI-MS m/z: 288 [M+H]⁺

Reference Example 8

(1) Preparation of 3-bromo-7-chloro-4-(4-fluorophenyl)-2,2-dimethyl-2H-chromen

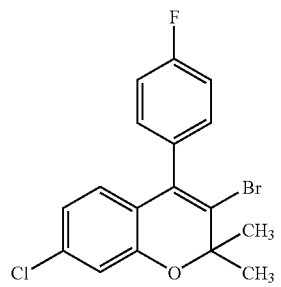

Pyridinium bromide perbromide (1.00 g) was added to a solution of 7-chloro-4-(4-fluorophenyl)-2,2-dimethyl-2H-chromen (a compound obtained in Reference Example 5(3); 1.00 g) in dichloromethane (15 mL) under ice-cooling and the mixture was stirred at room temperature for 1.5 hours. The reaction mixture was poured into a 15% aqueous solution of sodium thiosulfate and extracted with ethyl acetate. The organic layer was washed successively with a saturated solution of sodium bicarbonate and brine, dried over sodium sulfate and concentrated in vacuo. The resultant residue was purified by column chromatography on silica gel (Solvent: n-hexane/chloroform=100/0 to 95/5) to give the titled compound (1.26 g) as a colorless powder.
ACPI-MS m/z: 367/369 [M+H]⁺

(2) Preparation of 7-chloro-4-(4-fluorophenyl)-2,2-dimethyl-2H-chromen-3-carbonitrile

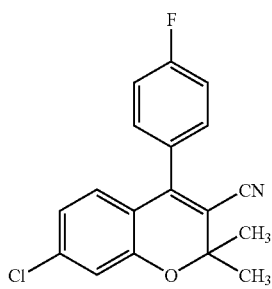

A mixture of the compound obtained in (6) described above (500 mg), zinc cyanide (160 mg) and tetrakis(triphenylphosphine)palladium(0) (475 mg) in N,N-dimethylformamide (10 mL) was heated at 100° C. for 18 hours. After cooling, to the reaction mixture was added ethyl acetate and water, and the mixture was filtered. The filtrate was extracted with ethyl acetate and the organic layer was washed successively with water and brine, filtered through a column of porous diatomite (Chem Elut). The filtrate was concentrated in vacuo and the resultant residue was purified by column chromatography on silica gel (Solvent: n-hexane/ethyl acetate=98/2 to 93/7) to give the titled compound (358 mg) as a colorless powder.
ACPI-MS m/z: 331/333[M+NH$_4$]$^+$ (3) Preparation of tert-butyl [3-cyano-4-(4-fluorophenyl)-2,2-dimethyl-2H-chromen-7-yl]carbamate

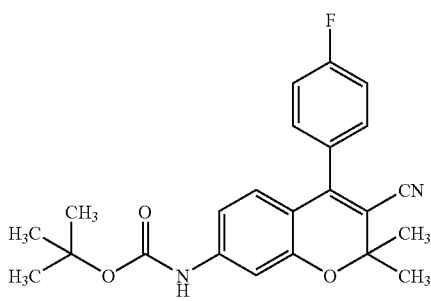

The compound obtained in (2) described above (340 mg) and tert-butyl carbamate (380 mg) were treated in the same manner as Reference Example 5(4) to give the titled compound (427 mg) as a pale yellow powder.
ACPI-MS m/z: 412 [M+H$_4$]$^+$ (4) Preparation of 7-amino-4-(4-fluorophenyl)-2,2-dimethyl-2H-chromen-3-carbonitrile

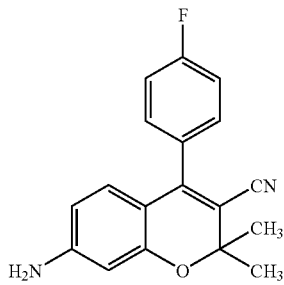

The compound obtained in (3) described above (250 mg) and 4N hydrochloric acid-dioxane solution (5 mL) were treated in the same manner as Reference Example 5(5) to give the titled compound (148 mg) as a yellow powder.
ACPI-MS m/z: 295 [M+H]$^+$ Reference Example 9

Preparation of 7-amino-4-(4-fluorophenyl)-2,2-dimethyl-2H-chromen-3-carboxamide

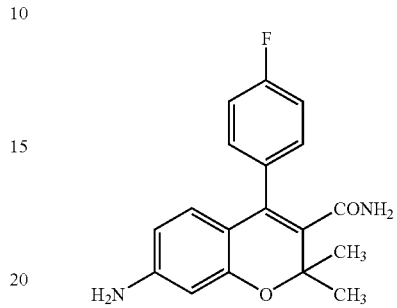

6N Hydrochloric acid (15 mL) was added to a solution of tert-butyl [3-cyano-4-(4-fluorophenyl)-2,2-dimethyl-2H-chromen-7-yl]carbamate (a compound obtained in Reference Example 8(3); 150 mg) in dioxane (5 mL) and the mixture was heated under reflux for 90 hours. The reaction solution was concentrated in vacuo, the resulted residue was diluted with ethyl acetate and washed with a saturated solution of sodium bicarbonate and brine. The organic layer was filtered through a column of porous diatomite (Chem Elut) and the filtrate was concentrated in vacuo. The resultant residue was purified by column chromatography on silica gel (Solvent: chloroform/methanol=100/0 to 95/5) to give the titled compound (26 mg) as a yellow powder.
ACPI-MS m/z: 313[M+H]$^+$ Reference Example 10

(1) Preparation of 7-chloro-3-cyclopropyl-4-(4-fluorophenyl)-2,2-dimethyl-2H-chromen

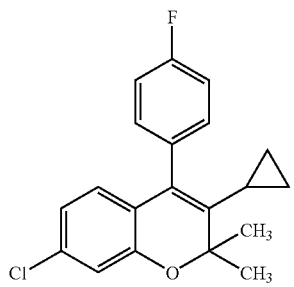

A mixture of 3-bromo-7-chloro-4-(4-fluorophenyl)-2,2-dimethyl-2H-chromen (a compound obtained in Reference Example 8(1); 200 mg), cyclopropylboronic acid (100 mg), potassium phosphate (410 mg) and tetrakis(triphenylphosphine)palladium(0) (65 mg) in dioxane (5 mL) was heated under reflux for 23 hours. After cooling, to the reaction solution was added water, and the mixture was extracted with ethyl acetate. The organic layer was washed with brine and filtered through a column of porous diatomite (Chem Elut), and the filtrate was concentrated in vacuo. The resultant residue was purified by column chromatography on silica gel (Solvent: n-hexane/chloroform=100/0 to 95/5) to give the titled compound (114 mg) as a colorless viscous oil.
ACPI-MS m/z: 329/331 [M+H]$^+$

(2) Preparation of tert-butyl [3-cyclopropyl-4-(4-fluorophenyl)-2,2-dimethyl-2H-chromen-7-yl]carbamate

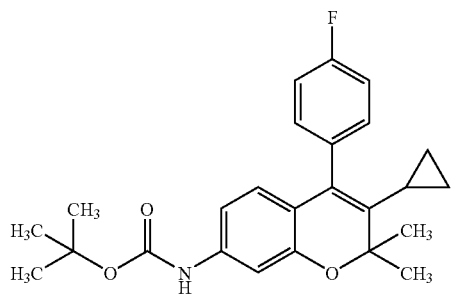

The compound obtained in (1) described above (112 mg) and tert-butyl carbamate (240 mg) were treated in the same manner as Reference Example 5(4) to give the titled compound (117 mg) as a pale brown powder.
ACPI-MS m/z: 427 [M+NH$_4$]$^+$

(3) Preparation of [3-cyclopropyl-4-(4-fluorophenyl)-2,2-dimethyl-2H-chromen-7-yl]amine

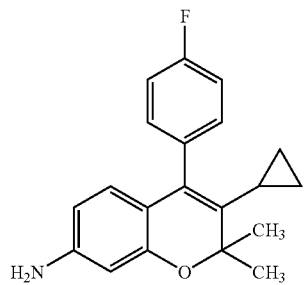

The compound obtained in (2) described above (115 mg) and 4N hydrochloric acid-dioxane solution (4 mL) were treated in the same manner as Reference Example 5(5) to give the titled compound as a crude product (a yellow powder).

Reference Example 11

(1) Preparation of 7-chloro-4-(4-fluorophenyl)-2,2-dimethyl-3-vinyl-2H-chromen

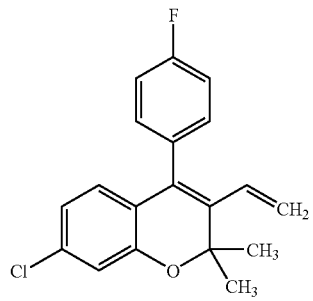

A mixture of 3-bromo-7-chloro-4-(4-fluorophenyl)-2,2-dimethyl-2H-chromen (a compound obtained in Reference Example 8(1); 220 mg), tributyl(vinyl)tin (350 µL) and tetrakis(triphenylphosphine)palladium(0) (140 mg) in dioxane was heated under reflux for 23 hours. After cooling, the reaction solution was diluted with ethyl acetate, a saturated aqueous solution of potassium fluoride was added thereto, and the mixture was stirred at room temperature for an hour. The reaction solution was filtered through Celite and the filtrate was extracted with ethyl acetate. The organic layer was washed successively with water and brine, filtered through a column of porous diatomite (Chem Elut) and the filtrate was concentrated in vacuo. The resultant residue was purified by column chromatography on silica gel (Solvent: n-hexane/chloroform=100/0 to 95/5) to give the titled compound (157 mg) as a pale yellow viscous oil.
ACPI-MS m/z: 315/317 [M+H]$^+$

(2) Preparation of tert-butyl [4-(4-fluorophenyl)-2,2-dimethyl-3-vinyl-2H-chromen-7-yl]carbamate

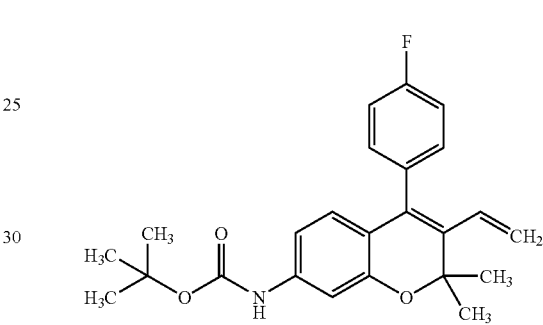

The compound obtained in (1) described above (155 mg) and tert-butyl carbamate (280 mg) were treated in the same manner as Reference Example 5(4) to give the titled compound (185 mg) as a yellow powder.
ACPI-MS m/z: 413 [M+NH$_4$]$^+$

(3) Preparation of [4-(4-fluorophenyl)-2,2-dimethyl-3-vinyl-2H-chromen-7-yl]amine

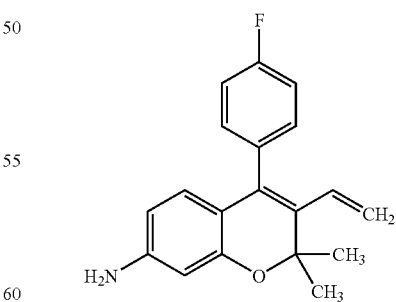

The compound obtained in (2) described above (182 mg) and 4N hydrochloric acid-dioxane solution (4 mL) were treated in the same manner as Reference Example 5(5) to give the titled compound as a crude product.

Reference Example 12

(1) Preparation of 7-chloro-3-(1-ethoxyvinyl)-4-(4-fluorophenyl)-2,2-dimethyl-2H-chromen

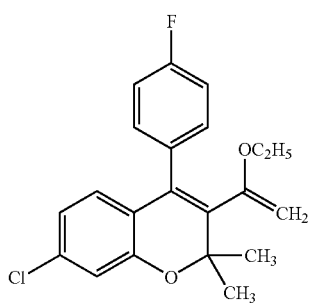

A mixture of 3-bromo-7-chloro-4-(4-fluorophenyl)-2,2-dimethyl-2H-chromen (a compound obtained in Reference Example 8(1); 220 mg) and tributyl(vinyl)tin (405 μL) were treated in the same manner as Reference Example 11(1) to give the titled compound (144 mg) as a pale yellow powder.

ACPI-MS m/z: 359/361 [M+H]$^+$

(2) Preparation of 1-[7-chloro-4-(4-fluorophenyl)-2,2-dimethyl-2H-chromen-3-yl]ethanone

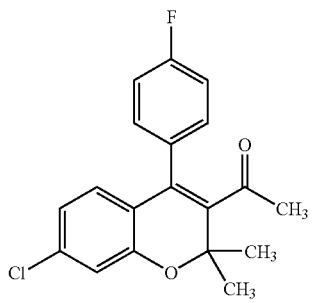

The compound obtained in (1) described above (140 mg) and 4N hydrochloric acid-dioxane solution (5 mL) were stirred at room temperature for 2 hours. The reaction solution was concentrated in vacuo, and to the resultant residue was added a saturated aqueous solution of sodium bicarbonate, and the mixture was extracted with ethyl acetate. The organic layer was washed with brine, filtered through a column of porous diatomite (Chem Elut) and the filtrate was concentrated in vacuo. The resultant residue was purified by column chromatography on silica gel (Solvent: n-hexane/ethyl acetate=98/2 to 90/10) to give the titled compound (121 mg) as a pale yellow powder.

ACPI-MS m/z: 331/333 [M+H]$^+$

(3) Preparation of tert-butyl [3-acetyl-4-(4-fluorophenyl)-2,2-dimethyl-2H-chromen-7-yl]carbamate

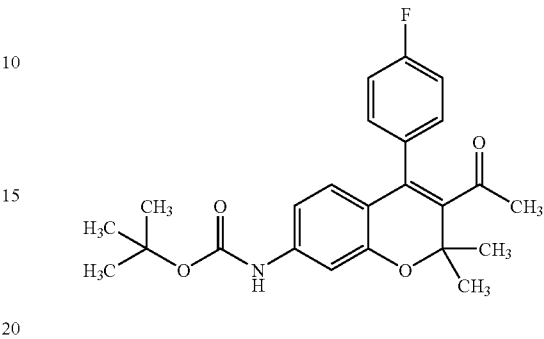

The compound obtained in (2) described above (118 mg) and tert-butyl carbamate (130 mg) were treated in the same manner as Reference Example 5(4) to give the titled compound (147 mg) as a yellow powder.

ACPI-MS m/z: 412 [M+H]$^+$

(4) Preparation of 1-[7-amino-4-(4-fluorophenyl)-2,2-dimethyl-2H-chromen-3-yl]ethanone

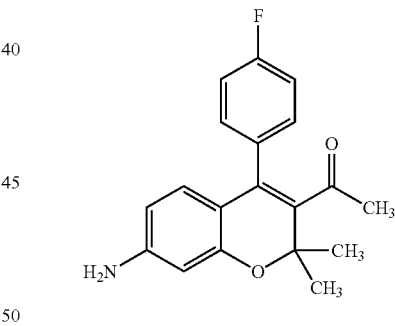

The compound obtained in (3) described above (147 mg) and 4N hydrochloric acid-dioxane solution (4 mL) were treated in the same manner as Reference Example 5(5) to give the titled compound as a crude product.

Reference Example 13 to 30

Corresponding starting compounds were treated in the same manner as Reference Example 1 to give the compounds in Tables 11-13.

TABLE 11

| Reference Example | Structure | Physicochemical properties |
|---|---|---|
| 13 | 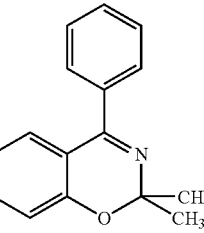 | pale yellow viscous oil MS(APCI)m/z: 253 [M + H]+ |
| 14 | 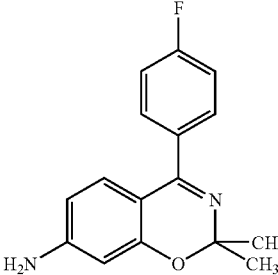 | pale yellow powder MS(APCI)m/z: 271 [M + H]+ |
| 15 | 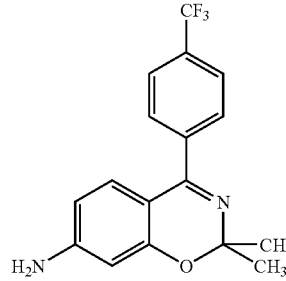 | pale yellow powder MS(APCI)m/z: 321 [M + H]+ |
| 16 | 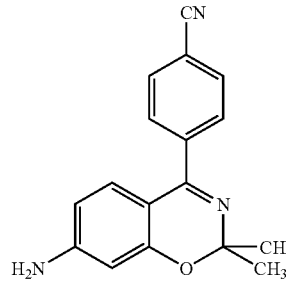 | pale yellow powder MS(APCI)m/z: 278 [M + H]+ |
| 17 | 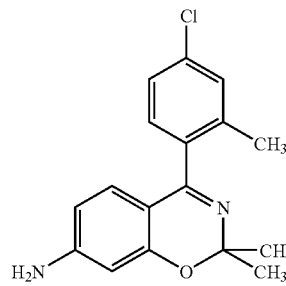 | colorless powder MS(APCI)m/z: 301/303 [M + H]+ |

TABLE 11-continued

| Reference Example | Structure | Physicochemical properties |
|---|---|---|
| 18 | 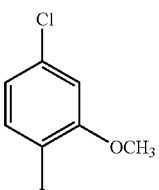 | pale yellow powder MS(APCI)m/z: 317/319 [M + H]+ |

TABLE 12

| Reference Example | Structure | Physicochemical properties |
|---|---|---|
| 19 | 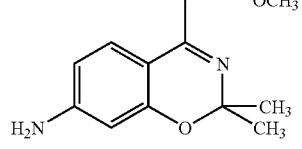 | pale yellow powder MS(APCI)m/z: 285 [M + H]+ |
| 20 | 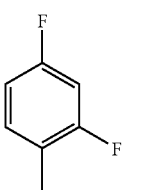 | colorless powder MS(APCI)m/z: 289 [M + H]+ |
| 21 | 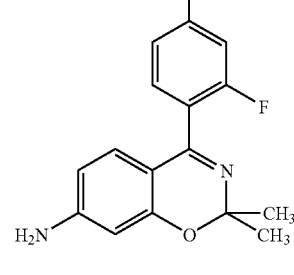 | pale yellow viscous oil MS(APCI)m/z: 305/307 [M + H]+ |

TABLE 12-continued

| Reference Example | Structure | Physicochemical properties |
|---|---|---|
| 22 | 4-(4-chloro-2-fluorophenyl)-2,2-dimethyl-2H-benzo[e][1,3]oxazin-7-amine | pale yellow viscous oil MS(APCI)m/z: 305/307 [M + H]+ |
| 23 | 4-(3,4-difluorophenyl)-2,2-dimethyl-2H-benzo[e][1,3]oxazin-7-amine | pale yellow powder MS(APCI)m/z: 289 [M + H]+ |
| 24 | 4-(4-chloro-3-methylphenyl)-2,2-dimethyl-2H-benzo[e][1,3]oxazin-7-amine | pale yellow viscous oil MS(APCI)m/z: 301/303 [M + H]+ |

TABLE 13

| Reference Example | Structure | Physicochemical properties |
|---|---|---|
| 25 | 4-(4-chloro-3-fluorophenyl)-2,2-dimethyl-2H-benzo[e][1,3]oxazin-7-amine | pale yellow powder MS(APCI)m/z: 305/307 [M + H]+ |
| 26 | 4-(4-fluoro-3-methylphenyl)-2,2-dimethyl-2H-benzo[e][1,3]oxazin-7-amine | pale yellow powder MS(APCI)m/z: 285 [M + H]+ |
| 27 | 4-(3-chloro-4-fluorophenyl)-2,2-dimethyl-2H-benzo[e][1,3]oxazin-7-amine | pale yellow powder MS(APCI)m/z: 305/307 [M + H]+ |
| 28 | 4-(4-fluoro-3-trifluoromethylphenyl)-2,2-dimethyl-2H-benzo[e][1,3]oxazin-7-amine | pale yellow powder MS(APCI)m/z: 339 [M + H]+ |
| 29 | 4-(benzo[b]thiophen-3-yl)-2,2-dimethyl-2H-benzo[e][1,3]oxazin-7-amine | pale pink powder MS(APCI)m/z: 309 [M + H]+ |
| 30 | 4-(benzofuran-2-yl)-2,2-dimethyl-2H-benzo[e][1,3]oxazin-7-amine | pale yellow powder MS(APCI)m/z: 293 [M + H]+ |

Reference Examples 31-32

Corresponding starting compounds were treated in the same manner as Reference Example 2 to give the compounds in Tables 14.

TABLE 14

| Reference Example | Structure | Physicochemical properties |
|---|---|---|
| 31 | [structure: 7-amino-5-fluoro-4-(4-fluoro-2-methylphenyl)-2,2-dimethyl-2H-benzo[e][1,3]oxazine] | pale yellow powder MS(APCI)m/z: 303 [M + H]$^+$ |
| 32 | [structure: 7-amino-5-fluoro-2,2-dimethyl-4-(4-(trifluoromethyl)phenyl)-2H-benzo[e][1,3]oxazine] | pale yellow powder MS(APCI)m/z: 339 [M + H]$^+$ |

Reference Examples 31-32

Corresponding starting compounds were treated in the same manner as Reference Example 4 to give the compounds in Tables 15.

TABLE 15

| Reference Example | Structure | Physicochemical properties |
|---|---|---|
| 33 | [structure: 7-amino-2-ethyl-4-(4-fluorophenyl)-2-methyl-2H-benzo[e][1,3]oxazine] | colorless powder MS(APCI)m/z: 285 [M + H]$^+$ |
| 34 | [structure: 7-amino-4-(4-fluorophenyl)-2-methyl-2-propyl-2H-benzo[e][1,3]oxazine] | yellow viscous oil MS(APCI)m/z: 299 [M + H]$^+$ |
| 35 | [structure: 7-amino-4-(4-fluorophenyl)-2-methyl-2-phenyl-2H-benzo[e][1,3]oxazine] | yellow viscous oil MS(APCI)m/z: 333 [M + H]$^+$ |

TABLE 15-continued

| Reference Example | Structure | Physicochemical properties |
|---|---|---|
| 36 | 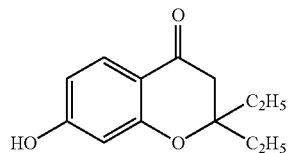 | yellow powder<br>MS(APCI)m/z: 319 [M + H]+ |

Reference Examples 37

(1) Preparation of 2,2-diethyl-7-hydroxy-3,4-dihydro-2H-chromen-4-one

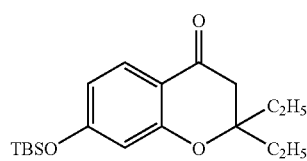

Pyrrolidine (9.3 g) and pentan-3-one (11.3 g) were added to a solution of 1-(2,4-dihydroxyphenyl)ethanone (14 g) in methanol (150 mL) and the solution was stirred for 24 hours and then heated under reflux for 10 hours. The reaction mixture was concentrated in vacuo, and to the residue was added water (10 mL). To the mixture was added 1N hydrochloric acid solution to adjust its pH to 5 to 6, and extracted with ethyl acetate (25 mL×3). The combined organic layer was dried over sodium sulfate, filtered and the filtrate was concentrated in vacuo. The resultant crude product was purified by column chromatography on silica gel (Solvent; petroleum ether/ethyl acetate=10/1) to give the titled compound (8 g) as a colorless powder.

(2) Preparation of 2,2-diethyl-7-tert-butyldimethylsilyloxy-3,4-dihydro-2H-chromen-4-one

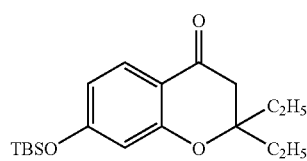

TBS: tert-butyldimethylsilyl group

Imidazole (5 g) was added to a solution of the compound obtained in (1) described above (8 g) in tetrahydrofuran (100 mL) and the mixture was stirred for 30 minutes. To the reaction solution was added tert-butyldimethylsilylchloride (13 g) and the mixture was further stirred for 2 hours. To the reaction mixture was added brine (20 mL) and the mixture was extracted with ethyl acetate (40 ml×3). The combined organic layer was dried over sodium sulfate, filtered, and the filtrate was concentrated in vacuo. The resultant oily residue was purified by column chromatography on silica gel (Solvent; petroleum ether/ethyl acetate=100/1) to give the titled compound (3.5 g) as a colorless powder.

(3) Preparation of (2,2-diethyl-7-tert-butyldimethylsilyloxy-2H-chromen-4-yl)trifluoromethanesulfonic acid

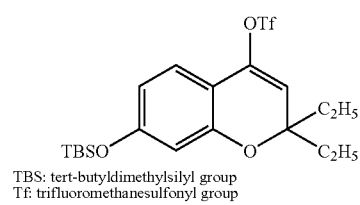

TBS: tert-butyldimethylsilyl group
Tf: trifluoromethanesulfonyl group

Trifluoromethanesulfonic anhydride (4.4 g) was added to a solution of the compound obtained in (2) described above (3.5 g) in dichloromethane (50 mL) under cooling at −30° C., and 2,6-lutidine (1.68 g) was added thereto. The mixture was gradually warmed to room temperature under stirring for 5 hours. A saturated aqueous solution of sodium bicarbonate (20 mL) was added to the reaction mixture, the mixture was extracted with dichloromethane (20 mL×3) and the combined organic layer was dried over sodium sulfate, filtered and the filtrate was concentrated in vacuo. The residue was purified by column chromatography on silica gel (Solvent; petroleum ether/ethyl acetate=100/1) to give the titled compound (3.5 g) as a colorless powder.

(4) Preparation of 4-(4-fluorophenyl)-7-hydroxy-2,2diethyl-2H-chromen

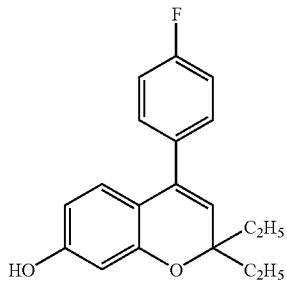

A mixture of the compound obtained in (3) described above (3.5 g), 4-fluorophenylboronic acid (1 g), cesium carbonate (12.7 g) and [1,1'-bis(diphenylphosphino)ferrocene] dichloropalladium(II) (350 mg, 10% wt) in dimethoxyethane/water (3/1; 60 mL) was heated under reflux under nitrogen atmosphere for 12 hours. The reaction solution was concentrated in vacuo, and the residue was extracted with ethyl acetate (40 ml×3). The combined organic layer was washed with saturated brine, dried over sodium sulfate, filtered and the filtrate was concentrated in vacuo. The residue is purified by column chromatography on silica gel (Solvent: petroleum ether/ethyl acetate=20/1) to give the titled compound (2 g) as a colorless powder.

(5) Preparation of 4-(4-fluorophenyl)-2,2diethyl-7-trifluoromethanesulfonyloxy-2H-chromen

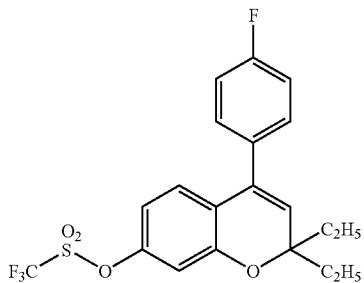

Trifluoromethanesulfonic anhydride (735 mg) was added to a solution of the compound obtained in (4) described above (600 mg) in dichloromethane (10 mL) under cooling at −30° C., and 2,6-lutidine (280 mg) was added thereto. The mixture was gradually warmed to room temperature under stirring for 5 hours. A saturated aqueous solution of sodium bicarbonate (10 mL) was added to the reaction mixture, and the mixture was extracted with dichloromethane (10 mL×3). The combined organic layer was dried over sodium sulfate, filtered and the filtrate was concentrated in vacuo. The residue is purified by column chromatography on silica gel (Solvent; petroleum ether/ethyl acetate=100/1) to give the titled compound (650 mg) as a colorless powder.

Reference Example 38

(1) Preparation of 2,2-dimethyl-7-tert-butyldimethylsilyloxy-2H-chromen-4-yl trifluoromethanesulfonate

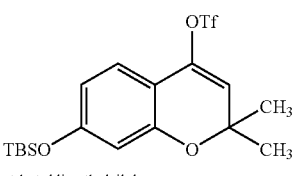

TBS: tert-butyldimethylsilyl group
Tf: trifluoromethanesulfonyl group

A corresponding starting compound was treated in the same manner as Reference Example 37(1) to (3) to give the titled compound as a colorless powder.

(2) Preparation of 4-(4-fluorophenyl)-7-hydroxy-2,2-dimethyl-2H-chromen

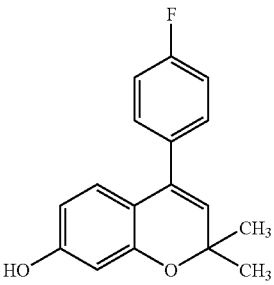

The compound obtained in (1) described above (8 g) and 4-fluorophenylboronic acid (3.07 g) were treated in the same manner as Reference Example 37(4) to give the titled compound (4.6 g) as a colorless powder.

(3) Preparation of [4-(4-fluorophenyl)-2,2-dimethyl-2H-chromen-7-yl]trifluoromethanesulfonate

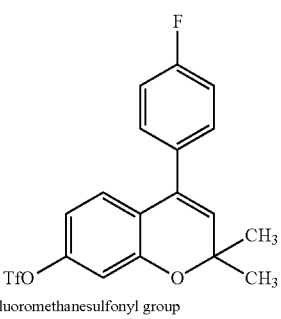

Tf: trifluoromethanesulfonyl group

The compound obtained in (2) described above (4.1 g) was treated in the same manner as Reference Example 37(5) to give the titled compound (4.6 g) as a colorless powder.

(4) Preparation of tert-butyl [4-(4-fluorophenyl)-2,2-dimethyl-2H-chromen-7-yl]carbamate

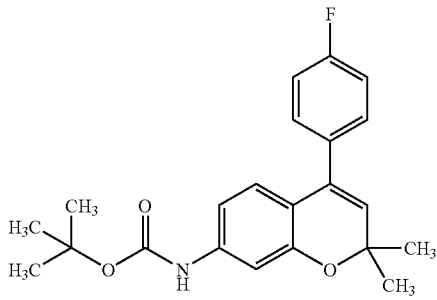

A mixture of the compound obtained in (3) described above (5.9 g), tert-butyl carbamate (2.06 g), cesium carbonate (9.6 g), tris(dibenzylideneacetone)dipalladium(0) (420 mg), biphenyl-2-yl-dibutylphosphate (840 mg) and 1,4-dioxane (30 mL) was heated under reflux under nitrogen atmosphere for 10 hours. The reaction mixture was filtered, and the filtrate was concentrated in vacuo. The residue is purified by column chromatography on silica gel (Solvent; petroleum ether/ethyl acetate=100/1) to give the titled compound (2.8 g) as a yellow powder.

APCI-MS m/z: 387 [M+NH$_4$]$^+$

(5) Preparation of 4-(4-fluorophenyl)-2,2-dimethyl-2H-chromen-7-amine

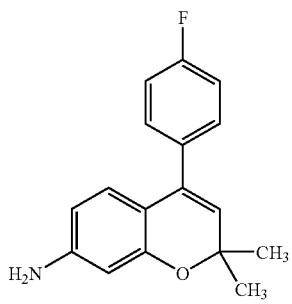

A mixture of the compound obtained in (4) described above (2.8 g) and 2M hydrochloric acid-dichloromethane solution (100 mL) was stirred at room temperature overnight. The reaction mixture was washed successively with a saturated aqueous solution of sodium bicarbonate and brine, dried over sodium sulfate and concentrated in vacuo. The residue is purified by flush chromatography on silica gel (Solvent; petroleum ether/ethyl acetate=25/1) to give the titled compound (1.9 g) as a yellow powder.

APCI-MS m/z: 270[M+H]$^+$

(6) Preparation of 4-(4-fluorophenyl)-2,2-dimethyl-2H-chromen-7-sulfonyl chloride To a solution of the compound obtained in (5) described above (1.5 g) in acetonitrile (30 mL) was added acetic acid (2.62 mL) and then thereto was added hydrochloric acid (2.62 mL) over a period of 2 minutes at room temperature. To the mixture was added an aqueous solution of sodium nitrite (4.24 g) in water (1.62 mL) over a period of one minute, and the mixture was stirred at 5° C. for 20 minutes. The reaction vessel was pressurized with sulfur dioxide gas for 35 minutes (the inner temperature was below 10° C.). Then an aqueous solution (1.62 mL) of cupric chloride(II) (754 mg) was added to the reaction solution, and the mixture was stirred at room temperature for one hour. Water (30 mL) was added to the reaction solution, and the mixture was extracted with dichloromethane (30 mL×3). The combined organic layer was washed successively with water and brine, dried over sodium sulfate and concentrated in vacuo to give the titled compound (2 g) as a crude product, which was used in the next step without further purification.

Reference Example 39

(1) Preparation of 4-chloro-2,2-dimethyl-7-nitro-2H-1,3-benzoxazine

Phosphorus pentachloride (5.5 g) was added to a solution of 2,2-dimethyl-7-nitro-3,4-dihydro-2H-1,3-benzoxazine-4-one (4 g) in phosphoryl chloride (15 mL) at 0° C., and the mixture was stirred at room temperature for one hour. The mixture was heated to 60° C. and stirred at the same temperature overnight. After cooling to 0° C., the reaction mixture was poured into ice water (300 mL) After stirring for 30 minutes, the mixture was extracted with ethyl acetate (100 mL×2). The combined organic layer was washed with brine (100 mL×2), dried over sodium sulfate and concentrated in vacuo to give the titled compound (2.34 g) as a brown oil, which was used in the next step without further purification.

(2) Preparation of 4-(4-fluorophenyl)-2,2-dimethyl-7-nitro-2H-1,3-benzoxazine

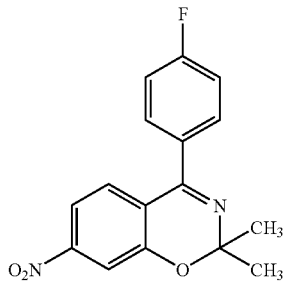

A mixture of the compound obtained in (1) described above (1.75 g), 4-fluorophenylboronic acid (1.53 g), potassium carbonate (1.55 g) and a catalytic amount of [1,1'-bis(diphenylphosphino)ferrocene]dichloropalladium(II) in dimethoxyethane (30 mL) was heated under reflux under nitrogen atmosphere overnight. After cooling to room temperature, to the reaction mixture was added ethyl acetate (30 mL) and saturated brine (30 mL). The organic layer was separated and washed with brine, dried over sodium sulfate and concentrated in vacuo. The residue is purified by flush chromatography on silica gel (petroleum ether/ethyl acetate=10/0 to 10/1) to give the titled compound (1.0 g) as a yellow powder.

ACPI-MS m/z: 301 $[M+H]^+$

(3) Preparation of 4-(4-fluorophenyl)-2,2-dimethyl-2H-1,3-benzoxazin-7-amine

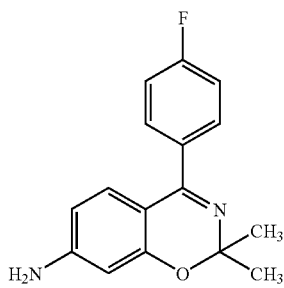

A mixture of the compound obtained in (2) described above (2.2 g), reduced iron (2.0 g), ammonium chloride (780 mg), ethanol (40 mL) and water (10 mL) was heated under reflux for an hour. After cooling to room temperature, the reaction solution was filtered through Celite and the filtrate was concentrated in vacuo. Dichloromethane (50 mL) and water (50 mL) were added to the residue, and the aqueous layer was separated and extracted with dichloromethane (40 mL×2). The combined organic layer was washed with brine, dried over sodium sulfate and concentrated in vacuo to give the titled compound (2.0 g) as a yellow powder, which was used in the next step without further purification.

Reference Example 40

(1) Preparation of (4-fluorophenl)(2,4-dimethoxy-1-methylphenyl)ketone

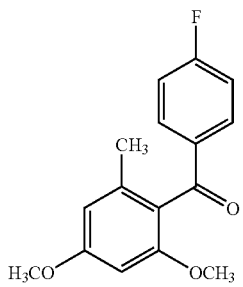

4-Fluorobenzoyl chloride (7.76 mL) was added to a solution of 3,5-dimethoxytoluene (10 g) in dichloromethane (200 mL) and aluminum chloride (13.7 g) was added to the solution cooled at −40° C. and the mixture was stirred at the same temperature for 30 minutes. The reaction mixture was poured into ice water and the mixture was extracted with dichloromethane (200 mL×3). The combined organic layer was washed with brine, dried over sodium sulfate and concentrated in vacuo. The residue was purified by column chromatography on silica gel (Solvent; petroleum ether/ethyl acetate=50/1) to give the titled compound (7.5 g) as a yellow powder.

(2) Preparation of (4-fluorophenyl)(2,4-dihydroxy-1-methylphenyl)ketone

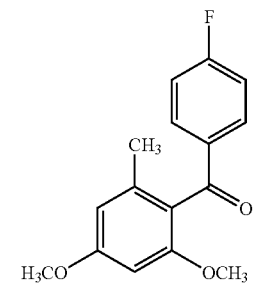

Boron tribromide (7 mL) was added to a solution of the compound obtained in (1) described above (7.5 g) in dichloromethane (120 mL) and the mixture was stirred at 40° C. for 5 hours. The reaction solution was poured into ice water and the mixture was extracted with dichloromethane (200 mL×3). The combined organic layer was washed with 1N hydrochloric acid, dried over sodium sulfate and concentrated in vacuo. The residue was purified by column chromatography on silica gel (Solvent: petroleum ether/ethyl acetate=50/1) to give the titled compound (5.5 g) as a pale yellow powder.

(3) Preparation of (4-fluorophenyl)(2,4-dihydroxy-1-methylphenyl)carboimine

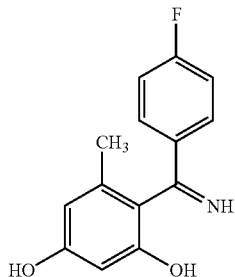

Titanium chloride (2 mL) was added to a solution of the compound obtained in (2) described above (2.46 g) in anhydrous toluene (120 mL) at −30° C. under nitrogen atmosphere, and then ammonia gas was introduced thereto for 30 minutes. The mixture was warned to room temperature and stirred overnight. To the reaction mixture was added a saturated aqueous solution of potassium carbonate (40 mL) and the mixture was stirred further for one hour. The organic layer was separated, dried and concentrated in vacuo. The residue was purified by column chromatography on silica gel (Solvent: petroleum ether/ethyl acetate=10/1) to give the titled compound (750 mg) as a yellow powder.

(4) Preparation of 4-fluorophenyl-7-hydroxy-2,2-dimethyl-5-methyl-2H-1,3-benzoxazine

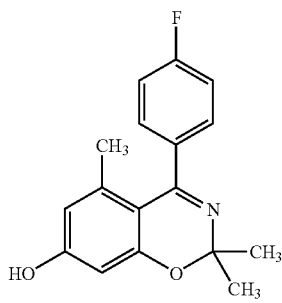

A mixture of the compound obtained in (3) described above (500 mg), p-toluenesulfonic acid monohydrate (50 mg) and 1,2-dimethoxypropane (20 ml) was heated under reflux for 2 hours. The reaction mixture was poured into an aqueous solution of sodium bicarbonate (10 mL) and the mixture was extracted with ethyl acetate (10 mL×3). The combined organic layer was washed with brine, dried over sodium sulfate and concentrated in vacuo. The residue was recrystallized from dichloromethane to give the titled compound (320 mg) as a yellow powder.

(5) Preparation of (4-fluorophenyl-2,2-dimethyl-5-methyl-2H-1,3-benzoxazine-7-yl)trifluoromethanesulfonate

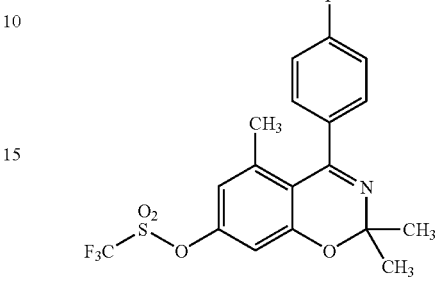

The compound obtained in (4) described above (320 mg) was treated in the same manner as Reference Example 37(5) to give the titled compound (350 mg) as a yellow oil, which was used in the next step without further purification.

Reference Example 41

(1) Preparation of 4-chloro-2,6-difluorobenzoic acid

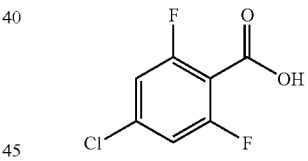

A solution of 1-chloro-3,5-difluorobenzene (1 g) in anhydrous tetrahydrofuran (20 ml) was degassed under stirring and substituted with nitrogen gas several times. Under cooling at −78° C., and thereto was added dropwise n-butyl lithium (5.4 mL) under nitrogen atmosphere over a period of 30 minutes. The mixture was stirred at −78° C. under nitrogen atmosphere for 8 hours. After addition of dry ice, the reaction mixture was stirred at room temperature for 24 hours. The mixture was concentrated in vacuo, and to the residue was added an aqueous 2N sodium hydroxide solution was added. The aqueous layer was washed with diethyl ether (10 mL) and the organic layer was removed. The aqueous solution was acidified with concentrated hydrochloric acid, and the mixture was extracted with ethyl acetate (20 mL×2). The combined organic layer was washed with brine, dried and concentrated to give the titled compound (1.06 g), which was used in the next step without further purification.

(2) Preparation of 4-chloro-2,6-difluoro-N-methyl-N-methoxybenzamide

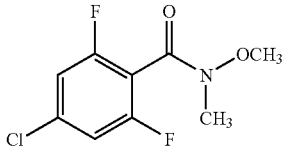

O-(7-Azabenzotriazol-1-yl)-N,N,N',N'-tetramethyluronium hexafluorophosphate (HATU; 2.36 g), diisopropylethylamine (1.68 g) and N,O-dimethylhydroxylamine (0.604 g) were added to a solution of the compound obtained in (1) described above (1.0 g) in dimethylformamide (10 mL) at 25° C. and the mixture was stirred at the same temperature for 2.5 hours. The reaction solution was diluted with ethyl acetate (20 mL), washed with brine, dried over sodium sulfate and concentrated in vacuo to give the titled compound (0.99 g) as a yellow powder, which was used in the next step without further purification.

(3) Preparation of 1-(4-chloro-2,6-difluorophenyl)ethanone

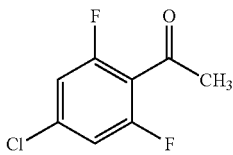

Methylmagnesium bromide (1.7 ml) was added dropwise to a solution of the compound obtained in (2) described above (1.0 g) in tetrahydrofuran (10 mL) under nitrogen atmosphere at 0° C., and the mixture was stirred at 20° C. for one hour. The reaction mixture was poured into an aqueous solution of ammonium chloride and the mixture was extracted with ethyl acetate (20 mL×2). The combined organic layer was washed with brine, dried over sodium sulfate and concentrated in vacuo to give the titled compound (0.713 g) as a yellow liquid.

(4) Preparation of 1-(2-benzyloxy-4-chloro-6-fluorophenyl)ethanone

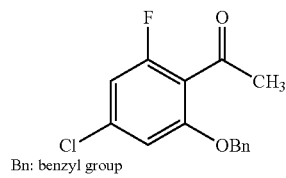

Bn: benzyl group

Sodium hydride (64 mg) was added to a solution of benzyl alcohol (173 mg) in dimethylformamide (3 mL) at 0° C. and the mixture was stirred at 20° C. for one hour. To the reaction solution was added a solution of the compound obtained in (3) described above (0.2 g) in tetrahydrofuran (1.3 mL), and the mixture was stirred at 20° C. for 3 hours. The reaction solution was poured into an aqueous solution of ammonium chloride and the mixture was extracted with ethyl acetate (10 mL×2). The combined organic solution was washed with brine, dried over sodium sulfate and concentrated in vacuo to give the titled compound (0.21 g) as a yellow powder.

(5) Preparation of 1-(4-chloro-6-fluoro-2-hydroxyphenyl)ethanone

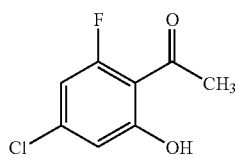

Palladium-carbon (30 mg) was added to a solution of the compound obtained in (4) described above (100 mg) in methanol (5 mL) under nitrogen atmosphere, and the mixture was degassed under nitrogen atmosphere and substituted with hydrogen gas several times. The mixture was stirred at 20° C. for 1.5 hours. The reaction mixture was filtered through Celite, and the filtrate and washing (methanol: 10 mL×2) were combined and concentrated in vacuo to give the titled compound (31.1 mg) as a yellow liquid.

(6) Preparation of 7-chloro-5-fluoro-2,2-dimethyl-3,4-dihydro-2H-chromen-4-one

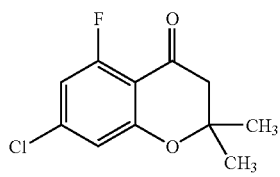

The compound obtained in (5) described above (2.817 g) was treated in the same manner as Reference Example 37(1) to give the titled compound (3.69 g) as a pale yellowish brown powder.

(7) Preparation of 7-chloro-5-fluoro-2,2-dimethyl-2H-chromen-4-yl trifluoromethanesulfonate

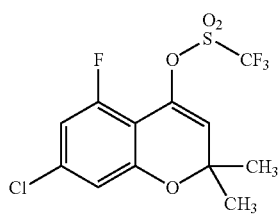

The compound obtained in (6) described above (1.0 g) was treated in the same manner as Reference Example 37(3) to give the titled compound (101 mg) as a yellow liquid.

(8) Preparation of 7-chloro-5-fluoro-4-(4-fluorophenyl)-2,2-dimethyl-2H-chromen

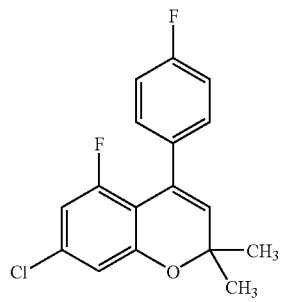

4-Fluorophenylboronic acid (68.5 mg) and tetrakis(triphenylphosphine)palladium (50 mg) were added to a solution of the compound obtained in (7) described above (100 mg) in dimethylformamide/water (5 mL/0.5 mL) under nitrogen atmosphere at 20° C., and then cesium carbonate (159.3 mg) was added thereto. The mixture was stirred at 80° C. for 6 hours. The reaction mixture was filtered and the filtrate was diluted with ethyl acetate. The organic layer was washed with brine, dried over sodium sulfate and concentrated in vacuo to give the titled compound (71 mg) as a pale yellow powder.

Reference Example 42

(1) Preparation of 5-chloro-2-pyridineboronic acid N-phenyldiethanolamine ester

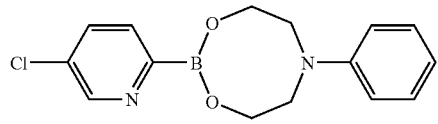

A hexane solution of n-butyl lithium (2.5M, 46.2 mL) was added to a solution of 2-bromo-5-chloropyridine (18.5 g) and triisopropyl borate (26.7 mL) in anhydrous tetrahydrofuran (200 mL) at −70° C. under stirring and under nitrogen atmosphere. The mixture was warmed to room temperature and stirred at the same temperature overnight. To the reaction solution was added a solution of N-phenyl-diethanolamine (17.4 g) in tetrahydrofuran (40 mL), and the mixture was heated under reflux for 4 hours. The reaction solution was concentrated in vacuo, and isopropyl alcohol was added to the residue (the same procedure was repeated twice). The mixture was suspended in isopropyl alcohol (100 mL) and stirred at room temperature overnight. The precipitate was filtered to give the titled compound (36 g) as a yellow powder.

(2) Preparation of 4-(5-chloropyridin-2-yl)-2,2-dimethyl-7-(tert-butyldimethylsilyloxy)-2H-chromen

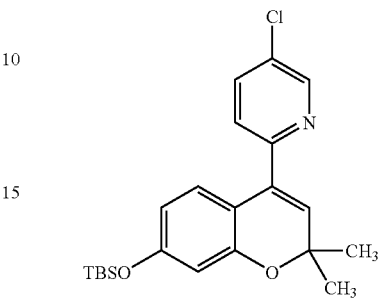

TBS: tert-butyldimethylsilyl group

A mixture of the compound obtained in (1) described above (20 g), [2,2-diethyl-7-(tert-butyldimethylsilyloxy)-2H-chromen-4-yl]trifluoromethanesulfonic acid (an objective compound of Reference Example 38(1); 10 g), palladium acetate (0.3 g), triphenylphosphine (1.2 g), copper iodide (2 g) and potassium carbonate (5 g) was heated under reflux and under nitrogen atmosphere overnight. The reaction mixture was extracted with ethyl acetate (100 mL×3), and the combined organic layer was dried over sodium sulfate and concentrated in vacuo. The residue was purified by column chromatography on silica gel (Solvent; petroleum ether) to give the titled compound (4.0 g) as a brown powder.

(3) Preparation of 4-(5-chloropyridin-2-yl)-7-hydroxy-2,2-dimethyl-2H-chromen

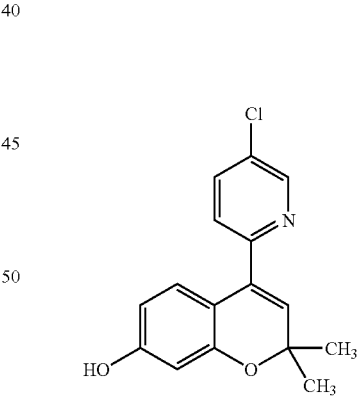

To a solution of the compound obtained in (2) described above (2 g) in tetrahydrofuran (20 mL) was added 1M solution of tetrabutylammonium fluoride in tetrahydrofuran (10 mL) under stirring at 0° C. and the mixture was stirred at the same temperature for 3 hours. The reaction solution was diluted with an aqueous solution of ammonium chloride (50 mL) and extracted with ethyl acetate (30 mL×3). The combined organic layer was dried over sodium sulfate and concentrated in vacuo to give the titled compound (1.5 g) as a brown powder, which was used in the next step without further purification.

(4) Preparation of 4-(5-chloropyridin-2-yl)-7-hydroxy-2,2-dimethyl-2H-chromen-7-yl trifluoromethanesulfonate

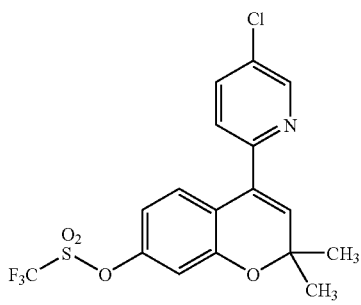

The compound obtained in (3) described above (1.5 g) was treated in the same manner as Reference Example 37(5) to give the titled compound (1.4 g) as a brown powder.

Reference Example 43

(1) Preparation of 5-fluoro-2-pyridineboronic acid N-phenyldiethanolamine ester

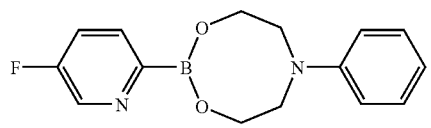

2-Bromo-5-fluoropyridine (13 g) and N-phenyl-diethanolamine (13.4 g) were treated in the same manner as Reference Example 42(1) to give the titled compound (17 g) as a yellow powder.

(2) Preparation of 4-(5-fluoropyridine-2-yl)-2,2-dimethyl-7-(tert-butyldimethylsilyloxy)-2H-chromen

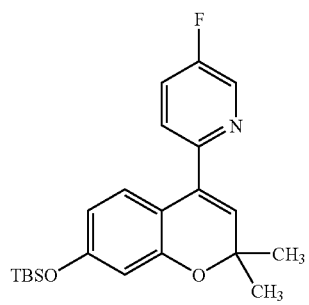

TBS: tert-butyldimethylsilyl

The compound obtained in (1) described above (10 g) and [2,2-diethyl-7-(tert-butyldimethylsilyloxy)-2H-chromen-4-yl]trifluoromethanesulfonic acid (a objective compound in Reference Example 38; 7 g) were treated in the same manner as Reference Example 42(2) to give the titled compound (2.3 g) as a brown powder.

(3) Preparation of 4-(5-fluoropyridine-2-yl)-2,2-dimethyl-7-hydroxy-2H-chromen

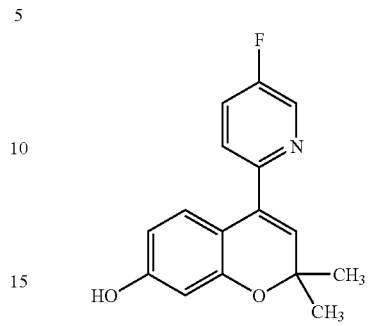

The compound obtained in (2) described above (2 g) was treated in the same manner as Reference Example 42(3) to give the titled compound (1.6 g) as a brown powder, which was used in the next step without further purification.

(4) Preparation of 4-(5-fluoropyridine-2-yl)-7-hydroxy-2,2-dimethyl-2H-chromen-7-yl trifluoromethanesulfonate

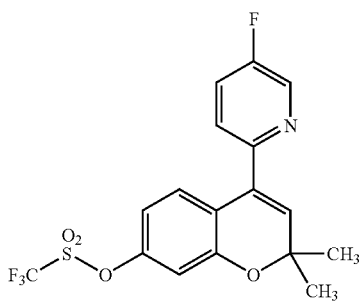

The compound obtained in (3) described above (1.4 g) was treated in the same manner as Reference Example 42(4) to give the titled compound (0.8 g) as a colorless oil.

Reference Example 44

(1) Preparation of 7-hydroxy-2,2,5-trimethyl-3,4-dihydro-2H-chromen-4-one

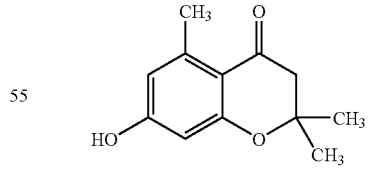

Anhydrous 5-methylbenzen-1,3-diol (3.678 g), 3,3-dimethylacrylic acid (3.3 mL) and aluminum chloride (14.76 g) were added to phosphoryl chloride (45 mL) and the mixture was shaken at room temperature for 6 hours. The reaction solution was poured into ice, and the precipitates were filtered, washed with water and dried. The precipitates were purified by column chromatography on silica gel (Solvent; petroleum ether/ethyl acetate=25/1) to give the titled compound (3.8 g) as a colorless powder.

(2) Preparation of 7-(tert-butyldimethylsilyloxy)-2,2,5-trimethyl-3,4-dihydro-2H-chromen-4-one

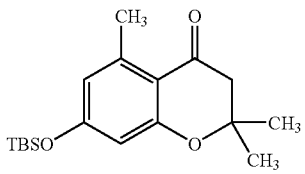

TBS: tert-butyldimethylsilyl group

Imidazole (1.88 g) was added to a solution of the compound obtained in (1) described above (3.8 g) in tetrahydrofuran (80 mL) at room temperature, and the mixture was stirred for one hour. Tert-butyldimethylsilylchloride (4.2 g) was added to the reaction solution, and the mixture was further stirred for 2 hours. The reaction solution was concentrated in vacuo, and the residue was washed with brine (40 mL) and extracted with ethyl acetate (50 mL×3). The combined organic layer was dried over sodium sulfate, filtered and the filtrate was concentrated in vacuo. The residue was purified by column chromatography on silica gel (Solvent; petroleum ether/ethyl acetate=50/1) to give the titled compound (4.5 g) as a colorless powder.

(3) Preparation of 7-(tert-butyldimethylsilyloxy)-2,2,5-trimethyl-2H-chromen-4-yl trifluoromethanesulfonate

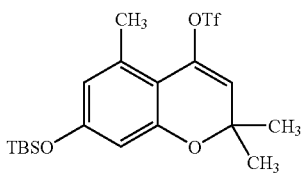

TBS: tert-butyldimethylsilyl group
Tf: trifluoromethanesulfonyl group

The compound obtained in (2) described above (4.5 g) was treated in the same manner as Reference Example 37(3) to give the titled compound (5.8 g) as a yellow powder.

(4) Preparation of 4-(4-fluorophenyl)-7-hydroxy-2,2,5-trimethyl-2H-chromen

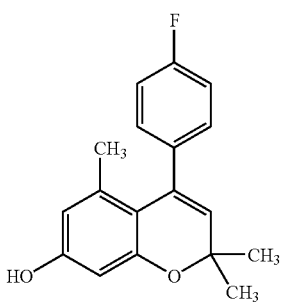

The compound obtained in (3) described above (5.8 g) was treated in the same manner as Reference Example 37(4) to give the titled compound (1.82 g) as a yellow powder.

(5) Preparation of [4-(4-fluorophenyl)-2,2,5-trimethyl-2H-chromen-7-yl]trifluoromethanesulfonate

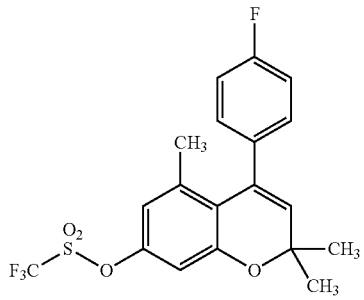

The compound obtained in (4) described above (1.8 g) was treated in the same manner as Reference Example 37(5) to give the titled compound (2.5 g) as a colorless oil.

Reference Example 45

Preparation of 4-fluorophenyl-2,2-dimethyl-2H-1,3-benzoxazin-7-sulfonylchloride

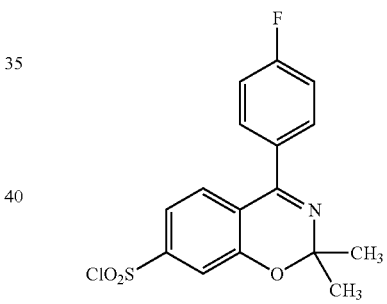

A solution of sodium nitrite (153 mg) in water (2.4 mL) was added dropwise to a solution of 4-fluorophenyl-2,2-dimethyl-2H-1,3-benzoxazin-7-amine (an objective compound of Reference Example 38(3); 600 mg) in acetic acid (18 mL) and concentrated hydrochloric acid (6 mL) at −5° C. and the mixture was stirred at the same temperature for one hour. To the reaction mixture was added a mixture of sulfur dioxide, acetic acid, cupric chloride and water at 0° C. and the mixture was stirred at the same temperature for one hour. The reaction mixture was poured into ice water (200 mL) and the mixture was extracted with ether (50 mL×3). The combined organic layer was washed successively with brine (50 mL) and a saturated aqueous solution of sodium bicarbonate (50 mL×2), dried over sodium sulfate and concentrated in vacuo to give the titled compound (400 mg) as a yellow oil, which was used in the next step without further purification.

Reference Example 46-53

Corresponding starting compounds were treated in the same manner as Reference Example 37 to give the compounds in Table 16 and 17.

TABLE 16

| Reference Example | structure | physicochemical properties |
|---|---|---|
| 46 | (4-phenyl-2,2-dimethyl-2H-chromen-7-yl trifluoromethanesulfonate) | colorless oil |
| 47 | (4-(4-chlorophenyl)-2,2-dimethyl-2H-chromen-7-yl trifluoromethanesulfonate) | colorless oil |
| 48 | (4-(4-chloro-3-methylphenyl)-2,2-dimethyl-2H-chromen-7-yl trifluoromethanesulfonate) | colorless oil |
| 49 | (4-(4-chloro-2-methylphenyl)-2,2-dimethyl-2H-chromen-7-yl trifluoromethanesulfonate) | colorless oil |
| 50 | (4-(4-chloro-3-fluorophenyl)-3-cyano-2,2-dimethyl-2H-chromen-7-yl methanesulfonate) | colorless oil |

TABLE 17

| Reference Example | structure | physicochemical properties |
|---|---|---|
| 51 | (4-(4-chloro-2-fluorophenyl)-2,2-dimethyl-2H-chromen-7-yl trifluoromethanesulfonate) | colorless oil |
| 52 | (4-(4-fluorophenyl)-2H-spiro[chromene-2,1'-cyclopentane]-7-yl trifluoromethanesulfonate) | colorless powder |
| 53 | (4-(4-trifluoromethylphenyl)-2,2-dimethyl-2H-chromen-7-yl trifluoromethanesulfonate) | pale yellow powder |

Reference Example 54

Preparation of [5-chloro-4-(4-fluorophenyl)-2,2-dimethyl-2H-chromen-7-yl]trifluoromethanesulfonate A corresponding starting compound was treated in the same manner as Reference Example 44 to give the titled compound (1.6 g) as a colorless oil.

Reference Example 55

Preparation of [5-chloro-4-(4-fluorophenyl)-2,2-dimethyl-2H-1,3-benzoxazin-7-yl]trifluoromethanesulfonate

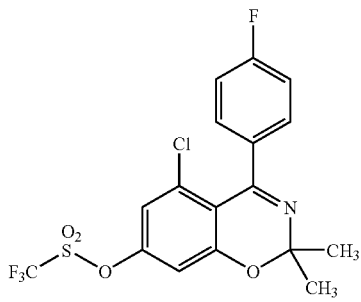

A corresponding starting compound was treated in the same manner as Reference Example 40 to give the titled compound (100 mg) as a pale yellow oil.

Reference Example 56

Preparation of [5-chloro-4-(2,4-difluorophenyl)-2,2-dimethyl-2H-1,3-benzoxazin-7-yl]trifluoromethanesulfonate

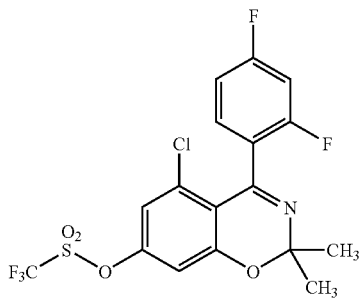

A corresponding starting compound was treated in the same manner as Reference Example 40 to give the titled compound (380 mg) as a pale yellow oil.

Reference Example 57

(1) Preparation of 2-hydroxy-4-nitrobenzamide

Dimethylformamide (5 drops) and oxalyl chloride (23.6 g) were added to a solution of 2-acetoxy-4-nitrobenzoic acid (a compound of Refererence Example 1(1); 20 g) in anhydrous dichloromethane (200 mL) at 0° C. with stirring, and the mixture was stirred at room temperature for one hour. The reaction solution was concentrated and the residue was diluted with dry tetrahydrofuran (200 mL). To the solution was added ammonia/tetrahydrofuran solution at −10° C. and the mixture was stirred at 0° C. for 30 minutes. The reaction solution was poured into saturated brine (1 L) and the organic layer was separated. The aqueous layer was adjusted to pH 5 with an aqueous 4M hydrochloric acid and extracted with ethyl acetate (500 mL×2). The combined organic layer was concentrated in vacuo to give the titled compound (13.75 g) as a colorless powder, which was used in the next step without further purification.

(2) Preparation of 2,2-diethyl-7-nitro-2,3-dihydro-4H-1,3-benzoxazin-4-one

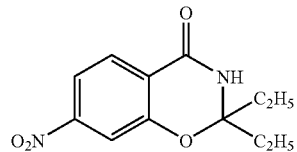

A suspension of the compound obtained in (1) described above (5 g), 3-pentanone (6.6 g) and p-toluenesulfonic acid monohydrate (1.6 g) in toluene (70 mL) was heated under reflux overnight. The reaction mixture was poured into a saturated aqueous solution of sodium bicarbonate (100 mL) and the mixture was extracted with ethyl acetate (100 mL×3). The combined organic layer was washed with brine, dried over sodium sulfate and concentrated in vacuo. The resultant residue was recrystallized from ethyl acetate/dichloromethane (1:1) to give the titled compound (5 g) as a colorless powder.

(3) Preparation of 4-chloro-2,2-diethyl-7-nitro-2H-1,3-benzoxazine

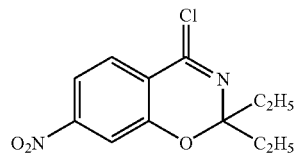

The compound obtained in (2) described above (1.5 g) was treated in the same manner as Reference Example 39(1) to give the titled compound (1 g) as a yellow oil, which was used in the next step without further purification.

(4) Preparation of 2,2-diethyl-4-(2,4-difluorophenyl)-7-nitro-2H-1,3-benzoxazine

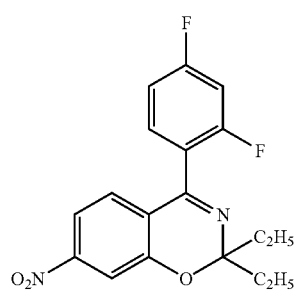

The compound obtained in (3) described above (1.0 g) and 2,4-difluorophenylboronic acid (1.2 g) were treated in the same manner as Reference Example 39(2) to give the titled compound (0.6 g) as a yellow oil.

(5) Preparation of 2,2-diethyl-4-(2,4-difluorophenyl)-2H-1,3-benzoxazin-7-amine

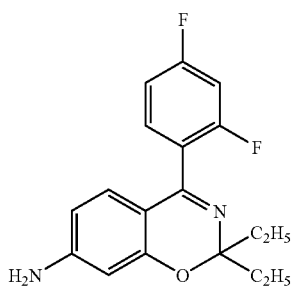

The compound obtained in (4) described above (600 mg) was treated in the same manner as Reference Example 39(3) to give the titled compound (500 mg) as a yellow powder, which was used in the next step without further purification.

Reference Example 58

Preparation of (5-chloro-2,2-diethyl-4-(4-fluorophenyl)-2H-1,3-benzoxazin-7-yl)trifluoromethanesulfonate

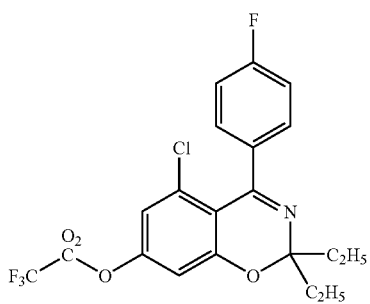

A corresponding starting compound was treated in the same manner as Reference Example 40(3), (4) and (5) to give the titled compound as a pale yellow oil.

Reference Example 59

Preparation of 2-ethyl-4-(2,4-difluorophenyl)-2-methyl-2H-1,3-benzoxazin-7-amine

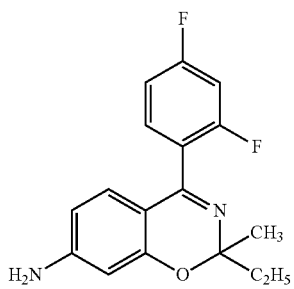

A corresponding starting compound was treated in the same manner as Reference Example 57 to give the titled compound as a yellow powder, which was used in the next step without further purification.

Reference Example 60

(1) Preparation of 2,2-diethyl-4-(4-fluorophenyl)-2H-1,3-benzoxazin-7-amine

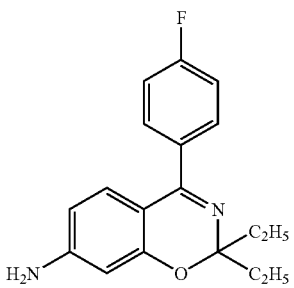

A corresponding starting compound was treated in the same manner as Reference Example 57(4) and (5) to give the titled compound as a yellow powder, which was used in the next step without further purification.

(2) Preparation of 2,2-diethyl-4-fluorophenyl-2H-1,3-benzoxazin-7-sulfonylchloride

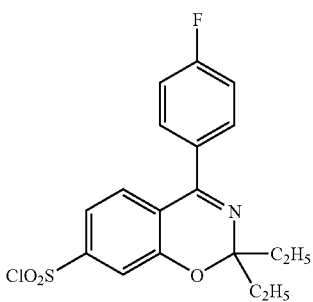

The compound obtained in (1) described above (700 mg) was treated in the same manner as Reference Example 45 to give the titled compound (600 mg) as a yellow powder, which was used in the next step without further purification.

Reference Example 61

Preparation of [2,2-dimethyl-4-(4-trifluoromethylphenyl)-2H-chromen-7-yl]trifluoromethanesulfonate

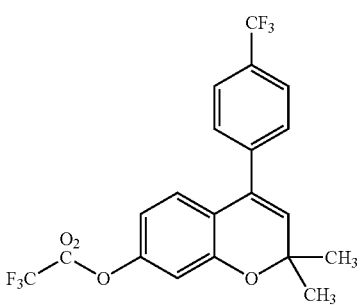

A corresponding starting compound was treated in the same manner as Reference Example 37 to give the titled compound as a pale yellow powder.

Experiment

[Aldosterone Receptor Binding Assay]

(1) Preparation of Kidney Cytosol Fraction:

Kidneys derived from post-adrenalectomy Sprague-Dawley male rats (7 weeks old) were homogenized in the following buffer solution and the homogenate was centrifuged at 100,000×g for 1 hour to give a supernatant as a kidney cytosol fraction (protein concentration: 15 mg/mL) for the present biding assay. Composition of Buffer solution:

50 mM Tris-HCl (pH 7.5), 250 mM Sucrose, 50 mM Potassium chloride, 3 mM Magnesium chloride, 20 mM Sodium molybdate and 1 mM Mercaptoethanol (2) Binding Assay:

A mixture of 5 μL of a solution of each test compound in dimethylsulfoxide, 200 μL of kidney cytosol fraction, 50 μL of physiological saline (or 50 μL of unlabeled aldosterone solution (final concentration: 1 μM) and 50 μL of [$^3$H] aldosterone solution (ca. 2 nM) was incubated in a test tube at 4° C. overnight. Thereto was added 100 μL of dextrane-coated charcoal/10 mM Tris-HCl buffer and the mixture was incubated at 4° C. for 30 minutes. The reaction mixture was centrifuged at 3000 rpm for 10 minutes and to the supernatant (150 μL) was added 5 mL of a scintillater (Clearsol I, Nakarai Tesque). The radioactivity was measured by a liquid scintilation counter (TRI CARB 2200C A, Packard). The concentration of each test compound required to produce 50% inhibition of aldosterone-binding to receptors (IC$_{50}$; μM) was calculated on the basis of the above quantitated radioactivity. Moreover, the dissociation constant (Ki) of each test compound was calculated on Cheng and Prusoff's equation (Ki=IC$_{50}$/(1+[L]/Kd), wherein [L] is [$^3$H] aldosterone concentration and Kd is the affinity constant of aldosterone).

(3) Results:

The results of the present binding assay are shown in the following Table 18. Meanwhile, the symbols (++ and +++) are defined as follows:

++: 0.5 μM<Ki<1 μM
+++: Ki<0.5 μM

TABLE 18

| Test Compounds | Ki |
| --- | --- |
| Example 1 | +++ |
| Example 6 | +++ |
| Example 8 | +++ |
| Example 10 | ++ |
| Example 26 | +++ |
| Example 42 | +++ |
| Example 47 | +++ |
| Example 55(2) compound (a) | +++ |
| Example 53(3) | +++ |
| Example 61 | ++ |

INDUSTRIAL APPLICABILITY

The compound [I] of the present invention shows a high affinity to mineralocorticoid receptor (MR) and thereby a modulating activity (e.g., antagonizing activity) on the receptor, and therefore it is useful as a medicament for prevention or treatment of various diseases associated with the receptor and/or aldosterone, such as cardiovascular diseases including hypertension and heart failure.

The invention claimed is:

1. A fused bicyclic compound of the following formula [I]:

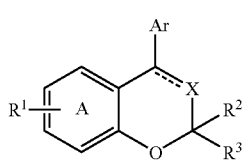

wherein
the ring A is optionally substituted with one or two substituent(s) selected from a halogen atom and a C$_{1-8}$ alkyl group, R$^1$ is an alkylsulfonylamino group or an alkylaminosulfonyl group, R$^2$ and R$^3$ are (a) the same or different and each is a hydrogen atom, an alkyl group or a substituted or unsubstituted aryl group, (b) combined with each other to form an oxo group or (c) combined with each other at its terminal together with the adjacent carbon atom to form a cycloalkyl group, X is =N—, and Ar is a 6- to 10-membered monocyclic or bicyclic aryl group optionally containing one or more heteroatom(s) selected from a sulfur atom, an oxygen atom, and a nitrogen atom, said aryl group being optionally substituted with one or two substituent(s) independently selected from a halogen atom, a cyano group, a C$_{1-8}$ alkyl group, a trihalogeno-C$_{1-8}$ alkyl group, and a C$_{1-8}$ alkoxy group, or a pharmaceutically acceptable salt thereof.

2. The compound of claim 1 wherein

R$^1$ is a C$_{1-8}$ alkylsulfonylamino group or a C$_{1-8}$ alkylaminosulfonyl group, R$^2$ and R$^3$ are (a) the same or different and each is a group selected from a hydrogen atom, a C$_{1-8}$ alkyl group, and 6- to 10-membered monocyclic or bicyclic aryl group wherein said aryl group is optionally substituted with a halogen atom, (b) combined with each other to form an oxo group or (c) combined with each other at its terminal together with the adjacent carbon atom to form a C$_{3-10}$ cycloalkyl group, and R$^1$ is bonded at the position 5, 6, or 7 on the following fused ring structure of the general formula [I]:

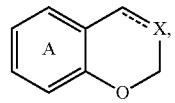

or a pharmaceutically acceptable salt thereof.

3. A fused bicyclic compound of claim 1, having the general formula [I-A]:

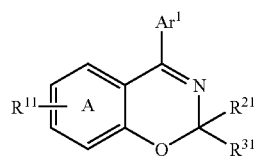

wherein
the ring A is as defined in claim 1,

R$^{11}$ is an alkylsulfonylamino group or an alkylaminosulfonyl group,

R$^{21}$ and R$^{31}$ are the same or different and each is (a) a hydrogen atom, (b) an alkyl group, or (c) a substituted or unsubstituted aryl group, and Ar$^1$ is as defined in claim 1, or a pharmaceutically acceptable salt thereof.

4. The compound of claim 3 wherein $R^{11}$ is bonded at the position 7 of the following fused ring moiety of the general formula [I-A]:

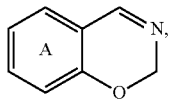

or a pharmaceutically acceptable salt thereof.

5. A compound of the general [I-A-a] below:

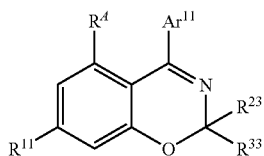

[I-A-a]

wherein
$R^{11}$ is an alkylsulfonylamino group or an alkylaminosulfonyl group,
$R^A$ is a hydrogen atom or an alkyl group,
either one of $R^{23}$ and $R^{33}$ is a hydrogen atom or an alkyl group, and the other one is an alkyl group or a phenyl group,
$Ar^{11}$ is a 5- to 10-membered monocyclic or bicyclic aromatic cyclic group (said cyclic group may contain a heteroatom selected from a sulfur atom and an oxygen atom)
or a pharmaceutically acceptable salt thereof.

6. The compound of claim 5 wherein
$R^{11}$ is a $C_{1-6}$ alkylsulfonylamino group,
$R^A$ is a hydrogen atom, a halogen atom or a $C_{1-6}$ alkyl group,
either one of $R^{23}$ and $R^{33}$ is a hydrogen atom or a $C_{1-6}$ alkyl group and the other one is a $C_{1-6}$ alkyl group,
$Ar^{11}$ is a phenyl group optionally substituted with one or two group(s) selected from a halogen atom and a $C_{1-6}$ alkyl group,
or a pharmaceutically acceptable salt thereof.

7. A compound selected from a group consisting of:
N-[4-(4-chlorophenyl)-2,2-dimethyl-2H-1,3-benzoxazin-7-yl]methanesulfonamide;
N-[4-(4-chloro-2-methylphenyl)-2,2-dimethyl-2H-1,3-benzoxazin-7-yl]-methanesulfonamide;
N-[4-(4-fluorophenyl)-2,2-dimethyl-2H-1,3-benzoxazin-7-yl]methanesulfonamide;
N-[4-(4-fluoro-2-methylphenyl)-2,2-dimethyl-2H-1,3-benzoxazin-7-yl]methanesulfonamide;
N-[4-(4-chloro-3-methylphenyl)-2,2-dimethyl-2H-1,3-benzoxazin-7-yl]methanesulfonamide;
N-[4-(4-chloro-3-fluorophenyl)-2,2-dimethyl-2H-1,3-benzoxazin-7-yl]methanesulfonamide;
N-[4-(4-fluoro-3-methylphenyl)-2,2-dimethyl-2H-1,3-benzoxazin-7-yl]methanesulfonamide;
N-[4-(4-chloro-2-fluorophenyl)-2,2-dimethyl-2H-1,3-benzoxazin-7-yl]methanesulfonamide;
N-[5-chloro-4-(4-fluorophenyl)-2,2-dimethyl-2H-1,3-benzoxazin-7-yl]methanesulfonamide;
N-[2,2-diethyl-4-(4-fluorophenyl)-2H-1,3-benzoxazin-7-yl]methanesulfonamide;
N-[2-ethyl-4-(4-fluorophenyl)-2-methyl-2H-1,3-benzoxazin-7-yl]methanesulfonamide; and
N-[4-(4-fluorophenyl)-2,2,5-trimethyl-2H-1,3-benzoxazin-7-yl]methanesulfonamide,
or a pharmaceutically acceptable salt thereof.

8. A compound of the general formula [ii] below:

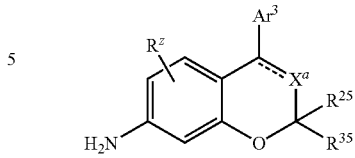

[ii]

wherein
$X^a$ is =N—,
$R^Z$ is a hydrogen atom or a halogen atom,
$R^{25}$ and $R^{35}$ are an alkyl group, and
$Ar^3$ is a phenyl group optionally substituted with one or two group(s) selected from a halogen atom and a trihalogenoalkyl group,
or a pharmaceutically acceptable salt thereof.

9. A pharmaceutical composition comprising:
a compound described in claim 1 or a pharmaceutically acceptable salt thereof as an active ingredient; and
a pharmaceutically acceptable carrier.

10. A method for treating hypertension, heart failure, cardiac infarction, angina pectoris, cardiac hypertrophy, cardiomyositis, cardiac/vascular fibrosis, baroreceptor dysfunction, increased body fluid, arrhythmia, primary/secondary aldosteronism, Addison's disease, Cushing's syndrome, or Bartter's syndrome via modulation of mineralocorticoid receptors, said method comprising:
administering to a patient an effective amount of the composition of claim 9, wherein said compound or said pharmaceutically acceptable salt thereof is a modulator of mineralocorticoid receptors.

11. The method of claim 10 wherein said compound or said pharmaceutically acceptable salt thereof is a mineralocorticoid receptor antagonist or an aldosterone antagonist.

12. The method of claim 11, which comprises treating diseases or clinical conditions associated with an increased MR activity and/or an increased aldosterone level.

13. The method of claim 12 wherein said compound or said pharmaceutically acceptable salt thereof is a diuretic.

14. The method of claim 12, which comprises treating hypertension, heart failure, cardiac infarction, angina pectoris, cardiac hypertrophy, cardiomyositis, cardiac/vascular fibrosis, baroreceptor dysfunction, increased body fluid, or arrhythmia.

15. The method of claim 12, which comprises treating primary/secondary aldosteronism, Addison's disease, Cushing's syndrome, or Bartter's syndrome.

16. A pharmaceutical composition comprising the compound of claim 8 or a pharmaceutically acceptable salt thereof as an active ingredient.

17. A compound of the formula:

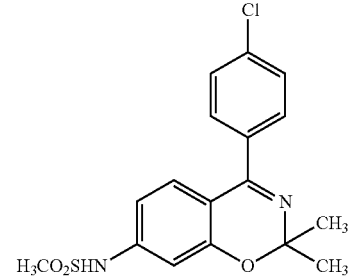

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,258,131 B2 | Page 1 of 1 |
| APPLICATION NO. | : 12/671479 | |
| DATED | : September 4, 2012 | |
| INVENTOR(S) | : Yoichi Takahashi et al. | |

It is certified that error appears in the above-identified patent and that said Letters Patent is hereby corrected as shown below:

ON THE TITLE PAGE:

At item [62] correct the Related U.S. Application Data to read as follows:

--Division of application No. 12/671,479, filed as application No. PCT/JP2008/063751 on Jul. 31, 2008, now Pat. No. 8,258,131.--

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,258,131 B2
APPLICATION NO. : 12/671479
DATED : September 4, 2012
INVENTOR(S) : Yoichi Takahashi et al.

It is certified that error appears in the above-identified patent and that said Letters Patent is hereby corrected as shown below:

ON THE TITLE PAGE:

At item (22), change the filing date of the PCT application from "Jul. 21, 2008" to --Jul. 31, 2008--.

At item [62] correct the Related U.S. Application Data to read as follows:
--Division of application No. 12/671,479, filed as application No. PCT/JP2008/063751 on Jul. 31, 2008, now Pat. No. 8,258,131.--

This certificate supersedes the Certificate of Correction issued July 30, 2013.

Signed and Sealed this
Third Day of September, 2013

Teresa Stanek Rea
*Acting Director of the United States Patent and Trademark Office*